United States Patent
Ohkawa et al.

(10) Patent No.: US 7,276,527 B2
(45) Date of Patent: *Oct. 2, 2007

(54) 5-PYRIDYL-1,3-AZOLE COMPOUNDS, PROCESS FOR PRODUCING THE SAME AND USE THEREOF

(75) Inventors: Shigenori Ohkawa, Takatsuki (JP); Naoyuki Kanzaki, Ibaraki (JP); Seiji Miwatashi, Hyogo (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/354,897

(22) Filed: Feb. 16, 2006

(65) Prior Publication Data

US 2006/0135566 A1 Jun. 22, 2006

Related U.S. Application Data

(63) Continuation of application No. 09/959,356, filed as application No. PCT/JP00/02575 on Apr. 20, 2000, now Pat. No. 7,101,899.

(30) Foreign Application Priority Data

Apr. 23, 1999 (JP) .................................. 11/116686
Aug. 6, 1999 (JP) .................................. 11/224650

(51) Int. Cl.
*A61K 31/4436* (2006.01)
*C07D 417/04* (2006.01)

(52) U.S. Cl. .................................. 514/342; 546/270.4
(58) Field of Classification Search ............. 546/270.4; 514/342
See application file for complete search history.

(56) References Cited

U.S. PATENT DOCUMENTS

| | | | |
|---|---|---|---|
| 4,612,321 | A | 9/1986 | Terao et al. |
| 7,101,899 | B1 * | 9/2006 | Ohkawa et al. ............. 514/342 |
| 2004/0097555 | A1 | 5/2004 | Ohkawa et al. |
| 2005/0080113 | A1 | 4/2005 | Ohkawa et al. |

FOREIGN PATENT DOCUMENTS

| | | |
|---|---|---|
| JP | 5-70446 | 3/1993 |
| WO | 97/12876 | 4/1997 |
| WO | 98/14191 | 4/1998 |
| WO | 99/21555 | 5/1999 |
| WO | 2000 064894 | 11/2000 |

OTHER PUBLICATIONS

Hcaplus 129:76589.
Lozano et al., "New developments in understanding the etiology of Parkinson's disease and in its treatment", Current Opinion in Neurolbiology, vol. 8, pp. 783-790, 1998.
Hcaplus 130:75567.

* cited by examiner

*Primary Examiner*—Patricia L. Morris
(74) *Attorney, Agent, or Firm*—Wenderoth, Lind & Ponack, L.L.P.

(57) ABSTRACT

An optionally N-oxidized compound represented by the formula:

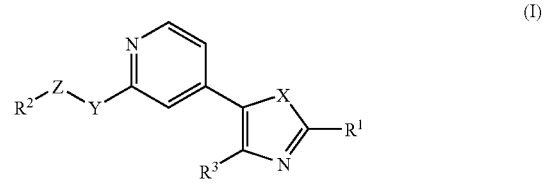

(I)

wherein $R^1$ represents hydrogen, hydrocarbon, heterocycle, amino, acyl, $R^2$ represents an aromatic group, $R^3$ represents hydrogen, pyridyl, aromatic hydrocarbon, X represents oxygen, optionally oxidized sulfur, Y represents a bond, an oxygen, optionally oxidized sulfur, a group represented by the formula $NR^4$ ($R^4$ represents hydrogen, hydrocarbon or acyl) and Z represents a bond or a divalent acyclic hydrocarbon, or a salt thereof has an excellent adenosine $A_3$ receptor antagonistic activity and is used as an agent for preventing or treating diseases related to an adenosine $A_3$ receptor. Furthermore, the compound (I) or a salt thereof has p38 MAP kinase inhibitory activity and TNF-α inhibitory activity and is used as an agent for preventing or treating diseases related to p38 MAP kinase and diseases related to TNF-α.

22 Claims, No Drawings

SEQUENCE LISTING

```
<160> NUMBER OF SEQ ID NOS: 8

<210> SEQ ID NO 1
<211> LENGTH: 34
<212> TYPE: DNA
<213> ORGANISM: Artificial Sequence
<220> FEATURE:
<223> OTHER INFORMATION: Oligonucleotide designed to act as PCT primer
      for detectionof adenosine A3 receptor gene.

<400> SEQUENCE: 1
cgcctctaga caagatgccc aacaacagca ctgc                                 34

<210> SEQ ID NO 2
<211> LENGTH: 34
<212> TYPE: DNA
<213> ORGANISM: Artificial Sequence
<220> FEATURE:
<223> OTHER INFORMATION: Oligonucleotide designed to act as PCT primer
      for detectionof adenosine A3 receptor gene.

<400> SEQUENCE: 2
cggggtcgac actactcaga attcttctca atgc                                 34

<210> SEQ ID NO 3
<211> LENGTH: 62
<212> TYPE: DNA
<213> ORGANISM: Artificial Sequence
<220> FEATURE:
<223> OTHER INFORMATION: Oligonucleotide designed to act as PCR primer
      for detectionof p38 MAP kinase gene.

<400> SEQUENCE: 3
accactcgag atggactaca aggacgacga tgacaagtct caggagaggc ccacgttct      60 cc                                                                    62

<210> SEQ ID NO 4
<211> LENGTH: 35
<212> TYPE: DNA
<213> ORGANISM: Artificial Sequence
```

```
<220> FEATURE:
<223> OTHER INFORMATION: Oligonucleotide designed to act as PCR primer
      for detection of p38 MAP kinase gene.

<400> SEQUENCE: 4
acccggtacc accaggtgct caggactcca tctct                           35

<210> SEQ ID NO 5
<211> LENGTH: 61
<212> TYPE: DNA
<213> ORGANISM: Artificial Sequence
<220> FEATURE:
<223> OTHER INFORMATION: Oligonucleotide designed to act as PCR primer
      for detection of MKK3 gene.

<400> SEQUENCE: 5
acaagaattc ataacatatg gctcatcatc atcatcatca ttccaagcca cccgcaccca   60
a                                                                  61

<210> SEQ ID NO 6
<211> LENGTH: 32
<212> TYPE: DNA
<213> ORGANISM: Artificial Sequence
<220> FEATURE:
<223> OTHER INFORMATION: Oligonucleotide designed to act as PCR primer
      for detectionof MKK3 gene.

<400> SEQUENCE: 6
tcccgtctag actatgagtc ttctcccagg at                              32

<210> SEQ ID NO 7
<211> LENGTH: 45
<212> TYPE: DNA
<213> ORGANISM: Artificial Sequence
<220> FEATURE:
<223> OTHER INFORMATION: Oligonucleotide designed to act as primer for
      mutation of MKK3 gene.

<400> SEQUENCE: 7
ggctacttgg tggacgaggt ggccaaggag atggatgccg gctgc                45

<210> SEQ ID NO 8
<211> LENGTH: 45
<212> TYPE: DNA
<213> ORGANISM: Artificial Sequence
<220> FEATURE:
<223> OTHER INFORMATION: Oligonucleotide designed to act as primer for
      mutation of MKK3 gene.

<400> SEQUENCE: 8
gcagccggca tccatctcct tggccacctc gtccaccaag tagcc                45
```

5-PYRIDYL-1,3-AZOLE COMPOUNDS, PROCESS FOR PRODUCING THE SAME AND USE THEREOF

This is a continuation of Ser. No. 09/959,356, filed Feb. 7, 2002, now U.S. Pat. No. 7,101,899, which is a U.S. national stage of International Application No. PCT/JP00/02575 filed Apr. 20, 2000.

TECHNICAL FIELD

The present invention relates to novel 5-pyridyl-1,3-azole compounds having an excellent medical action, particularly an adenosine $A_3$ receptor antagonistic activity, a p38 MAP kinase inhibitory action, a TNF-α production-inhibitory action and the like, a process for producing the same, a pharmaceutical composition and so on.

BACKGROUND ART

As a subtype of an adenosine receptor, $A_1$, $A_{2a}$, $A_{2b}$ and $A_3$ are known. Adenosine exhibits tracheostenotic action to an asthma patient and, on the other hand, theophylline which is an agent for treating asthma exhibits adenosine antagonism. In addition, it has been recently shown that the activation of $A_3$ receptor in a rat causes degranulation from mast cells (Journal of Biological Chemistry, vol. 268, 16887-16890, 1993), and that $A_3$ receptor is present on eosinophils in peripheral blood and its stimulation activates phospholipase C (PLC) to increase the intracellular calcium concentration (Blood, vol. 88, 3569-3574, 1996).

In addition, cytokines such as TNF-α (tumor necrosis factor-α), IL-1 (interleukin-1) and the like are biological substances which are produced by a variety of cells such as monocyte or macrophage in response to the infection and other cellular stress (Koj, A., Biochim. Biophys. Acta, 1317, 84-94 (1996)). Although these cytokines play an important role in the immune response when they are present at an appropriate amount, it is thought that the overproduction is associated with a variety of inflammatory diseases (Dinarello, C. A., Curr. Opin. Immunol., 3, 941-948 (1991)). p38 MAP kinase which was cloned as a homologue of MAP kinase is associated with the control of production of these cytokines and signal transduction system coupled with a receptor and there is a possibility that the inhibition of p38 MAP kinase becomes a drug for treating inflammatory diseases (Stein, B., Anderson, D., Annual Report in Medicinal Chemistry, edited by Bristol, J. A., Academic Press, vol. 31, pages 289-298, 1996).

Hitherto, as a compound exhibiting the selective antagonism for adenosine $A_3$ receptor, xanthine derivatives are reported in GB-A-2288733 and WO 95/11681 and the following compounds are reported in Journal of Medicinal Chemistry, vol. 40, 2596-2608, 1997:

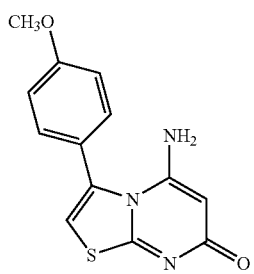

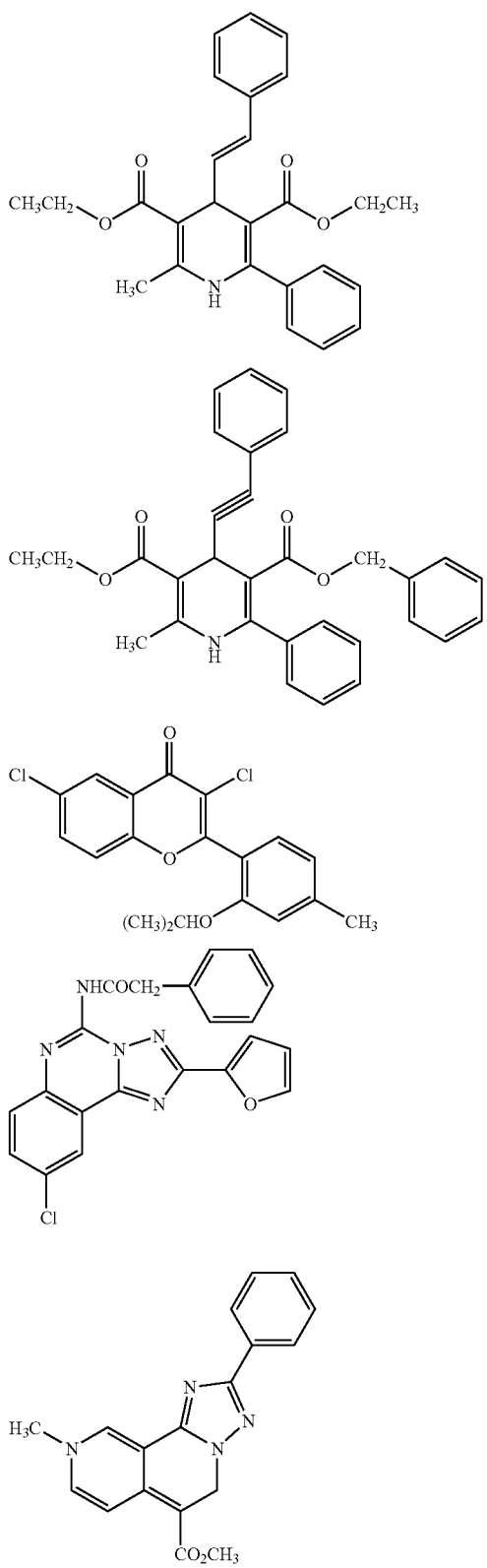

In addition, in WO 97/33879, there are described an adenosine $A_3$ receptor antagonistic agent containing a compound represented by the formula:

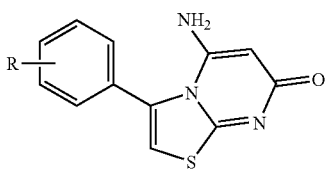

wherein R represents hydrogen, chlorine, bromine, fluorine, iodine, hydroxy, $C_{1-4}$ alkyl, $C_{1-4}$ alkoxy or $C_{1-4}$ alkylcarboxy, or a salt thereof and, more specifically, a compound

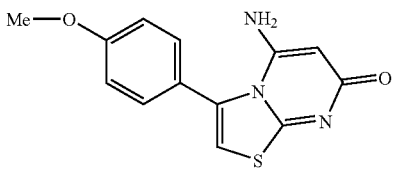

is described.

In addition, as a compound having a p38 MAP kinase inhibitory action, imidazole derivatives are described in JP-T 7-50317 (WO 93/14081) and oxazole derivatives are described in JP-T 9-505055 (WO 95/13067), respectively.

On the other hand, as thiazole compounds, the following compounds are known:

1) 1,3-thiazole derivatives represented by the formula:

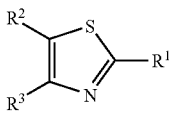

wherein $R^1$ represents a cycloalkyl group, a cyclic amino group, an amino group optionally having, as a substituent, 1 or 2 lower alkyl, phenyl, acetyl or lower alkoxycarbonylacetyl, an alkyl group optionally having, as a substituent, hydroxyl, carboxyl or lower alkoxycarbonyl, or a phenyl group optionally having, as a substituent, carboxyl, 2-carboxyethenyl or 2-carboxy-1-propenyl, $R^2$ represents a pyridyl group optionally having, as a substituent, lower alkyl, $R^3$ represents a phenyl group optionally having, as a substituent, lower alkoxy, lower alkyl, hydroxyl, halogen or methylenedioxy, or salts thereof, which have analgesic, antipyretic, anti-inflammatory, anti-ulcerative, thromboxane $A_2$ ($TXA_2$) synthesizing enzyme-inhibitory, and platelet coagulation-inhibitory activities (JP-A 60-58981), 2) 1,3-thiazole derivatives represented by the formula:

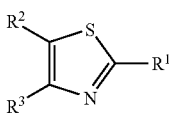

wherein $R^1$ represents an alkyl group, an alkenyl group, an aryl group, an aralkyl group, a cycloalkyl group, a heterocyclic group employing carbon as an attachment point or an amino group optionally having substituents, $R^2$ represents a pyridyl group optionally substituted with an alkyl group, $R^3$ represents a phenyl group optionally having substituents, or salts thereof, which have analgesic, antipyretic, anti-inflammatory, anti-ulcerative, $TXA_2$ synthesizing enzyme-inhibitory, and platelet coagulation-inhibitory activities (JP-A 61-10580), 3) 1,3-thiazole derivatives represented by the formula:

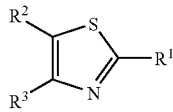

wherein $R^1$ represents an alkyl group, an alkenyl group, an aryl group, an aralkyl group, a cycloalkyl group, a heterocyclic group employing carbon as an attachment point or an amino group optionally having substituents, $R^2$ represents a pyridyl group optionally substituted with an alkyl group, $R^3$ represents an aryl group optionally having substituents, or salts thereof, which have analgesic, antipyretic, anti-inflammatory, anti-ulcerative, $TXA_2$ synthesizing enzyme-inhibitory, and platelet coagulation-inhibitory activities (U.S. Pat. No. 4,612,321), 4) imidazole derivatives represented by the formula:

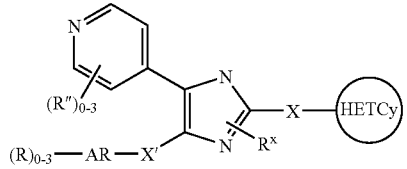

which have an anti-cancer activity and a cytokine inhibitory activity, more specifically, the following compounds are described (WO 97/12876):

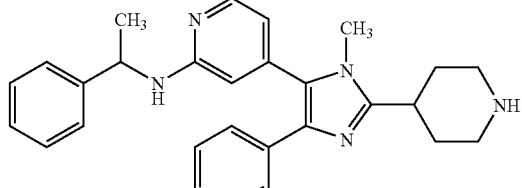

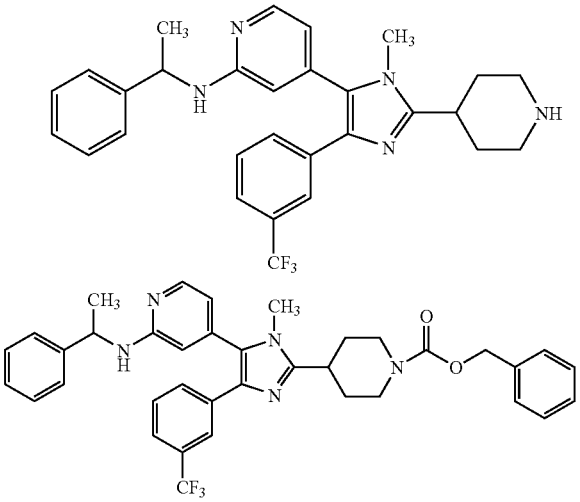

Since an adenosine $A_3$ antagonist, a p38 MAP kinase inhibiting agent and a TNF-α production-inhibiting agent having the satisfactory activity and effect, safety, (oral)

absorption, (metabolism) stability and the like have not been found, it is desired the development of the excellent adenosine A_3 receptor antagonist, the p38 MAP kinase-inhibiting agent and the TNF-α production-inhibiting agent as a pharmaceutical which are effective for preventing or treating adenosine A_3 receptor-related diseases, cytokine-mediated diseases and the like.

DISCLOSURE OF THE INVENTION

The present inventors studied variously and, as a result, first synthesized novel compounds which may be N-oxidized and which are represented by the formula (I):

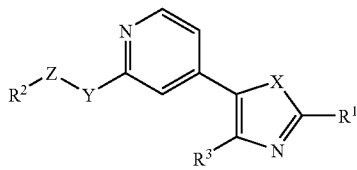

wherein $R^1$ represents a hydrogen atom, a hydrocarbon group optionally having substituents, a heterocyclic group optionally having substituents, an amino group optionally having substituents or an acyl group, $R^2$ represents an aromatic group optionally having substituents, $R^3$ represents a hydrogen atom, a pyridyl group optionally having substituents or an aromatic hydrocarbon group optionally having substituents, X represents an oxygen atom or an optionally oxidized sulfur atom, Y represents a bond, an oxygen atom, an optionally oxidized sulfur atom or a group represented by the formula: $NR^4$ (wherein $R^4$ represents a hydrogen atom, a hydrocarbon group optionally having substituents or an acyl group) and Z represents a bond or a divalent acyclic hydrocarbon group optionally having substituents, or a salt thereof [hereinafter, abbreviated as Compound (I) sometimes], which has a structural characteristics that a 5-position of a ring represented by the formula:

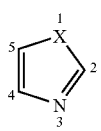

wherein X represents an oxygen atom or an optionally oxidized sulfur atom, is substituted with a 4-pyridyl group, and further it has a side chain having an aromatic group at 2-position of the pyridyl group, found that the resulting Compound (I) have unexpectedly excellent pharmaceutical activities such as a selective affinity for an adenosine A_3 receptor and an adenosine A_3 receptor antagonistic activity, a p38 MAP kinase inhibitory activity and the like based on the specific chemical structure, and that the compound has also excellent natures in the physical properties as a pharmaceutical such as stability and the like and is sufficiently satisfactory as a pharmaceutical, and completed the present invention based on these findings.

The present invention relates to (1) an optionally N-oxidized compound represented by the formula:

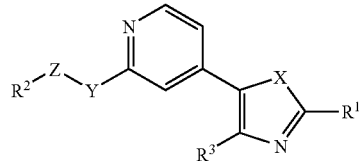

wherein $R^1$ represents a hydrogen atom, a hydrocarbon group optionally having substituents, a heterocyclic group optionally having substituents, an amino group optionally having substituents or an acyl group, $R^2$ represents an aromatic group optionally having substituents, $R^3$ represents a hydrogen atom, a pyridyl group optionally having substituents or an aromatic hydrocarbon group optionally having substituents, X represents an oxygen atom or an optionally oxidized sulfur atom, Y represents a bond, an oxygen atom, an optionally oxidized sulfur atom or a group represented by the formula: $NR^4$ (wherein $R^4$ represents a hydrogen atom, a hydrocarbon group optionally having substituents or an acyl group) and Z represents a bond or a divalent acyclic hydrocarbon group optionally having substituents, or a salt thereof, (2) the compound according to (1), wherein Z is a divalent acyclic hydrocarbon group optionally having substituents, (3) the compound according to (1), which is a compound represented by the formula:

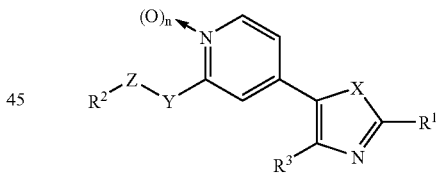

wherein n represents 0 or 1, and other symbols are as defined in (1), or a salt thereof, (4) the compound according to (1) or (3), wherein $R^1$ represents (i) a hydrogen atom, (ii) a $C_{1-6}$ alkyl group, a $C_{2-6}$ alkenyl group, a $C_{2-6}$ alkynyl group, a $C_{3-6}$ cycloalkyl group, a $C_{6-14}$ aryl group or a $C_{7-16}$ aralkyl group [these groups may have substituents selected from the group (substituent group A) consisting of oxo, halogen atom, $C_{1-3}$ alkylenedioxy, nitro, cyano, optionally halogenated $C_{1-6}$ alkyl, optionally halogenated $C_{2-6}$ alkenyl, carboxy $C_{2-6}$ alkenyl, optionally halogenated $C_{2-6}$ alkynyl, optionally halogenated $C_{3-6}$ cycloalkyl, $C_{6-14}$ aryl, optionally halogenated $C_{1-8}$ alkoxy, $C_{1-6}$ alkoxy-carbonyl-$C_{1-6}$ alkoxy, hydroxy, $C_{6-14}$ aryloxy, $C_{7-16}$ aralkyloxy, mercapto, optionally halogenated $C_{1-6}$ alkylthio, $C_{6-14}$ arylthio, $C_{7-16}$ aralkylthio, amino, mono-$C_{1-6}$ alkylamino, mono-$C_{6-14}$ arylamino, di-$C_{1-6}$ alkylamino, di-$C_{6-14}$ arylamino, formyl, carboxy, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, 5 or 6 membered heterocyclic carbonyl, carbamoyl, thiocarbamoyl, mono-$C_{1-6}$ alkyl-carbamoyl, di-$C_{1-6}$ alkyl-carbamoyl, $C_{6-14}$ aryl-carbamoyl, 5 or 6 membered heterocyclic carbamoyl, $C_{1-6}$ alkylsulfonyl, $C_{6-14}$ arylsulfonyl, $C_{1-6}$ alkylsulfinyl, $C_{6-14}$ arylsulfinyl, formylamino, $C_{1-6}$ alkyl-carbonylamino, $C_{6-14}$ aryl-carbonylamino, $C_{1-6}$ alkoxy-carbonylamino, $C_{1-6}$ alkylsulfonylamino, $C_{6-14}$ arylsulfonylamino, $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy, nicotinoyloxy, 5 to 7 membered saturated cyclic amino optionally having 1 to 4 heteroatoms of one or two kinds selected from a nitrogen atom, a sulfur atom and an oxygen atom in addition to one nitrogen atom and carbon atoms (this cyclic amino may have substituents selected from the group consisting of $C_{1-6}$ alkyl, $C_{6-14}$ aryl, $C_{1-6}$ alkyl-carbonyl, 5 to 10 membered aromatic heterocyclic group and oxo), 5 to 10 membered aromatic heterocyclic group containing 1 to 4 heteroatoms of one or two kinds selected from a nitrogen atom, a sulfur atom and an oxygen atom in addition to carbon atoms, sulfo, sulfamoyl, sulfinamoyl and sulfenamoyl]

(iii) a 5 to 14 membered heterocyclic group containing 1 to 4 heteroatoms of one or two kinds selected from a nitrogen atom, a sulfur atom and an oxygen atom in addition to carbon atoms optionally having substituents selected from the substituent group A, (iv) an acyl group represented by the formula:

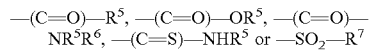

—(C=O)—$R^5$, —(C=O)—$OR^5$, —(C=O)—$NR^5R^6$, —(C=S)—$NHR^5$ or —$SO_2$—$R^7$ (wherein $R^5$ represents ① a hydrogen atom, ② a $C_{1-6}$ alkyl group, an $C_{2-6}$ alkenyl group, an $C_{2-6}$ alkynyl group, a $C_{3-6}$ cycloalkyl group, a $C_{6-14}$ aryl group or a $C_{7-16}$ aralkyl group optionally having substituents selected from the substituent group A or ③ a 5 to 14 membered heterocyclic group containing 1 to 4 heteroatoms of one or two kinds selected from a nitrogen atom, a sulfur atom and an oxygen atom in addition to carbon atoms optionally having substituents selected from the substituent group A, $R^6$ represents a hydrogen atom or a $C_{1-6}$ alkyl group, $R^7$ represents ① a $C_{1-6}$ alkyl group, a $C_{2-6}$ alkenyl group, a $C_{2-6}$ alkynyl group, a $C_{3-6}$ cycloalkyl group, a $C_{6-14}$ aryl group or a $C_{7-16}$ aralkyl group optionally having substituents selected from the substituent group A or ② a 5 to 14 membered heterocyclic group containing 1 to 4 heteroatoms of one or two kinds selected from a nitrogen atom, a sulfur atom and an oxygen atom in addition to carbon atoms optionally having substituents selected from the substituent group A), (v) an amino group (this amino group may have substituents selected from the group consisting of ① a $C_{1-6}$ alkyl group, a $C_{2-6}$ alkenyl group, a $C_{2-6}$ alkynyl group, a $C_{3-6}$ cycloalkyl group, a $C_{6-14}$ aryl group or a $C_{7-16}$ aralkyl group optionally having substituents selected from the substituent group A, ② a 5 to 14 membered heterocyclic group containing 1 to 4 heteroatoms of one or two kinds selected from a nitrogen atom, a sulfur atom and an oxygen atom in addition to carbon atoms optionally having substituents selected from the substituent group A, ③ an acyl group as defined in the (iv), and ④ a $C_{1-6}$ alkylidene group optionally having substituents selected from the substituent group A), or (vi) a 5 to 7 membered non-aromatic cyclic amino group optionally containing 1 to 4 heteroatoms of one or two kinds selected from a nitrogen atom, a sulfur atom and an oxygen atom in addition to one nitrogen atom and carbon atoms (this cyclic amino may have substituents selected from the group consisting of $C_{1-6}$ alkyl, $C_{6-14}$ aryl, $C_{1-6}$ alkyl-carbonyl, 5 to 10 membered aromatic heterocyclic group and oxo);

$R^2$ represents ① a $C_{6-14}$ monocyclic or fused polycyclic aromatic hydrocarbon group optionally having substituents selected from the substituent group A or ② a 5 to 14 membered aromatic heterocyclic group containing 1 to 4 heteroatoms of one or two kinds selected from a nitrogen atom, a sulfur atom and an oxygen atom in addition to carbon atoms, optionally having substituents selected from the substituent group A;

$R^3$ represents ① a hydrogen atom, ② a pyridyl group optionally having substituents selected from the substituent group A, or ③ a $C_{6-14}$ monocyclic or fused polycyclic aromatic hydrocarbon group optionally having substituents selected from the substituent group A;

X represents O, S, SO or $SO_2$;

Y represents a bond, O, S, SO, $SO_2$ or a group represented by the formula: $NR^4$ (wherein $R^4$ represents ① a hydrogen atom, ② a $C_{1-6}$ alkyl group, a $C_{2-6}$ alkenyl group, a $C_{2-6}$ alkynyl group, a $C_{3-6}$ cycloalkyl group, a $C_{6-14}$ aryl group or a $C_{7-16}$ aralkyl group optionally having substituents selected from the substituent group A or ③ an acyl group as defined in the (iv)), Z represents a bond, a $C_{1-15}$ alkylene group, a $C_{2-16}$ alkenylene group or a $C_{2-16}$ alkynylene group optionally having substituents selected from the substituent group A, (5) the compound according to (1), wherein $R^1$ is an amino group optionally having substituents, (6) the compound according to (1), wherein $R^1$ is (i) a $C_{1-6}$ alkyl group, (ii) a $C_{6-14}$ aryl group optionally substituted with substituents selected from $C_{1-6}$ alkylthio, $C_{1-6}$ alkylsulfonyl and halogen atom, or (iii) an amino group optionally having 1 or 2 acyl represented by the formula: —(C=O)—$R^{5'}$ (wherein $R^{5'}$ represents ① a $C_{1-6}$ alkyl group, ② a $C_{6-14}$ aryl group or ③ a 5 to 14 membered heterocyclic group containing 1 to 4 heteroatoms of one or two kinds selected from a nitrogen atom, a sulfur atom and an oxygen atom in addition to carbon atoms), (7) the compound according to (1), wherein $R^1$ is an amino group optionally having 1 or 2 acyl group represented by —(C=O)—$R^{5''}$ (wherein $R^{5''}$ represents ① a $C_{6-14}$ aryl group or ② a 5 to 14 membered heterocyclic group containing 1 to 4 heteroatoms of one or two kinds selected from a nitrogen atom, a sulfur atom and an oxygen atom in addition to carbon atoms), (8) the compound according to (1), wherein $R^2$ is a $C_{6-14}$ aryl group optionally having substituents, (9) the compound according to (1), wherein $R^2$ is a $C_{6-14}$ aryl group optionally substituted with halogen atom or $C_{1-6}$ alkoxy, or a 5 to 14 membered aromatic heterocyclic group containing 1 to 4 heteroatoms of one or two kinds selected from a nitrogen atom, a sulfur atom and an oxygen atom in addition to carbon atoms,

(10) the compound according to (1), wherein $R^2$ is a $C_{6-14}$ aryl group, or a 5 to 14 membered heterocyclic group containing 1 to 4 heteroatoms of one or two kinds selected from nitrogen atom, a sulfur atom and an oxygen atom in addition to carbon atoms,

(11) the compound according to (1), wherein $R^3$ is a $C_{6-14}$ aryl group optionally having substituents,

(12) the compound according to (1), wherein $R^3$ is a $C_{6-14}$ aryl group optionally substituted with one or two $C_{1-6}$ alkyl or $C_{1-6}$ alkoxy,

(13) the compound according to (1), wherein X is an optionally oxidized sulfur atom,

(14) the compound according to (1), wherein X is a sulfur atom,

(15) the compound according to (1), wherein Y is an oxygen atom or a group represented by the formula: $NR^4$ (wherein $R^4$ is as defined in (1)),

(16) the compound according to (1), wherein Y is an oxygen atom, an optionally oxidized sulfur atom or a group represented by the formula: $NR^{4'}$ (wherein $R^{4'}$ represents a $C_{1-6}$ alkyl group),

(17) the compound according to (1), wherein Y is O, NH or S,

(18) the compound according to (1), wherein Z is a lower alkylene group optionally having substituents,

(19) the compound according to (1), wherein Z is a bond or a $C_{1-6}$ alkylene group optionally having oxo,

(20) the compound according to (1), wherein $R^1$ is (i) a $C_{1-6}$ alkyl group, (ii) a $C_{6-14}$ aryl group optionally substituted with $C_{1-6}$ alkylthio, $C_{1-6}$ alkylsulfonyl and halogen atom, or (iii) an amino group optionally having 1 or 2 acyl group represented by the formula: —(C═O)—$R^{5'}$ (wherein $R^{5'}$ represents ① a $C_{1-6}$ alkyl group, ② a $C_{6-14}$ aryl group or ③ a 5 to 14 membered heterocyclic group containing 1 to 4 heteroatoms of one or two kinds selected from a nitrogen atom, a sulfur atom and an oxygen atom in addition to carbon atoms;

$R^2$ is a $C_{6-14}$ aryl group optionally substituted with halogen atom or $C_{1-6}$ alkoxy, or a 5 to 14 membered aromatic heterocyclic group containing 1 to 4 heteroatoms of one or two kinds selected from a nitrogen atom, a sulfur atom and an oxygen atom in addition to carbon atoms;

$R^3$ is a $C_{6-14}$ aryl group optionally substituted with 1 or 2 $C_{1-6}$ alkyl or $C_{1-6}$ alkoxy;

X is a sulfur atom;

Y is an oxygen atom, an optionally oxidized sulfur atom or a group represented by the formula: $NR^{4''}$ (wherein $R^{4''}$ represents a $C_{1-6}$ alkyl group);

Z is a $C_{1-6}$ alkylene group optionally having oxo or $C_{1-6}$ alkyl or a bond,

(21) the compound according to (1), wherein $R^1$ is an amino group optionally having 1 or 2 acyl represented by —(C═O)—$R^{5'''}$ (wherein $R^{5'''}$ represents ① a $C_{6-14}$ aryl group or ② a 5 to 14 membered heterocyclic group containing 1 to 4 heteroatoms of one or two kinds selected from a nitrogen atom, a sulfur atom and an oxygen atom in addition to carbon atoms);

$R^2$ is a $C_{6-14}$ aryl group or a 5 to 14 membered aromatic heterocyclic group containing 1 to 4 heteroatoms of one or two kinds selected from a nitrogen atom, a sulfur atom and an oxygen atom in addition to carbon atoms;

$R^3$ is a $C_{6-14}$ aryl group optionally substituted with 1 or 2 $C_{1-6}$ alkyl or $C_{1-6}$ alkoxy;

X is a sulfur atom; Y is O, NH or S; Z is a bond or a $C_{1-6}$ alkylene group optionally having oxo,

(22) N-[5-(2-benzoylamino-4-pyridyl)-4-(3,5-dimethylphenyl)-1,3-thiazol-2-yl]acetamide (Example Compound No. 9), N-[5-(2-benzylamino-4-pyridyl)-4-(3,5-dimethylphenyl)-1,3-thiazol-2-yl]acetamide (Example Compound No. 10), N-[4-[4-(4-methoxyphenyl)-2-methyl-1,3-thiazol-5-yl]-2-pyridyl]benzamide (Example Compound No. 13), N-[4-[2-(4-fluorophenyl)-4-(3-methylphenyl)-1,3-thiazol-5-yl]-2-pyridyl]phenylacetamide (Example Compound No. 14), N-[4-[2-ethyl-4-(3-methylphenyl)-1,3-thiazol-5-yl]-2-pyridyl]phenylacetamide (Example Compound No. 15-2), N-[4-[4-(3-methylphenyl)-2-propyl-1,3-thiazol-5-yl]-2-pyridyl]phenylacetamide (Example Compound No. 15-3), N-[4-[2-butyl-4-(3-methylphenyl)-1,3-thiazol-5-yl]-2-pyridyl]phenylacetamide (Example Compound No. 15-4), N-[4-[4-(3-methylphenyl)-2-(4-methylthiophenyl)-1,3-thiazol-5-yl]-2-pyridyl]phenylacetamide (Example Compound No. 15-6), N-[4-[2-ethyl-4-(3-methylphenyl)-1,3-thiazol-5-yl]-2-pyridyl]benzamide (Example Compound No. 16-1), N-[4-[2-ethyl-4-(3-methylphenyl)-1,3-thiazol-5-yl]-2-pyridyl]-3-phenylpropionamide (Example Compound No. 16-2), N-[4-[2-ethyl-4-(3-methylphenyl)-1,3-thiazol-5-yl]-2-pyridyl]-3-(4-methoxyphenyl)propionamide (Example Compound No. 16-3), N-[4-[2-ethyl-4-(3-methylphenyl)-1,3-thiazol-5-yl]-2-pyridyl-4-phenylbutyramide (Example Compound No. 16-5), N-[4-[4-(3-methylphenyl)-2-propyl-1,3-thiazol-5-yl]-2-pyridyl]benzamide (Example Compound No. 16-7), N-[4-[4-(3-methylphenyl)-2-propyl-1,3-thiazol-5-yl]-2-pyridyl]-3-phenylpropionamide (Example Compound No. 16-8), N-[4-[2-butyl-4-(3-methylphenyl)-1,3-thiazol-5-yl]-2-pyridyl]benzamide (Example Compound No. 16-9), N-[4-[2-butyl-4-(3-methylphenyl)-1,3-thiazol-5-yl]-2-pyridyl]-3-phenylpropionamide (Example Compound No. 16-10), N-[4-[2-(4-fluorophenyl)-4-(3-methylphenyl)-1,3-thiazol-5-yl]-2-pyridyl]benzamide (Example Compound No. 16-11), N-[4-[2-(4-fluorophenyl)-4-(3-methylphenyl)-1,3-thiazol-5-yl]-2-pyridyl]-3-phenylpropionamide (Example Compound No. 16-12), N-[4-[4-(3-methylphenyl)-2-(4-methylthiophenyl)-1,3-thiazol-5-yl]-2-pyridyl]benzamide (Example Compound No. 16-15), N-[4-[4-(3-methylphenyl)-2-(4-methylthiophenyl)-1,3-thiazol-5-yl]-2-pyridyl]-3-phenylpropionamide (Example Compound No. 16-16), N-benzyl-N-[4-[2-ethyl-4-(3-methylphenyl)-1,3-thiazol-5-yl]-2-pyridyl]amine (Example Compound No. 19-2), N-[4-[2-ethyl-4-(3-methylphenyl)-1,3-thiazol-5-yl]-2-pyridyl]-N-(2-phenylethyl)amine (Example Compound No. 19-3), N-[4-[2-ethyl-4-(3-methylphenyl)-1,3-thiazol-5-yl]-2-pyridyl]-N-(3-phenylpropyl)amine (Example Compound No. 19-4), N-benzyl-N-[4-[4-(3-methylphenyl)-2-propyl-1,3-thiazol-5-yl]-2-pyridyl]amine (Example Compound No. 19-5), N-[4-[4-(3-methylphenyl)-2-propyl-1,3-thiazol-5-yl]-2-pyridyl]-N-(2-phenylethyl)amine (Example Compound No. 19-6), N-[4-[4-(3-methylphenyl)-2-propyl-1,3-thiazol-5-yl]-2-pyridyl]-N-(3-phenylpropyl) amine (Example Compound No. 19-7), N-benzyl-N-[4-[2-butyl-4-(3-methylphenyl)-1,3-thiazol-5-yl]-2-pyridyl]amine (Example Compound No. 19-8), N-[4-[2-butyl-4-(3-methylphenyl)-1,3-thiazol-5-yl]-2-pyridyl]-N-(2-phenylethyl)amine (Example Compound No. 19-9), N-[4-[2-butyl-4-(3-methylphenyl)-1,3-thiazol-5-yl]-2-pyridyl]-N-(3-phenylpropyl)amine (Example Compound No. 19-10), N-benzyl-N-[4-[4-(3-methylphenyl)-2-(4-methylthiophenyl)-1,3-thiazol-5-yl]-2-pyridyl]amine (Example Compound No. 19-17), N-[4-[4-(3-methylphenyl)-2-(4-methylthiophenyl)-1,3-thiazol-5-yl]-2-pyridyl]-N-(2-phenylethyl)amine (Example Compound No. 19-18), N-[4-[4-(3-methylphenyl)-2-(4-methylthiophenyl)-1,3-thiazol-5-yl]-2-pyridyl]-N-(3-phenylpropyl)amine (Example Compound No. 19-19), N-[4-[4-(3-methylphenyl)-2-(4-methylsulfonylphenyl)-1,3-thiazol-5-yl]-2-pyridyl]benzamide (Example Compound No. 20), N-[4-[4-(3-methylphenyl)-2-(4-methylsulfonylphenyl)-1,3-thiazol-5-yl]-2-pyridyl]phenylacetamide (Example Compound No. 21-1), N-[4-[4-(3-methylphenyl)-2-(4-methylsulfonylphenyl)-1,3-thiazol-5-yl]-2-pyridyl]-3-phenylpropionamide (Example Compound No. 21-2), N-benzyl-N-[4-[4-(3-methylphenyl)-2-(4-methylsulfonylphenyl)-1,3-thiazol-5-yl]-2-pyridyl]amine (Example Compound No. 21-5), N-[4-[4-(3-methylphenyl)-2-(4-methylsulfonylphenyl)-1,3-thiazol-5-yl]-2-pyridyl]-N-(3-phenylpropyl]amine (Example Compound No. 21-6), N-[4-[4-(3-methylphenyl)-2-(4-methylsulfonylphenyl)-1,3-thiazol-5-yl]-2-pyridyl]-N-(2-phenylethyl)amine (Example Compound No. 25-1), N-(4-fluorobenzyl)-N-[4-[4-(3-methylphenyl)-2-(4-methylsulfonylphenyl)-1,3-thiazol-5-yl]-2-pyridyl]amine (Example Compound No. 25-2), or salts thereof,

(23) a prodrug of the compound according to (1),

(24) a process for producing the compound according to (1), which comprises:

reacting a compound represented by the formula:

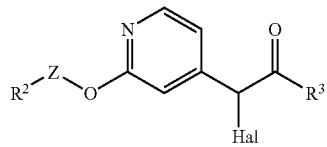

(VII)

wherein Hal represents a halogen atom, and other symbols are as defined as (1), or a salt thereof with a compound represented by the formula:

 (VIII)

wherein $R^1$ is as defined in (1), or a salt thereof, to obtain a compound represented by the formula:

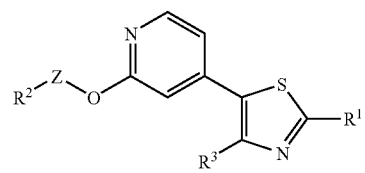

(Ia)

wherein each symbol is as defined in (1), or a salt thereof, or (ii) reacting a compound represented by the formula:

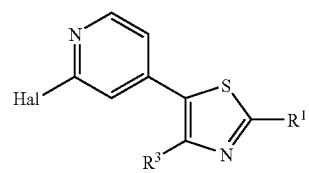

(X)

wherein Hal represents halogen atom, and other symbols are as defined as (1), or a salt thereof with a compound represented by the formula:

 (XI)

wherein each symbol is as defined in (1), or a salt thereof, to obtain a compound represented by the formula:

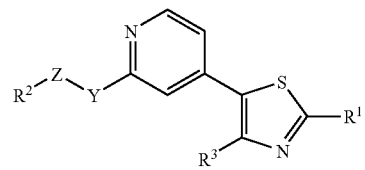

(Ib)

wherein each symbol is as defined in (1), or a salt thereof, or (iii) reacting a compound represented by the formula:

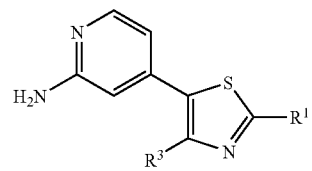

(XVII)

wherein each symbol is as defined in (1), or a salt thereof with a compound represented by the formula:

 (XVIII)

wherein L represents a leaving group, and other symbols are as defined in (1), or a salt thereof, to obtain a compound represented by the formula:

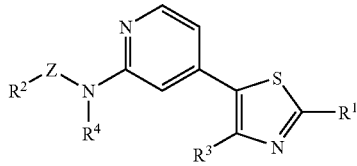

(Ic)

wherein each symbol is as defined in (1), or a salt thereof, or (iv) reacting a compound represented by the formula:

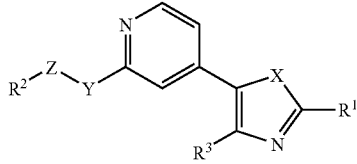

(I)

wherein each symbol is as defined in (1), or a salt thereof with peroxy acid, hydrogen peroxide or alkyl hydroperoxide, to obtain a compound represented by the formula:

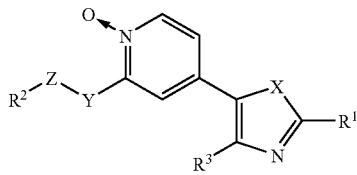

(Id)

wherein each symbol is as defined in (1), or a salt thereof,

(25) a pharmaceutical composition which comprises the compound according to (1) or a prodrug thereof,

(26) the composition according to (25), which is an adenosine $A_3$ receptor antagonist,

(27) the composition according to (25), which is an agent for preventing or treating adenosine $A_3$ receptor-related diseases,

(28) the composition according to (25), which is an agent for preventing or treating asthma or allergic diseases,

(29) the composition according to (25), which is an agent for preventing or treating brain edema, cerebrovascular disease or head trauma,

(30) the composition according to (25), which is an agent for inhibiting p38 MAP kinase,

(31) the composition according to (25), which is a TNF-α production-inhibiting agent,

(32) the composition according to (25), which is an agent for preventing or treating cytokine-mediated diseases,

(33) the composition according to (25), which is an agent for preventing or treating inflammation, Addison's disease, autoimmune hemolytic anemia, Crohn's disease, psoriasis, rheumatism, spinal trauma, brain edema, multiple sclerosis, Alzheimer's disease, Parkinson's syndrome, amyotrophic lateral sclerosis, diabetes, arthritis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, virus infection, atopic dermatitis, systemic lupus erythematosus, AIDS encephalopathy, meningitis, angina, cardiac infarction, congestive heart failure, hepatitis, transplantation, dialysis hypotension or disseminated intravascular coagulation,

(34) a method for antagonizing an adenosine $A_3$ receptor comprising administering an effective amount of an optionally N-oxidized compound represented by the formula:

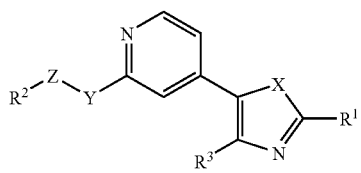

(I)

wherein $R^1$ represents a hydrogen atom, a hydrocarbon group optionally having substituents, a heterocyclic group optionally having substituents, an amino group optionally having substituents or an acyl group, $R^2$ represents an aromatic group optionally having substituents, $R^3$ represents a hydrogen atom, a pyridyl group optionally having substituents or an aromatic hydrocarbon group optionally having substituents, X represents an oxygen atom or an optionally oxidized sulfur atom, Y represents a bond, an oxygen atom, an optionally oxidized sulfur atom or a group represented by the formula: $NR^4$ (wherein $R^4$ represents a hydrogen atom, a hydrocarbon group optionally having substituents or an acyl group) and Z represents a bond or a divalent acyclic hydrocarbon group optionally having substituents, or a salt thereof or a prodrug thereof to mammals,

(35) a method for inhibiting p38 MAP kinase comprising administering an effective amount of an optionally N-oxidized compound represented by the formula:

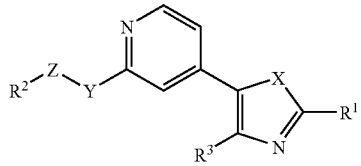

(I)

wherein $R^1$ represents a hydrogen atom, a hydrocarbon group optionally having substituents, a heterocyclic group optionally having substituents, an amino group optionally having substituents or an acyl group, $R^2$ represents an aromatic group optionally having substituents, $R^3$ represents a hydrogen atom, a pyridyl group optionally having substituents or an aromatic hydrocarbon group optionally having substituents, X represents an oxygen atom or an optionally oxidized sulfur atom, Y represents a bond, an oxygen atom, an optionally oxidized sulfur atom or a group represented by the formula: NR⁴ (wherein R⁴ represents a hydrogen atom, a hydrocarbon group optionally having substituents or an acyl group) and Z represents a bond or a divalent acyclic hydrocarbon group optionally having substituents, or a salt thereof or a prodrug thereof to mammals,

(36) a method for inhibiting TNF-α production comprising administering an effective amount of an optionally N-oxidized compound represented by the formula:

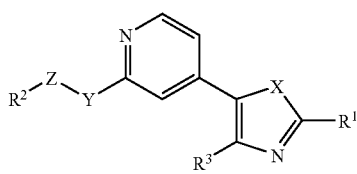

(I)

wherein R¹ represents a hydrogen atom, a hydrocarbon group optionally having substituents, a heterocyclic group optionally having substituents, an amino group optionally having substituents or an acyl group, R² represents an aromatic group optionally having substituents, R³ represents a hydrogen atom, a pyridyl group optionally having substituents or an aromatic hydrocarbon group optionally having substituents, X represents an oxygen atom or an optionally oxidized sulfur atom, Y represents a bond, an oxygen atom, an optionally oxidized sulfur atom or a group represented by the formula: NR⁴ (wherein R⁴ represents a hydrogen atom, a hydrocarbon group optionally having substituents or an acyl group) and Z represents a bond or a divalent acyclic hydrocarbon group optionally having substituents, or a salt thereof or a prodrug thereof to mammals,

(37) a method for preventing or treating asthma, allergic diseases, inflammation, Addison's disease, autoimmune hemolytic anemia, Crohn's disease, psoriasis, rheumatism, cerebral hemorrhage, cerebral infarction, head trauma, spinal trauma, brain edema, multiple sclerosis, Alzheimer's disease, Parkinson's syndrome, amyotrophic lateral sclerosis, diabetes, arthritis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, virus infection, atopic dermatitis, systemic lupus erythematosus, AIDS encephalopathy, meningitis, angina, cardiac infarction, congestive heart failure, hepatitis, transplantation, dialysis hypotension or disseminated intravascular coagulation comprising administering an effective amount of an optionally N-oxidized compound represented by the formula:

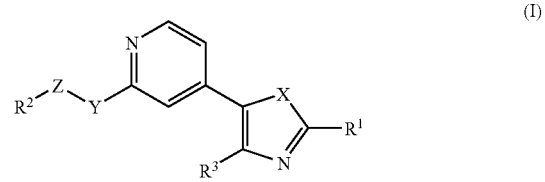

(I)

wherein R¹ represents a hydrogen atom, a hydrocarbon group optionally having substituents, a heterocyclic group optionally having substituents, an amino group optionally having substituents or an acyl group, R² represents an aromatic group optionally having substituents, R³ represents a hydrogen atom, a pyridyl group optionally having substituents or an aromatic hydrocarbon group optionally having substituents, X represents an oxygen atom or an optionally oxidized sulfur atom, Y represents a bond, an oxygen atom, an optionally oxidized sulfur atom or a group represented by the formula: NR⁴ (wherein R⁴ represents a hydrogen atom, a hydrocarbon group optionally having substituents or an acyl group) and Z represents a bond or a divalent acyclic hydrocarbon group optionally having substituents, or a salt thereof or a prodrug thereof to mammals,

(38) use of an optionally N-oxidized compound represented by the formula:

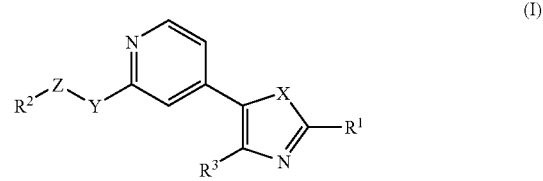

(I)

wherein R¹ represents a hydrogen atom, a hydrocarbon group optionally having substituents, a heterocyclic group optionally having substituents, an amino group optionally having substituents or an acyl group, R² represents an aromatic group optionally having substituents, R³ represents a hydrogen atom, a pyridyl group optionally having substituents or an aromatic hydrocarbon group optionally having substituents, X represents an oxygen atom or an optionally oxidized sulfur atom, Y represents a bond, an oxygen atom, an optionally oxidized sulfur atom or a group represented by the formula: NR⁴ (wherein R⁴ represents a hydrogen atom, a hydrocarbon group optionally having substituents or an acyl group) and Z represents a bond or a divalent acyclic hydrocarbon group optionally having substituents, or a salt thereof or a prodrug thereof for preparing an agent for antagonizing an adenosine $A_3$ receptor,

(39) use of an optionally N-oxidized compound represented by the formula:

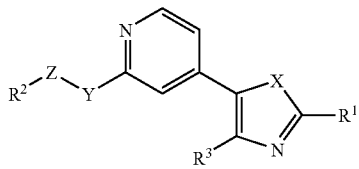

(I)

wherein $R^1$ represents a hydrogen atom, a hydrocarbon group optionally having substituents, a heterocyclic group optionally having substituents, an amino group optionally having substituents or an acyl group, $R^2$ represents an aromatic group optionally having substituents, $R^3$ represents a hydrogen atom, a pyridyl group optionally having substituents or an aromatic hydrocarbon group optionally having substituents, X represents an oxygen atom or an optionally oxidized sulfur atom, Y represents a bond, an oxygen atom, an optionally oxidized sulfur atom or a group represented by the formula: $NR^4$ (wherein $R^4$ represents a hydrogen atom, a hydrocarbon group optionally having substituents or an acyl group) and Z represents a bond or a divalent acyclic hydrocarbon group optionally having substituents, or a salt thereof or a prodrug thereof for preparing an agent for inhibiting p38 MAP kinase,

(40) use of an optionally N-oxidized compound represented by the formula:

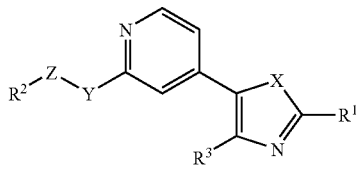

(I)

wherein $R^1$ represents a hydrogen atom, a hydrocarbon group optionally having substituents, a heterocyclic group optionally having substituents, an amino group optionally having substituents or an acyl group, $R^2$ represents an aromatic group optionally having substituents, $R^3$ represents a hydrogen atom, a pyridyl group optionally having substituents or an aromatic hydrocarbon group optionally having substituents, X represents an oxygen atom or an optionally oxidized sulfur atom, Y represents a bond, an oxygen atom, an optionally oxidized sulfur atom or a group represented by the formula: $NR^4$ (wherein $R^4$ represents a hydrogen atom, a hydrocarbon group optionally having substituents or an acyl group) and Z represents a bond or a divalent acyclic hydrocarbon group optionally having substituents, or a salt thereof or a prodrug thereof for preparing an agent for inhibiting a TNF-α production, and

(41) use of an optionally N-oxidized compound represented by the formula:

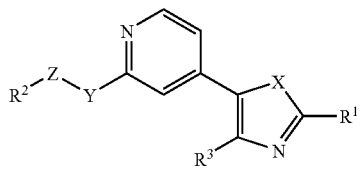

(I)

wherein $R^1$ represents a hydrogen atom, a hydrocarbon group optionally having substituents, a heterocyclic group optionally having substituents, an amino group optionally having substituents or an acyl group, $R^2$ represents an aromatic group optionally having substituents, $R^3$ represents a hydrogen atom, a pyridyl group optionally having substituents or an aromatic hydrocarbon group optionally having substituents, X represents an oxygen atom or an optionally oxidized sulfur atom, Y represents a bond, an oxygen atom, an optionally oxidized sulfur atom or a group represented by the formula: $NR^4$ (wherein $R^4$ represents a hydrogen atom, a hydrocarbon group optionally having substituents or an acyl group) and Z represents a bond or a divalent acyclic hydrocarbon group optionally having substituents, or a salt thereof or a prodrug thereof for preparing an agent for preventing or treating asthma, allergic diseases, inflammation, Addison's disease, autoimmune hemolytic anemia, Crohn's disease, psoriasis, rheumatism, cerebral hemorrhage, cerebral infarction, head trauma, spinal trauma, brain edema, multiple sclerosis, Alzheimer's disease, Parkinson's syndrome, amyotrophic lateral sclerosis, diabetes, arthritis, toxemia, Crohn's disease, ulcerative colitis, chronic pneumonia, silicosis, pulmonary sarcoidosis, pulmonary tuberculosis, cachexia, arteriosclerosis, Creutzfeldt-Jakob disease, virus infection, atopic dermatitis, systemic lupus erythematosus, AIDS encephalopathy, meningitis, angina, cardiac infarction, congestive heart failure, hepatitis, transplantation, dialysis hypotension or disseminated intravascular coagulation.

Furthermore, the present invention relates to

(42) the compound according to (1), wherein $R^1$ is an amino group optionally having one or two acyl groups represented by the formula: $-(C=O)-R^5$, $-(C=O)-OR^5$, $-(C=O)-NR^5R^6$, $-(C=S)-NHR^5$ or $-SO_2-R^7$ wherein each symbols are defined in (4),

(43) the compound according to (1), wherein $R^1$ is a $C_{1-6}$ alkyl group optionally having substituents,

(44) the compound according to (1), wherein $R^1$ is a $C_{6-14}$ aryl group optionally having a $C_{1-6}$ alkylsulfonyl group,

(45) the compound according to (7), wherein $R^{5''}$ is a phenyl group or a pyridyl group,

(46) the compound according to (1), wherein $R^2$ is a $C_{6-14}$ aryl group optionally having substituents or a 5 to 14 membered aromatic heterocyclic group containing 1 to 4 heteroatoms of one or two kinds selected from a nitrogen atom, a sulfur atom and an oxygen atom in addition to carbon atoms optionally having substituents,

(47) the compound according to (1), wherein $R^2$ is a phenyl group or a pyridyl group, and

(48) the compound according to (1), wherein $R^3$ is a phenyl group optionally substituted by one or two $C_{1-6}$ alkyl or $C_{1-6}$ alkoxy.

BEST MODE TO PRACTICE THE INVENTION

In the aforementioned formula, $R^1$ represents a hydrogen atom, a hydrocarbon group optionally having substituents, a heterocyclic group optionally having substituents, an amino group optionally having substituents or acyl group.

As "acyl group" represented by $R^1$, for example, there are an acyl group represented by the formula: —(C=O)—$R^5$, —(C=O)—$OR^5$, —(C=O)—$NR^5R^6$, —(C=S)—$NHR^5$ or —$SO_2$—$R^7$ (wherein $R^5$ represents a hydrogen atom, a hydrocarbon group optionally having substituents or a heterocyclic group optionally having substituents, $R^6$ represents a hydrogen atom or a $C_{1-6}$ alkyl, $R^7$ represents a hydrocarbon group optionally having substituents or a heterocyclic group optionally having substituents) and the like.

In the aforementioned formula, as "hydrocarbon group" of "hydrocarbon group optionally having substituents", for example, there are an acyclic or cyclic hydrocarbon group (for example, alkyl, alkenyl, alkynyl, cycloalkyl, aryl, aralkyl and the like) and the like. Among them, acyclic or cyclic hydrocarbon groups having carbon number of 1 to 16 are preferable.

As "alkyl", for example, $C_{1-6}$ alkyl (for example, methyl, ethyl, propyl, isopropyl, butyl, isobutyl, sec-butyl, tert-butyl, pentyl, hexyl and the like) is preferable and, in particular, $C_{1-3}$ alkyl (for example, methyl, ethyl, propyl and isopropyl) and the like are preferable.

As "alkenyl", for example, $C_{2-6}$ alkenyl (for example, vinyl, allyl, isopropenyl, 1-butenyl, 2-butenyl, 3-butenyl, 2-methyl-2-propenyl, 1-methyl-2-propenyl, 2-methyl-1-propenyl and the like) and the like are preferable.

As "alkynyl", for example, $C_{2-6}$ alkynyl (for example, ethynyl, propargyl, 1-butynyl, 2-butynyl, 3-butynyl, 1-hexynyl and the like) and the like are preferable.

As "cycloalkyl", for example, $C_{3-6}$ cycloalkyl (for example, cyclopropyl, cyclobutyl, cyclopentyl, cyclohexyl and the like) and the like are preferable.

As "aryl", for example, $C_{6-14}$ aryl (for example, phenyl, 1-naphthyl, 2-naphthyl, 2-biphenylyl, 3-biphenylyl, 4-biphenylyl, 2-anthryl and the like) and the like are preferable.

As "aralkyl", for example, $C_{7-16}$ aralkyl (for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl and the like) and the like are preferable.

As "substituents" of "hydrocarbon group optionally having substituents" represented by $R^5$, for example, there are oxo, halogen atom (for example, fluorine, chlorine, bromine, iodine and the like), $C_{1-3}$ alkylenedioxy (for example, methylenedioxy, ethylenedioxy and the like), nitro, cyano, optionally halogenated $C_{1-6}$ alkyl, optionally halogenated $C_{2-6}$ alkenyl, carboxy $C_{2-6}$ alkenyl (for example, 2-carboxyethenyl, 2-carboxy-2-methylethenyl and the like), optionally halogenated $C_{2-6}$ alkynyl, optionally halogenated $C_{3-6}$ cycloalkyl, $C_{6-14}$ aryl (for example, phenyl, 1-naphthyl, 2-naphthyl, 2-biphenylyl, 3-biphenylyl, 4-biphenylyl, 2-anthryl and the like), optionally halogenated $C_{1-8}$ alkoxy, $C_{1-6}$ alkoxy-carbonyl-$C_{1-6}$ alkoxy (for example, ethoxycarbonylmethyloxy and the like), hydroxy, $C_{6-14}$ aryloxy (for example, phenyloxy, 1-naphthyloxy, 2-naphthyloxy and the like), $C_{7-16}$ aralkyloxy (for example, benzyloxy, phenethyloxy and the like), mercapto, optionally halogenated $C_{1-6}$ alkylthio, $C_{6-14}$ arylthio (for example, phenylthio, 1-naphthylthio, 2-naphthylthio and the like), $C_{7-16}$ aralkylthio (for example, benzylthio, phenethylthio and the like), amino, mono-$C_{1-6}$ alkylamino (for example, methylamino, ethylamino and the like), mono-$C_{6-14}$ arylamino (for example, phenylamino, 1-naphthylamino, 2-naphthylamino and the like), di-$C_{1-6}$ alkylamino (for example, dimethylamino, diethylamino, ethylmethylamino and the like), di-$C_{6-14}$ arylamino (for example, diphenylamino and the like), formyl, carboxy, $C_{1-6}$ alkyl-carbonyl (for example, acetyl, propionyl and the like), $C_{3-6}$ cycloalkyl-carbonyl (for example, cyclopropylcarbonyl, cyclopentylcarbonyl, cyclohexylcarbonyl and the like), $C_{1-6}$ alkoxy-carbonyl (for example, methoxycarbonyl, ethoxycarbonyl, propoxycarbonyl, tert-butoxycarbonyl and the like), $C_{6-14}$ aryl-carbonyl (for example, benzoyl, 1-naphthoyl, 2-naphthoyl and the like), $C_{7-16}$ aralkyl-carbonyl (for example, phenylacetyl, 3-phenylpropionyl and the like), $C_{6-14}$ aryloxy-carbonyl (for example, phenoxycarbonyl and the like), $C_{7-16}$ aralkyloxy-carbonyl (for example, benzyloxycarbonyl, phenethyloxycarbonyl and the like), 5 or 6 membered heterocyclic carbonyl (for example, nicotinoyl, isonicotinoyl, thenoyl, furoyl, morpholinocarbonyl, thiomorpholinocarbonyl, piperazin-1-ylcarbonyl, pyrrolidin-1-ylcarbonyl and the like), carbamoyl, thiocarbamoyl, mono-$C_{1-6}$ alkyl-carbamoyl (for example, methylcarbamoyl, ethylcarbamoyl and the like), di-$C_{1-6}$ alkyl-carbamoyl (for example, dimethylcarbamoyl, diethylcarbamoyl, ethylmethylcarbamoyl and the like), $C_{6-14}$ aryl-carbamoyl (for example, phenylcarbamoyl, 1-naphthylcarbamoyl, 2-naphthylcarbamoyl and the like), 5 or 6 membered heterocyclic carbamoyl (for example, 2-pyridylcarbamoyl, 3-pyridylcarbamoyl, 4-pyridylcarbamoyl, 2-thienylcarbamoyl, 3-thienylcarbamoyl and the like), $C_{1-6}$ alkylsulfonyl (for example, methylsulfonyl, ethylsulfonyl and the like), $C_{6-14}$ arylsulfonyl (for example, phenylsulfonyl, 1-naphthylsulfonyl, 2-naphthylsulfonyl and the like), $C_{1-6}$ alkylsulfinyl (for example, methylsulfinyl, ethylsulfinyl and the like), $C_{6-14}$ arylsulfinyl (for example, phenylsulfinyl, 1-naphthylsulfinyl, 2-naphthylsulfinyl and the like), formylamino, $C_{1-6}$ alkyl-carbonylamino (for example, acetylamino and the like), $C_{6-14}$ aryl-carbonylamino (for example, benzoylamino, naphthoylamino and the like), $C_{1-6}$ alkoxy-carbonylamino (for example, methoxycarbonylamino, ethoxycarbonylamino, propoxycarbonylamino, butoxycarbonylamino and the like), $C_{1-6}$ alkylsulfonylamino (for example, methylsulfonylamino, ethylsulfonylamino and the like), $C_{6-14}$ arylsulfonylamino (for example, phenylsulfonylamino, 2-naphthylsulfonylamino, 1-naphthylsulfonylamino and the like), $C_{1-6}$ alkyl-carbonyloxy (for example, acetoxy, propionyloxy and the like), $C_{6-14}$ aryl-carbonyloxy (for example, benzoyloxy, naphthylcarbonyloxy and the like), $C_{1-6}$ alkoxy-carbonyloxy (for example, methoxycarbonyloxy, ethoxycarbonyloxy, propoxycarbonyloxy, butoxycarbonyloxy and the like), mono-$C_{1-6}$ alkyl-carbamoyloxy (for example, methylcarbamoyloxy, ethylcarbamoyloxy and the like), di-$C_{1-6}$ alkyl-carbamoyloxy (for example, dimethylcarbamoyloxy, diethylcarbamoyloxy and the like), $C_{6-14}$ aryl-carbamoyloxy (for example, phenylcarbamoyloxy, naphthylcarbamoyloxy and the like), nicotinoyloxy, 5 to 7 membered saturated cyclic amino optionally having substituents, 5 to 10 membered aromatic heterocyclic group (for example, 2-thienyl, 3-thienyl, 2-pyridyl, 3-pyridyl, b 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like), sulfo, sulfamoyl, sulfinamoyl, sulfenamoyl and the like.

The "hydrocarbon group" may have 1 to 5, preferably 1 to 3 aforementioned substituents at a substitutable position and, when the number of substituents is 2 or more, respective substituents may be the same or different.

As aforementioned "optionally halogenated $C_{1-6}$ alkyl", for example, there are $C_{1-6}$ alkyl (for example, methyl, ethyl, propyl, isopropyl, butyl, isobutyl, sec-butyl, tert-butyl, pentyl, hexyl and the like) and the like optionally having 1 to 5, preferably 1 to 3 halogen atoms (for example, fluorine, chlorine, bromine, iodine and the like). Examples thereof are methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like.

As the aforementioned "optionally halogenated $C_{2-6}$ alkenyl", for example, there are $C_{2-6}$ alkenyl (for example, vinyl, propenyl, isopropenyl, 2-buten-1-yl, 4-penten-1-yl, 5-hexen-1-yl) and the like optionally having 1 to 5, preferably 1 to 3 halogen atoms (for example, fluorine, chlorine, bromine, iodine and the like).

As the aforementioned "optionally halogenated $C_{2-6}$ alkynyl", there are $C_{2-6}$ alkynyl (for example, 2-butyn-1-yl, 4-pentyn-1-yl, 5-hexyn-1-yl and the like) and the like optionally having 1 to 5, preferably 1 to 3 halogen atoms (for example, fluorine, chlorine, bromine, iodine and the like).

As the aforementioned "optionally halogenated $C_{3-6}$ cycloalkyl", for example, there are $C_{3-6}$ cycloalkyl (for example, cyclopropyl, cyclobutyl, cyclopentyl, cyclohexyl and the like) and the like optionally having 1 to 5, preferably 1 to 3 halogen atoms (for example, fluorine, chlorine, bromine, iodine and the like). Examples thereof are cyclopropyl, cyclobutyl, cyclopentyl, cyclohexyl, 4,4-dichlorocyclohexyl, 2,2,3,3-tetrafluorocyclopentyl, 4-chlorocyclohexyl and the like.

As the aforementioned "optionally halogenated $C_{1-8}$ alkoxyl", for example, there are $C_{1-8}$ alkoxy (for example, methoxy, ethoxy, propoxy, isopropoxy, butoxy, isobutoxy, sec-butoxy, pentyloxy, hexyloxy and the like) and the like optionally having 1 to 5, preferably 1 to 3 halogen atoms (for example, fluorine, chlorine, bromine, iodine and the like). Examples thereof are methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy and the like.

As the aforementioned "optionally halogenated $C_{1-6}$ alkylthio", for example, there are $C_{1-6}$ alkylthio (for example, methylthio, ethylthio, propylthio, isopropylthio, butylthio, sec-butylthio, tert-butylthio and the like) and the like optionally having 1 to 5, preferably 1 to 3 halogen atoms (for example, fluorine, chlorine, bromine, iodine and the like). Examples thereof are methylthio, difluoromethylthio, trifluoromethylthio, ethylthio, propylthio, isopropylthio, butylthio, 4,4,4-trifluorobutylthio, pentylthio, hexylthio and the like.

As "5 to 7 membered saturated cyclic amino" of the aforementioned "5 to 7 membered saturated cyclic amino optionally having substituents", there are 5 to 7 membered saturated cyclic amino optionally containing 1 to 4 heteroatoms of one or two kinds selected from a nitrogen atom, a sulfur atom and an oxygen atom in addition to one nitrogen atom and carbon atoms and examples thereof are pyrolidin-1-yl, piperidino, piperazin-1-yl, morpholino, thiomorpholino, hexahydroazepin-1-yl and the like.

As "substituents" of the "5 to 7 membered saturated cyclic amino optionally having substituents", for example, there are 1 to 3 $C_{1-6}$ alkyl (for example, methyl, ethyl, propyl, isopropyl, butyl, isobutyl, sec-butyl, tert-butyl, pentyl, hexyl and the like), $C_{6-14}$ aryl (for example, phenyl, 1-naphthyl, 2-naphthyl, 2-biphenylyl, 3-biphenylyl, 4-biphenylyl, 2-anthryl and the like), $C_{1-6}$ alkyl-carbonyl (for example, acetyl, propionyl and the like), 5 to 10 membered aromatic heterocyclic group (for example, 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like), oxo and the like.

As "heterocyclic group" of "heterocyclic group optionally having substituents" represented by $R^5$, for example, there is a monovalent group obtained by removing one arbitrary hydrogen atom from a 5 to 14 membered (monocyclic, bicyclic or tricyclic) heterocycle containing 1 to 4 heteroatoms of one or two kinds selected from a nitrogen atom, a sulfur atom and an oxygen atom in addition to carbon atoms, preferably (i) a 5 to 14 membered (preferably 5 to 10 membered, particularly preferably 5 to 6 membered) aromatic heterocycle, (ii) a 5 to 10 membered (preferably 5 to 6 membered) non-aromatic heterocycle or (iii) a 7 to 10 membered bridged heterocycle.

As the aforementioned "5 to 14 membered (preferably 5 to 10 membered) aromatic heterocycle", there are an aromatic heterocycle such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine and the like, and a ring formed by fusing these rings (preferably monocyclic) with 1 or a plurality (preferably 1 to 2) of aromatic rings (for example, benzene ring and the like).

As the aforementioned "5 to 10 membered non-aromatic heterocycle", for example, there are pyrrolidine, imidazoline, pyrazolidine, pyrazoline, piperidine, piperazine, morpholine, thiomorpholine, dioxazole, oxadiazoline, thiadiazoline, triazoline, thiadiazole, dithiazole and the like.

As the aforementioned "7 to 10 membered bridged heterocycle", for example, there are quinuclidine, 7-azabicyclo [2.2.1]heptane and the like.

The "heterocyclic group" is preferably a 5 to 14 membered (preferably 5 to 10 membered) (monocyclic or bicyclic) heterocyclic group containing preferably 1 to 4 heteroatoms of one or two kinds selected from a nitrogen atom, a sulfur atom and an oxygen atom in addition to carbon atoms. More particularly, examples thereof are an aromatic heterocyclic group such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like, and a non-aromatic heterocyclic group such as 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like.

Among them, for example, a 5 or 6 membered heterocyclic group containing 1 to 3 heteroatoms selected from a nitrogen atom, a sulfur atom and an oxygen atom in addition to carbon atoms is further preferable. More particularly, examples thereof are 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino and the like.

As "substituents" of "heterocyclic group optionally having substituents", for example, there are the same "substituents" as substituents of "hydrocarbon group optionally having substituents" represented by $R^5$.

The "heterocyclic group" may have 1 to 5, preferably 1 to 3 aforementioned substituents at a substitutable position and, when the number of substituents is 2 or more, respective substituents may be the same or different.

As "$C_{1-6}$ alkyl" represented by $R^6$, for example, there are methyl, ethyl, propyl, isopropyl, butyl, isobutyl, sec-butyl, tert-butyl, pentyl, hexyl and the like.

As "hydrocarbon group optionally having substituents" and "heterocyclic group optionally having substituents" represented by $R^7$, for example, there are the aforementioned "hydrocarbon group optionally having substituents" and "heterocyclic group optionally having substituents" represented by $R^5$, respectively.

As "hydrocarbon group optionally having substituents" and "heterocyclic group optionally having substituents" represented by $R^1$, for example, there are the aforementioned "hydrocarbon group optionally having substituents" and "heterocyclic group optionally having substituents" represented by $R^5$, respectively.

As "amino group optionally having substituents" represented by $R^1$, for example, there are (1) an amino group optionally having 1 or 2 substituents and (2) a cyclic amino group optionally having substituents and the like.

As "substituents" of "amino group optionally having 1 or 2 substituents" of the aforementioned (1), for example, there are a hydrocarbon group optionally having substituents, a heterocyclic group optionally having substituents, an acyl group, an alkylidene group optionally having substituents and the like. As these "hydrocarbon group optionally having substituents" and "heterocyclic group optionally having substituents", there are the same "hydrocarbon group optionally having substituents" and "heterocyclic group optionally having substituents" as those represented by $R^5$ described above, respectively. As the "acyl group", there is the same "acyl group" as that by represented by $R^1$ as described above.

As "alkylidene group" of "alkylidene group optionally having substituents", for example, there are a $C_{1-6}$ alkylidene group (for example, methylidene, ethylidene, propylidene and the like) and the like. As "substituents" of "alkylidene group optionally having substituents", there are 1 to 5, preferably 1 to 3 same substituents as "substituents" of "hydrocarbon group optionally having substituents" represented by $R^5$.

When the number of the aforementioned "substituents" of "amino group optionally having 1 or 2 substituents" is 2, respective substituents may be the same or different.

As "cyclic amino group" of "cyclic amino group optionally having substituents" of the aforementioned (2), there are a 5 to 7 membered non-aromatic cyclic amino group optionally containing 1 to 4 heteroatoms of one or two kinds selected from a nitrogen atom, a sulfur atom and an oxygen atom in addition to one nitrogen atom and carbon atoms. More particularly, examples thereof are pyrrolidin-1-yl, piperidino, piperazin-1-yl, morpholino, thiomorpholino, hexahydroazepin-1-yl, imidazolidin-1-yl, 2,3-dihydro-1H-imidazol-1-yl, tetrahydro-1(2H)-pyrimidinyl, 3,6-dihydro-1(2H)-pyrimidinyl, 3,4-dihydro-1(2H)-pyrimidinyl and the like. As "substituents" of "cyclic amino optionally having substituents", there are 1 to 3 same ones as "substituents" of "5 to 7 membered saturated cyclic amino group" which were described in detail as "substituents" of "hydrocarbon group optionally having substituents" represented by $R^5$.

Examples of the 5 to 7 membered non-aromatic cyclic amino group having 1 oxo, there are 2-oxoimidazolidin-1-yl, 2-oxo-2,3-dihydro-1H-imidazol-1-yl, 2-oxotetrahydro-1(2H)-pyrimidinyl, 2-oxo-3,6-dihydro-1(2H)-pyrimidinyl, 2-oxo-3,4-dihydro-1(2H)-pyrimidinyl, 2-oxopyrrolidin-1-yl, 2-oxopiperidino, 2-oxopiperazin-1-yl, 3-oxopiperazin-1-yl, 2-oxo-2,3,4,5,6,7-hexahydroazepin-1-yl and the like.

As $R^1$, an amino group optionally having substituents, an aryl group optionally having substituents and an alkyl group optionally having substituents and the like are preferable.

As further preferable example of the "amino group optionally having substituents" is an amino group optionally having 1 or 2 acyl represented by the formula: —(C=O)—$R^5$, —(C=O)—$OR^5$, —(C=O)—$NR^5R^6$, —(C=S)—$NHR^5$ or —$SO_2$—$R^7$ [wherein respective symbols represent the same meanings as described above]. Particularly preferable example is an amino group optionally having 1 or 2 acyl represented by the formula: —C(C=O)—$R^5$ or —(C=O)—$NR^5R^6$ [wherein respective symbols represent the same meanings as described above].

As the "aryl group optionally having substituents", for example, there is preferably a $C_{6-14}$ aryl group (preferably a phenyl group and the like) optionally having 1 to 5 substituents selected from $C_{1-6}$ alkylthio, $C_{6-14}$ arylthio, $C_{1-6}$ alkylsulfinyl, $C_{6-14}$ arylsulfinyl, $C_{1-6}$ alkylsulfonyl, $C_{6-14}$ arylsulfonyl and carboxy.

As the "alkyl group optionally having substituents", for example, a $C_{1-6}$ alkyl group (for example, methyl, ethyl, propyl, isopropyl, butyl, isobutyl, sec-butyl, tert-butyl and the like) optionally substituted with 1 to 3 substituents selected from halogen atom, $C_{1-6}$ alkoxy, hydroxy, carboxy and $C_{1-6}$ alkoxy-carbonyl and the like are preferable, and particularly $C_{1-3}$ alkyl group such as methyl, ethyl and the like is preferable.

Among them, as $R^1$, (i) $C_{1-6}$ alkyl group (for example, $C_{1-4}$ alkyl group such as methyl, ethyl, propyl, butyl), (ii) a $C_{6-14}$ aryl group (for example, a phenyl group) optionally substituted with substituents selected from $C_{1-6}$ alkylthio (for example, methylthio), $C_{1-6}$ alkylsulfonyl (for example, methylsulfonyl) and halogen atom (for example, chlorine atom, fluorine atom) or (iii) an amino group optionally having 1 or 2 acyl represented by the formula: —(C=O)—$R^{5'}$ (wherein $R^{5'}$ represents ① a $C_{1-6}$ alkyl group (for example, $C_{1-3}$ alkyl group such as methyl), ② a $C_{6-14}$ aryl group (for example, a phenyl group) or ③ a 5 to 14 membered heterocyclic group containing 1 to 4 heteroatoms of one or two kinds selected from a nitrogen atom, a sulfur atom and an oxygen atom in addition to carbon atoms (for example, a 5 to 6 membered heterocyclic group containing 1 to 2 heteroatoms selected from a nitrogen atom, a sulfur atom and an oxygen atom in addition to carbon atoms such as pyridyl group) are preferable. As $R^{5'}$ and $R^{5'''}$, a phenyl group or a pyridyl group is suitable.

In the aforementioned formula, $R^2$ represents an aromatic group optionally having substituents.

As "aromatic group" of "aromatic group optionally having substituents" represented by $R^2$, for example, there are an aromatic hydrocarbon group, an aromatic heterocyclic group and the like.

As the "aromatic hydrocarbon group", examples thereof include a $C_{6-14}$ monocyclic or fused polycyclic (bicyclic or tricyclic) aromatic hydrocarbon group, etc. As examples, there are a $C_{6-14}$ aryl group and the like such as phenyl, 1-naphthyl, 2-naphthyl, 2-biphenylyl, 3-biphenylyl, 4-biphenylyl, 2-anthryl and the like and, further preferably, a $C_{6-10}$ aryl group and the like (for example, phenyl, 1-naphthyl, 2-naphthyl and the like, preferably phenyl and the like).

As the "aromatic heterocyclic group", there is a monovalent group obtained by removing one arbitrary hydrogen atom from 5 to 14 membered (preferably 5 to 10 membered) aromatic heterocycle containing 1 to 4 heteroatoms of one or two kinds selected from nitrogen atom, sulfur atom and oxygen atom in addition to carbon atoms.

As the aforementioned "5 to 14 membered (preferably 5 to 10 membered) aromatic heterocycle", for example, there are an aromatic heterocycle such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine and the like, and a ring formed by fusing these rings (preferably monocycle) with 1 or a plurality of (preferably 1 or 2) aromatic rings (for example, benzene ring and the like).

As the "aromatic heterocyclic group", there are preferably a 5 to 14 membered (preferably 5 to 10 membered)(monocyclic or bicyclic) aromatic heterocyclic group containing preferably 1 to 4 heteroatoms of one or two kinds selected from a nitrogen atom, a sulfur atom and an oxygen atom in addition to carbon atoms and the like and, more particularly, there are an aromatic heterocyclic group such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl and the like.

As "substituents" of "aromatic group optionally having substituents", there are 1 to 5, preferably 1 to 3 same substituents as "substituents" of "hydrocarbon group optionally having substituents" represented by $R^5$. When the number of substituents is 2 or more, respective substituents may be the same or different.

As $R^2$, (1) a $C_{6-14}$ aryl group optionally having substituents and (2) a 5 to 14 membered aromatic heterocyclic group containing 1 to 4 heteroatoms of one or two kinds selected from a nitrogen atom, a sulfur atom and an oxygen atom in addition to carbon atoms are preferable and, among them, (1) a $C_{6-14}$ aryl group (for example, phenyl group, naphthyl group) optionally substituted with halogen atom (for example, chlorine atom, fluorine atom) or $C_{1-6}$ alkoxy (for example, methoxy), (2) a 5 to 14 membered aromatic heterocyclic group containing 1 to 4 heteroatoms of one or two kinds selected from a nitrogen atom, a sulfur atom and an oxygen atom in addition to carbon atoms (for example, a 5 to 6 membered aromatic heterocyclic group containing 1 to 2 heteroatoms selected from a nitrogen atom, a sulfur atom and an oxygen atom in addition to carbon atoms such as pyridyl group, thienyl group) and the like are preferable and, in particular, a phenyl group, a pyridyl group and the like are suitable.

In the aforementioned formula, $R^3$ represents a hydrogen atom, a pyridyl group optionally having substituents or an aromatic hydrocarbon group optionally having substituents.

As "substituents" of "pyridyl group optionally having substituents" represented by $R^3$, there are the same substituents as "substituents" of "hydrocarbon group optionally having substituents" represented by $R^5$.

The "pyridyl group" may, for example, have 1 to 5, preferably 1 to 3 aforementioned substituents at substitutable positions and, when the number of substituents is 2 or more, respective substituents may be the same or different. In addition, an intracyclic nitrogen atom may be N-oxidized.

As "aromatic hydrocarbon group" of "aromatic hydrocarbon group optionally having substituents" represented by $R^3$, there is the same aromatic hydrocarbon group as "aromatic hydrocarbon group" of "aromatic group optionally having substituents" represented by $R^2$ and, preferably, there are a $C_{6-14}$ aryl group and the like such as phenyl, 1-naphthyl, 2-naphthyl, 2-biphenylyl, 3-biphenylyl, 4-biphenylyl, 2-anthryl and the like and, further preferably, a $C_{6-10}$ aryl group and the like (for example, phenyl, 1-naphthyl, 2-naphthyl and the like, preferably phenyl and the like) and the like. As "substituents" of "aromatic hydrocarbon group optionally having substituents" represented by $R_3$, there are the same substituents as substituents of "aromatic group optionally having substituents" represented by $R_2$.

As $R^3$, a $C_{6-14}$ aryl group optionally having substituents is preferable and, among them, a $C_{6-14}$ aryl group optionally substituted with 1 or 2 $C_{1-6}$ alkyl (for example, methyl, ethyl and the like) or $C_{1-6}$ alkoxy (for example, methoxy, ethoxy and the like) is preferable and, in particular, a phenyl group optionally substituted with 1 or 2 $C_{1-6}$ alkyl or $C_{1-6}$ alkoxy (for example, 3-methoxyphenyl, 2-methylphenyl, 2,4-dimethylphenyl and the like) is suitable.

In the aforementioned formula, X represents an oxygen atom or an optionally oxidized sulfur atom.

As "optionally oxidized sulfur atom" represented by X, there are S, SO and $SO_2$.

As X, there is preferably an optionally oxidized sulfur atom. Further preferably, it is S.

In the aforementioned formula, Y represents a bond, an oxygen atom, an optionally oxidized sulfur atom or the formula $NR^4$ (wherein $R^4$ represents a hydrogen atom, a hydrocarbon group optionally having substituents or an acyl group).

As "optionally oxidized sulfur atom" represented by Y, there are S, SO and $SO_2$.

As "hydrocarbon group optionally having substituents" represented by $R^4$, for example, there is the same group as "hydrocarbon group optionally having substituents" represented by $R^5$. Among them, a $C_{1-6}$ alkyl group such as methyl, ethyl and the like and, in particular, a $C_{1-3}$ alkyl group such as methyl and the like is preferable.

As "acyl group" represented by $R^4$, there is the same group as "acyl group" represented by $R^1$.

As Y, an oxygen atom, an optionally oxidized sulfur atom, a group represented by the formula $NR^4$ (wherein $R^4$ represents the same meaning as that described above) and the like are preferable and, among them, an oxygen atom, an optionally oxidized sulfur atom, a group represented by the formula $NR^{4'}$ ($R^{4'}$ represents a hydrogen atom or a $C_{1-6}$ alkyl group) and the like are preferable and, further, an oxygen atom, S, $SO_2$, NH, $N(CH_3)$ and the like are preferable and, in particular, O or NH is suitable.

In the aforementioned formula, Z represents a bond or a divalent acyclic hydrocarbon group optionally having substituents.

As "divalent acyclic hydrocarbon group" of "divalent acyclic hydrocarbon group optionally having substituents", for example, there are a $C_{1-15}$ alkylene group (for example, methylene, ethylene, propylene, butylene, pentamethylene, hexamethylene, heptamethylene, octamethylene and the like, preferably a $C_{1-6}$ alkylene group and the like), a $C_{2-16}$ alkenylene group (for example, vinylene, propylene, 1-butenylene, 2-butenylene, 1-pentenylene, 2-pentenylene, 3-pentenylene and the like), a $C_{2-16}$ alkynylene group (ethynylene, propynylene, 1-butynylene, 2-butynylene, 1-pentynylene, 2-pentynylene, 3-pentynylene and the like) and the like, preferably, a $C_{1-15}$ alkylene group, particularly preferably, a $C_{1-6}$ alkylene group and the like. As "substituents" of "divalent acyclic hydrocarbon group optionally having substituents" represented by Z, for example, there are the same substituents as "substituents" of "hydrocarbon group optionally having substituents" represented by $R^5$.

As Z, a lower alkylene group optionally having $C_{1-3}$ alkyl (for example, methyl), oxo and the like (for example, a $C_{1-6}$ alkylene group such as methylene, ethylene, propylene and the like, in particular, a $C_{1-3}$ alkylene group) is preferable and, among them, a $C_{1-6}$ alkylene group optionally having oxo (for example, a $C_{1-3}$ alkylene group such as methylene, ethylene, propylene, in particular, methylene) is suitable.

More particularly, as Z, —$CH_2$—, —$(CH_2)_2$—, —$(CH_2)_3$—, —CO—, —$CH_2CO$—, —$(CH_2)_2CO$—, —CH($CH_3$)— and the like are used and, in particular, —$CH_2$—, —CO— and the like are suitable.

A nitrogen atom in Compound (I) may be N-oxidized. For example, a nitrogen atom which is a constituent atom of 4-pyridyl group as a substituent at 5-position of a ring represented by the formula:

wherein a symbol in the formula represents the same meaning as that described above, may be N-oxidized. As Compound (I), for example, a compound represented by the formula:

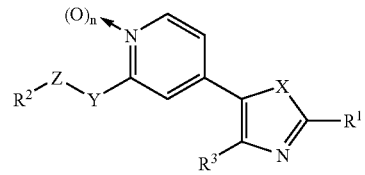

wherein n represents 0 or 1, and other symbols represents the same meanings as those described above, or salts thereof are preferable.

As Compound (I), compounds shown by the following (A) to (F) are preferably used.

(A) Compound (I) wherein $R^1$ is an amino group optionally having substituents, $R^2$ is a $C_{6-14}$ aryl group optionally having substituents, $R^3$ is a $C_{6-14}$ aryl group optionally having substituents, X is a sulfur atom, Y is an oxygen atom or a group represented by the formula $NR^4$ (wherein $R^4$ represents the same meaning as that described above) or (and) Z is a lower alkylene group optionally having substituents.

(B) Compound (I) wherein $R^1$ is (i) a $C_{1-6}$ alkyl group (for example, a $C_{1-4}$ alkyl group such as methyl, ethyl, propyl, butyl and the like), (ii) a $C_{6-14}$ aryl group (for example, a phenyl group) optionally substituted with substituents selected from $C_{1-6}$ alkylthio (for example, methylthio), $C_{1-6}$ alkylsulfonyl (for example, methylsulfonyl) and halogen atom (for example, chlorine atom, fluorine atom), or (iii) an amino group optionally having 1 or 2 acyl represented by the formula: —(C=O)—$R^{5'}$ [wherein $R^{5'}$ represents ① a $C_{1-6}$ alkyl group (for example, $C_{1-3}$ alkyl group such as methyl and the like), ② a $C_{6-14}$ aryl group (for example, a phenyl group) or ③ a 5 to 14 membered heterocyclic group containing 1 to 4 heteroatoms of one or two kinds selected from a nitrogen atom, a sulfur atom and an oxygen atom in addition to carbon atoms (for example, a 5 to 6 membered heterocyclic group containing 1 to 2 heteroatoms selected from a nitrogen atom, a sulfur atom and an oxygen atom in addition to carbon atoms such as a pyridyl group);

$R_2$ is a $C_{6-14}$ aryl group (for example, a phenyl group, a naphthyl group) optionally substituted with halogen atom (for example, chlorine atom, fluorine atom) or $C_{1-6}$ alkoxy (for example, methoxy), or a 5 to 14 membered aromatic heterocyclic group containing 1 to 4 heteroatoms of one or two kinds selected from a nitrogen atom, a sulfur atom and an oxygen atom in addition to carbon atoms (for example, a 5 to 6 membered aromatic heterocyclic group containing 1 to 2 heteroatoms selected from a nitrogen atom, a sulfur atom and an oxygen atom in addition to carbon atoms such as a pyridyl group, a thienyl group and the like);

$R^3$ is a $C_{6-14}$ aryl group (particularly, a phenyl group) optionally substituted with 1 or 2 $C_{1-6}$ alkyl (for example, methyl) or $C_{1-6}$ alkoxy (for example, methoxy);

X is a sulfur atom;

Y is an oxygen atom, an optionally oxidized sulfur atom or a group represented by the formula $NR^{4'}$ ($R^{4'}$ is a hydrogen atom or a $C_{1-6}$ alkyl group) (in particular, an oxygen atom, S, $SO_2$, NH, $N(CH_3)$ and the like);

Z is a $C_{1-6}$ alkylene group (in particular, a $C_{1-3}$ alkylene group) optionally having oxo or $C_{1-6}$ alkyl (for example, $C_{1-3}$ alkyl such as methyl) or a bond.

(C) Compound (I) wherein $R^1$ is an amino group optionally having 1 or 2 acyl represented by the formula —(C=O)—$R^{5"}$ (wherein $R^{5"}$ represents ① a $C_{6-14}$ aryl group (for example, phenyl group) or ② a 5 to 14 membered heterocyclic group containing 1 to 4 heteroatoms of one or two kinds selected from a nitrogen atom, a sulfur atom and an oxygen atom in addition to carbon atoms (for example, a 5 to 6 membered heterocyclic group containing 1 to 2 heteroatoms selected from a nitrogen atom, a sulfur atom and an oxygen atom in addition to carbon atoms such as a pyridyl group);

$R^2$ is a $C_{6-14}$ aryl group (for example, a phenyl group) or a 5 to 14 membered aromatic heterocyclic group containing 1 to 4 heteroatoms of one or two kinds selected from a nitrogen atom, a sulfur atom and an oxygen atom in addition to carbon atoms (for example, a 5 to 6 membered aromatic heterocyclic group containing 1 to 2 heteroatoms selected from a nitrogen atom, a sulfur atom and an oxygen atom in addition to carbon atoms such as a pyridyl group);

$R^3$ is a $C_{6-14}$ aryl group (in particular, a phenyl group) optionally substituted with 1 or 2 $C_{1-6}$ alkyl (for example, methyl) or $C_{1-6}$ alkoxy (for example, methoxy);

X is a sulfur atom;

Y is O, NH or S;

Z is a bond or a $C_{1-6}$ alkylene group (in particular, a $C_{1-3}$ alkylene group optionally having oxo, such as methylene, ethylene and the like) optionally having oxo.

(D) Compound (I) prepared in Examples 1-79.

(E) [4-(3,5-dimethylphenyl)-5-(2-phenylmethyloxy-4-pyridyl)-1,3-thiazol-2-yl]amine (Example Compound No. 1),
N-[4-[2-benzoylamino-4-(4-methoxyphenyl)-1,3-thiazol-5-yl]-2-pyridyl]benzamide (Example Compound No. 2),
N-[4-(4-methoxyphenyl)-5-[2-[(3-pyridylcarbonylamino)]-4-pyridyl]-1,3-thiazol-2-yl]nicotinamide (Example Compound No. 3),
N-[4-[2-amino-4-(4-methoxyphenyl)-1,3-thiazol-5-yl]-2-pyridyl]benzamide (Example Compound No. 4),
N-[4-[2-amino-4-(3,5-dimethylphenyl)-1,3-thiazol-5-yl]-2-pyridyl]benzamide (Example Compound No. 5),
N-[4-[2-amino-4-(3,5-dimethylphenyl)-1,3-thiazol-5-yl]-2-pyridyl]benzylamine (Example Compound No. 6),
N-[4-[2-amino-4-(3,5-dimethylphenyl)-1,3-thiazol-5-yl]-2-pyridyl]benzamide hydrochloride (Example Compound No. 7),
N-[4-[2-amino-4-(3,5-dimethylphenyl)-1,3-thiazol-5-yl]-2-pyridyl]benzylamine dihydrochloride (Example Compound No. 8).

(F) N-[5-[2-benzoylamino-4-pyridyl)-4-(3,5-dimethylphenyl)-1,3-thiazol-2-yl]acetamide (Example Compound No. 9),
N-[5-(2-benzylamino-4-pyridyl)-4-(3,5-dimethylphenyl)-1,3-thiazol-2-yl]acetamide (Example Compound No. 10),
N-[4-[4-(4-methoxyphenyl)-2-methyl-1,3-thiazol-5-yl]-2-pyridyl]benzamide (Example Compound No. 13),
N-[4-[2-(4-fluorophenyl)-4-(3-methylphenyl)-1,3-thiazol-5-yl]-2-pyridyl]phenylacetamide (Example Compound No. 14),
N-[4-[2-ethyl-4-(3-methylphenyl)-1,3-thiazol-5-yl]-2-pyridyl]phenylacetamide (Example Compound No. 15-2),
N-[4-[4-(3-methylphenyl)-2-propyl-1,3-thiazol-5-yl]-2-pyridyl]phenylacetamide (Example Compound No. 15-3),
N-[4-[2-butyl-4-(3-methylphenyl)-1,3-thiazol-5-yl]-2-pyridyl]phenylacetamide (Example Compound No. 15-4),
N-[4-[4-(3-methylphenyl)-2-(4-methylthiophenyl)-1,3-thiazol-5-yl]-2-pyridyl]phenylacetamide (Example Compound No. 15-6),
N-[4-[2-ethyl-4-(3-methylphenyl)-1,3-thiazol-5-yl]-2-pyridyl]benzamide (Example Compound No. 16-1),
N-[4-[2-ethyl-4-(3-methylphenyl)-1,3-thiazol-5-yl]-2-pyridyl]-3-phenylpropionamide (Example Compound No. 16-2),
N-[4-[2-ethyl-4-(3-methylphenyl)-1,3-thiazol-5-yl]-2-pyridyl]-3-(4-methoxyphenyl)propionamide (Example Compound No. 16-3),
N-[4-[2-ethyl-4-(3-methylphenyl)-1,3-thiazol-5-yl]-2-pyridyl]-4-phenylbutyramide (Example Compound No. 16-5),
N-[4-[4-(3-methylphenyl)-2-propyl-1,3-thiazol-5-yl]-2-pyridyl]benzamide (Example Compound No. 16-7),
N-[4-[4-(3-methylphenyl)-2-propyl-1,3-thiazol-5-yl]-2-pyridyl]-3-phenylpropionamide (Example Compound No. 16-8),
N-[4-[2-butyl-4-(3-methylphenyl)-1,3-thiazol-5-yl]-2-pyridyl]benzamide (Example Compound No. 16-9),
N-[4-[2-butyl-4-(3-methylphenyl)-1,3-thiazol-5-yl]-2-pyridyl]-3-phenylpropionamide (Example Compound No. 16-10),
N-[4-[2-(4-fluorophenyl)-4-(3-methylphenyl)-1,3-thiazol-5-yl]-2-pyridyl]benzamide (Example Compound No. 16-11),
N-[4-[2-(4-fluorophenyl)-4-(3-methylphenyl)-1,3-thiazol-5-yl]-2-pyridyl]-3-phenylpropionamide (Example Compound No. 16-12),
N-[4-[4-(3-methylphenyl)-2-(4-methylthiophenyl)-1,3-thiazol-5-yl]-2-pyridyl]benzamide (Example Compound No. 16-15),
N-[4-[4-(3-methylphenyl)-2-(4-methylthiophenyl)-1,3-thiazol-5-yl]-2-pyridyl]-3-phenylpropionamide (Example Compound No. 16-16),
N-benzyl-N-[4-[2-ethyl-4-(3-methylphenyl)-1,3-thiazol-5-yl]-2-pyridyl]amine (Example Compound No. 19-2),
N-[4-[2-ethyl-4-(3-methylphenyl)-1,3-thiazol-5-yl]-2-pyridyl]-N-(2-phenylethyl)amine (Example Compound No. 19-3),
N-[4-[2-ethyl-4-(3-methylphenyl)-1,3-thiazol-5-yl]-2-pyridyl]-N-(3-phenylpropyl)amine (Example Compound No. 19-4),
N-benzyl-N-[4-[4-(3-methylphenyl)-2-propyl-1,3-thiazol-5-yl]-2-pyridyl]amine (Example Compound No. 19-5),
N-[4-(4-(3-methylphenyl)-2-propyl-1,3-thiazol-5-yl]-2-pyridyl]-N-(2-phenylethyl)amine (Example Compound No. 19-6),
N-[4-[4-(3-methylphenyl)-2-propyl-1,3-thiazol-5-yl]-2-pyridyl]-N-(3-phenylpropyl)amine (Example Compound No. 19-7),
N-benzyl-N-[4-[2-butyl-4-(3-methylphenyl)-1,3-thiazol-5-yl]-2-pyridyl]amine (Example Compound No. 19-8),
N-(4-[2-butyl-4-(3-methylphenyl)-1,3-thiazol-5-yl]-2-pyridyl]-N-(2-phenylethyl)amine (Example Compound No. 19-9),
N-[4-[2-butyl-4-(3-methylphenyl)-1,3-thiazol-5-yl]-2-pyridyl]-N-(3-phenylpropyl)amine (Example Compound No. 19-10),
N-benzyl-N-[4-[4-(3-methylphenyl)-2-(4-methylthiophenyl)-1,3-thiazol-5-yl]-2-pyridyl]amine (Example Compound No. 19-17), N-[4-[4-(3-methylphenyl)-2-(4-methylthiophenyl)-1,3-thiazol-5-yl]-2-pyridyl]-N-(2-phenylethyl)amine (Example Compound No. 19-18), N-[4-[4-(3-methylphenyl)-2-(4-methylthiophenyl)-1,3-thiazol-5-yl]-2-pyridyl]-N-(3-phenylpropyl)amine (Example Compound No. 19-19), N-[4-[4-(3-methylphenyl)-2-(4-methylsulfonylphenyl)-1,3-thiazol-5-yl]-2-pyridyl]benzamide (Example Compound No. 20), N-[4-[4-(3-methylphenyl)-2-(4-methylsulfonylphenyl)-1,3-thiazol-5-yl]-2-pyridyl]phenylacetamide (Example Compound No. 21-1), N-[4-[4-(3-methylphenyl)-2-(4-methylsulfonylphenyl)-1,3-thiazol-5-yl]-2-pyridyl]-3-phenylpropionamide (Example Compound No. 21-2), N-benzyl-N-[4-[4-(3-methylphenyl)-2-(4-methylsulfonylphenyl)-1,3-thiazol-5-yl]-2-pyridyl]amine (Example Compound No. 21-5), N-[4-[4-(3-methylphenyl)-2-(4-methylsulfonylphenyl)-1,3-thiazol-5-yl]-2-pyridyl]-N-(3-phenylpropyl)amine (Example Compound No. 21-6), N-[4-[4-(3-methylphenyl)-2-(4-methylsulfonylphenyl)-1,3-thiazol-5-yl]-2-pyridyl]-N-(2-phenylethyl)amine (Example Compound No. 25-1), N-(4-fluorobenzyl)-N-[4-[4-(3-methylphenyl)-2-(4-methylsulfonylphenyl)-1,3-thiazol-5-yl]-2-pyridyl]amine (Example Compound No. 25-2).

As a salt of Compound (I), for example, there are a metal salt, ammonium salt, a salt with an organic base, salt with an inorganic acid, a salt with an organic acid, a salt with basic or acidic amino acid and the like. As a suitable metal salt, there are alkali metal salt such as sodium salt, potassium salt and the like; alkaline earth metal salt such as calcium salt, magnesium salt, barium salt and the like; aluminum salt and the like. As a suitable example of a salt with an organic base, for example, there are salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. As a suitable example of a salt with an inorganic acid, for example, there are salts with hydrochloric acid, hydrobromic acid, nitric acid, sulfuric acid, phosphoric acid and the like. As a suitable example of a salt with an organic acid, for example, there are salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. As a suitable example of a salt with a basic amino acid, for example, there are salts with arginine, lysine, ornithine and the like. As a suitable example of a salt with an acidic amino acid, for example, there are salts with aspartic acid, glutamic acid and the like.

Among them, pharmaceutically acceptable salts are preferable. For example, when a compound has an acidic functional group therein, there are inorganic salts such as alkali metal salts (for example, sodium salt, potassium salt and the like), alkaline earth metal salts (for example, calcium salt, magnesium salt, barium salt and the like), ammonium salts and the like and, when a compound has a basic functional group therein, there are salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like.

A process for producing Compound (I) will be described below. Compound (Ia), (Ib), (Ic) or (Id) is a compound included in Compound (I).

Compound (I) is obtained by a method shown by the following reaction formulas 1, 2, 4 and 5 or a similar method to that.

Respective symbols in compounds in the following reaction formulas 1, 2, 4 and 5 have the same meanings as those described above. Compounds in the reaction formulas include salts thereof and, as the salts, for example, there are the same as those of Compound (I).

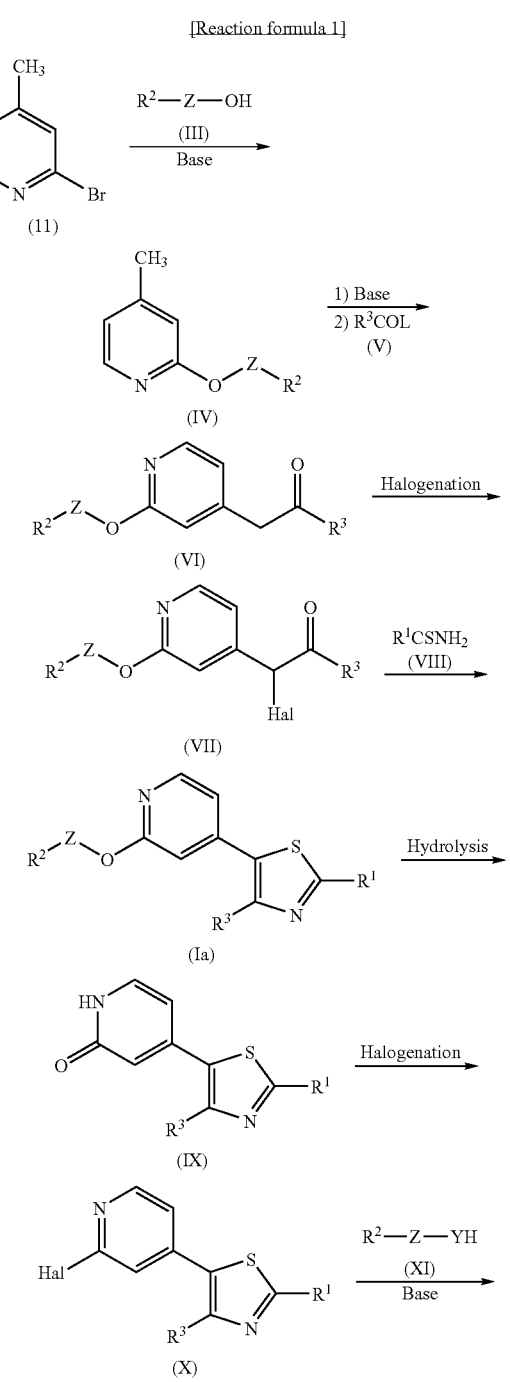

-continued

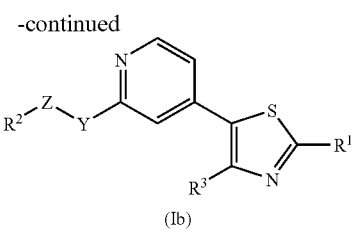

(Ib)

Hal: Halogen

Compounds (II), (III), (V), (VIII), (XI), (XII), (XVII), (XVIII), (XIX), (XX), (XXI), (XXII), (XXVI) and (XXVII) can be used as they are when they are commercially available or can be prepared by a method known per se or according to the similar method to this.

Compound (IV) can be obtained by condensing Compound (II) and Compound (III) in the presence of a base.

An amount of Compound (III) to be used is about 0.5 to about 3 moles, preferably about 0.8 to about 2 moles relative to 1 mole of Compound (II).

An amount of a base to be used is about 1 to about 30 moles, preferably about 1 to about 10 moles relative to 1 mole of Compound (II).

As the "base", for example, there are basic salts such as sodium carbonate, potassium carbonate, cesium carbonate, sodium acetate and the like, an inorganic base such as sodium hydroxide, potassium hydroxide and the like, an aromatic amine such as pyridine, lutidine and the like, a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, an alkali metal hydride such as sodium hydride, potassium hydride and the like, a metal amide such as sodium amide, lithium diisopropylamide, lithium hexamethyldisilazide and the like, a metal alkoxide such as sodium methoxide, sodium ethoxide, potassium tert-butoxide and the like.

It is advantageous that this reaction is conducted without a solvent or in the presence of an inert solvent. Although the solvent is not particularly limited as long as the reaction proceeds, for example, halogenated hydrocarbons, aliphatic hydrocarbons, aromatic hydrocarbons, ethers, amides, alcohols, water or a mixture of two or more of them are used.

A reaction temperature is usually about −5 to about 200° C., preferably about 5 to about 150° C. A reaction time is usually about 5 minutes to about 72 hours, preferably about 0.5 to about 20 hours.

Although the reaction product can be used as the reaction solution itself or as a crude product in the next step, it can be isolated from the reaction mixture according to the conventional method and can be easily purified by a separating means such as recrystallization, distillation, chromatography and the like.

Compound (VI) can be obtained by treating Compound (IV) with a base and condensing the obtained compound with Compound (V).

In Compound (V), L represents a leaving group. As "leaving group" denoted by L, for example, there are ① $C_{1-6}$ alkoxy (for example, methoxy, ethoxy and the like), ② di-$C_{1-6}$ alkylamino (for example, dimethylamino, diethylamino and the like), ③ N-$C_{6-10}$ aryl-N-$C_{1-6}$ alkylamino (for example, N-phenyl-N-methylamino and the like), ④ 3 to 7 membered cyclic amino (for example, pyrrolidino, morpholino, methylaziridin-1-yl and the like) optionally substituted with $C_{6-10}$ aryl and (or) $C_{1-6}$ alkyl, ⑤ N—$C_{1-6}$ alkyl-N—$C_{1-6}$ alkoxyamino (N-methoxy-N-methylamino and the like) and the like. Further, as "leaving group" denoted by L, for example, there are hydroxy, halogen atom (for example, fluorine, chlorine, bromine, iodine and the like), optionally halogenated $C_{1-5}$ alkylsulfonyloxy (for example, methanesulfonyloxy, ethanesulfonyloxy, trichloromethanesulfonyloxy and the like), $C_{6-10}$ arylsulfonyloxy optionally having substituents and the like. As "$C_{6-10}$ arylsulfonyloxy optionally having substituents", for example, there are $C_{6-10}$ arylsulfonyloxy (for example, phenylsulfonyloxy, naphthylsulfonyloxy and the like) optionally having 1 to 3 substituents selected from $C_{1-6}$ alkyl, $C_{1-6}$ alkoxy and nitro. Examples thereof are benzenesulfonyloxy, m-nitrobenzenesulfonyloxy, p-toluenesulfonyloxy and the like.

An amount of a base to be used is about 0.8 to about 3 moles, preferably about 1 to about 1.2 moles relative to 1 mole of Compound (IV).

As the "base", for example, metal amides such as sodium amide, lithium diisopropylamide, lithium hexamethyldisilazide and the like are used.

It is advantageous that this reaction is conducted without a solvent or in the presence of an inert solvent for a reaction. The solvent is not particularly limited as long as a reaction proceeds but, for example, aliphatic hydrocarbons, aromatic hydrocarbons, ethers or a mixture of two or more of them and the like are used.

A reaction temperature is usually about −78 to about 60° C., preferably about −78 to about 20° C. A reaction time is usually about 5 minutes to about 24 hours, preferably about 0.5 to about 3 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (VII) can be obtained by treating Compound (VI) with halogens or a metal halide. This reaction is performed in the presence of a base or a basic salt if desired.

An amount of halogens or a metal halide to be used is about 1 to about 5 moles, preferably about 1 to about 2 moles relative to 1 mole of Compound (VI).

As the "halogens", there are bromine, chlorine, iodine and the like.

As the "metal halide", there are copper halides such as copper (II) bromide, copper (II) chloride and the like.

An amount of a base to be used is about 1 to about 30 moles, preferably about 1 to about 10 moles relative to 1 mole of Compound (VI).

As the "base", for example, there are inorganic bases such as sodium hydroxide, potassium hydroxide, lithium hydroxide and the like, basic salts such as sodium carbonate, potassium carbonate, cesium carbonate, sodium hydrogencarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like.

It is advantageous that this reaction is performed without a solvent or in the presence of an inert solvent for a reaction. The solvent is not particularly limited as long as a reaction proceeds but, for example, ethers, esters, aromatic hydrocarbons, aliphatic hydrocarbons, amides, halogenated hydrocarbons, nitriles, sulfoxides, organic acids, aromatic amines or a mixture of two or more of them and the like are used.

A reaction temperature is about −20 to about 150° C., preferably about 0 to about 100° C. A reaction time is usually about 5 minutes to about 24 hours, preferably about 10 minutes to about 5 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (Ia) can be obtained by condensing Compound (VII) with Compound (VIII). This reaction is performed in the presence of a base if desired.

In Compound (VII), Hal represents halogens.

When Compound (VIII) is commercially available, it can be used as it is, or can be obtained by the method known per se or a method according to the known method or further a method shown in the reaction formula 3.

An amount of Compound (VIII) to be used is about 0.5 to about 3 moles, preferably about 0.8 to about 2 moles relative to 1 mole of Compound (VII).

An amount of a base to be used is about 1 to about 30 moles, preferably about 1 to about 10 moles relative to 1 mole of Compound (VII).

As the "base", for example, there are alkali metals such as sodium hydroxide, potassium hydroxide, lithium hydroxide and the like, basic salts such as sodium carbonate, potassium carbonate, cesium carbonate, sodium hydrogencarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like.

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, ethers, amides, alcohols, nitriles or a mixture of two or more of them and the like are used.

A reaction temperature is about −5 to about 200° C., preferably about 5 to about 150° C. A reaction time is usually about 5 minutes to about 72 hours, preferably about 0.5 to about 30 hours.

Although a product can be used as the reaction solution itself or as a crude product in the next reaction, it can be isolated from the reaction mixture by conventional methods, and can be easily purified by a separating means such as recrystallization, distillation, chromatography and the like.

Compound (IX) can be obtained by treating Compound (Ia) with an acid.

An amount of an acid to be used is about 1 to about 100 moles, preferably about 1 to about 30 moles relative to 1 mole of Compound (Ia).

As the "acid", for example, there are mineral acids such as hydrochloric acid, hydrobromic acid, sulfuric acid and the like, organic acids such as acetic acid, propionic acid, trifluoroacetic acid and the like.

This reaction is performed in the presence of an inert solvent for a reaction. The solvent is not particularly limited as long as a reaction proceeds but, for example, water, a mixture of water and amides, a mixture of water and alcohols and the like are used.

A reaction temperature is usually about 20 to about 200° C., preferably about 60 to about 150° C. A reaction time is usually about 30 minutes to about 72 hours, preferably about 1 to about 30 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (X) is obtained by treating Compound (IX) with a halogenating agent.

An amount of a halogenating agent to be used is about 1 to about 10 moles, preferably about 1 to about 5 moles relative to 1 mole of Compound (IX).

As the "halogenating agent", there are thionyl chloride, phosphorus pentachloride, phosphorus oxychloride and the like.

It is advantageous that this reaction is performed without a solvent or in the presence of an inert solvent for a reaction. The solvent is not particularly limited as long as a reaction proceeds but, for example, ethers, aromatic hydrocarbons, aliphatic hydrocarbons, amides, halogenated hydrocarbons, nitrites, sulfoxides, organic acids, aromatic amines or a mixture of two or more of them and the like are used.

A reaction temperature is usually about −20 to about 150° C., preferably about 0 to about 100° C. A reaction time is usually about 5 minutes to about 24 hours, preferably about 10 minutes to about 5 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (Ib) can be obtained by condensing Compound (X) with Compound (XI). This reaction is performed in the presence of a base if desired.

An amount of a base to be used is about 0.8 to about 30 moles, preferably about 1 to about 10 moles relative to 1 mole of Compound (X).

As the "base", for example, there are basic salts such as sodium carbonate, potassium carbonate, cesium carbonate and the like, inorganic bases such as sodium hydroxide, potassium hydroxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like.

It is advantageous that this reaction is performed without a solvent or in the presence of an inert solvent for a reaction. The solvent is not particularly limited as long as a reaction proceeds but, for example, aliphatic hydrocarbons, aromatic hydrocarbons, ethers or a mixture of two or more of them and the like are used.

A reaction temperature is usually about −78 to about 200° C., preferably about room temperature to about 170° C. A reaction time is usually about 5 minutes to about 72 hours, preferably about 0.5 to about 24 hours.

Although a product can be used as the reaction solution itself or as a crude product in the next reaction, it can be isolated from the reaction mixture by the conventional method, and can be easily purified by a separating means such as recrystallization, distillation, chromatography and the like.

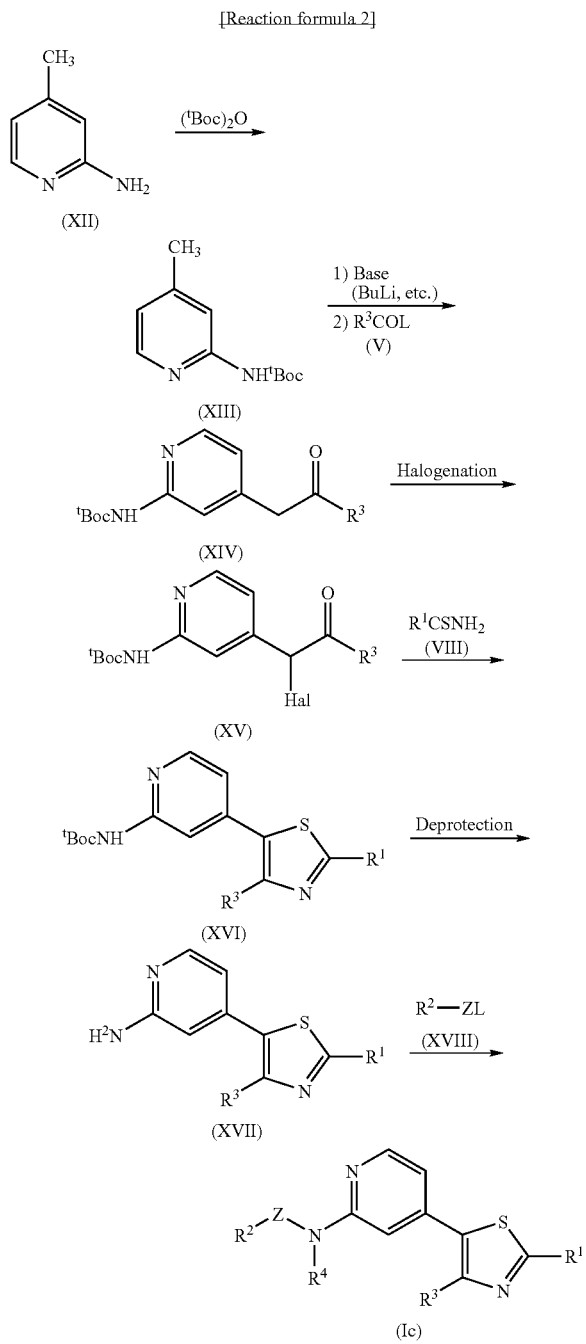

L: leaving group
<sup>t</sup>Boc: t-butoxycarbonyl
Bu: butyl

Compound (XIII) is obtained from Compound (XII) by a method described in Synthesis, p.p. 877-882, 1996 or Journal of Organic Chemistry, vol. 61, p.p. 4810-4811, 1996.

Compound (XIV) is obtained by treating Compound (XIII) with a base and condensing the obtained compound with Compound (V).

An amount of a base to be used is about 0.8 to about 5 moles, preferably about 2 to about 2.5 moles relative to 1 mole of Compound (XIII).

As the "base", for example, alkyllithiums such as n-butyllithium and the like and metal amides such as sodium amide, lithium diisopropylamide, lithium hexamethyldisilazide and the like are used.

It is advantageous that this reaction is performed without a solvent or in the presence of an inert solvent for a reaction. The solvent is not particularly limited as long as a reaction proceeds but, for example, aliphatic hydrocarbons, aromatic hydrocarbons, ethers or a mixture of two or more of them and the like are used.

A reaction temperature is usually about −78 to about 60° C., preferably about −78 to about 20° C. A reaction time is usually about 5 minutes to about 24 hours, preferably about 0.5 to about 3 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (XV) can be obtained by treating Compound (XIV) with halogens or a metal halide. This reaction is performed optionally in the presence of a base or a basic salt.

An amount of halogens or a metal halide to be used is about 1 to about 5 moles, preferably about 1 to about 2 moles relative to 1 mole of Compound (XIV).

As the "halogens", there are bromine, chlorine, iodine and the like.

As the "metal halide", there are copper halide such as copper (II) bromide, copper (II) chloride and the like.

An amount of a base to be used is about 1 to about 10 moles, preferably about 1 to about 3 moles relative to 1 mole of Compound (XIV).

As the "base", for example, there are alkali metals such as sodium hydroxide, potassium hydroxide, lithium hydroxide and the like, basic salts such as sodium carbonate, potassium carbonate, cesium carbonate, sodium hydrogencarbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like.

It is advantageous that this reaction is performed without a solvent or in the presence of an inert solvent for a reaction. The solvent is not particularly limited as long as a reaction proceeds but, for example, ethers, esters, aromatic hydrocarbons, aliphatic hydrocarbons, amides, halogenated hydrocarbons, nitrites, sulfoxides, organic acids, aromatic amines or a mixture of two or more of them and the like are used.

A reaction temperature is usually about −20 to about 150° C., preferably about 0 to about 100° C. A reaction time is usually about 5 minutes to about 24 hours, preferably about 10 minutes to about 5 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (XVI) can be obtained by condensing Compound (XV) and Compound (VIII). This reaction is performed optionally in the presence of a base.

In Compound (XV), Hal represents halogens.

When Compound (VIII) is commercially available, it can be used as it is, or is obtained by the method known per se or a method according to the known method, or further by a method shown by the following reaction formula 3.

An amount of Compound (VIII) to be used is about 0.5 to about 3 moles, preferably about 0.8 to about 2 moles relative to 1 mole of Compound (XV).

An amount of a base to be used is about 1 to about 30 moles, preferably about 1 to about 10 moles relative to 1 mole of Compound (XV).

As the "base", for example, there are basic salts such as sodium carbonate, potassium carbonate, cesium carbonate, sodium hydrogencarbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like.

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, ethers, amides, alcohols, nitriles or a mixture of two or more of them and the like are used.

A reaction temperature is about −5 to about 200° C., preferably about 5 to about 150° C. A reaction time is usually about 5 minutes to about 72 hours, preferably about 0.5 to about 30 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (XVII) is obtained by deprotecting Compound (XVI) using an acid or a base.

An amount of an acid or a base to be used is about 0.1 to about 50 moles, preferably about 1 to about 20 moles relative to 1 mole of Compound (XVI).

As the "acid", for example, mineral acids such as hydrochloric acid, hydrobromic acid, sulfuric acid and the like, Lewis acids such as boron trichloride, boron tribromide and the like, the use of Lewis acid together with thiols or sulfides, organic acids such as trifluoroacetic acid, p-toluenesulfonic acid and the like are used.

As the "base", for example, metal hydroxides such as sodium hydroxide, potassium hydroxide, barium hydroxide and the like, basic salts such as sodium carbonate, potassium carbonate and the like, metal alkoxides such as sodium methoxide, sodium ethoxide, potassium tert-butoxide and the like, organic bases such as triethylamine, imidazole, formamidine and the like are used.

It is advantageous that this reaction is performed without a solvent or in the presence of an inert solvent for a reaction. The solvent is not particularly limited as long as a reaction proceeds but, for example, alcohols, ethers, aromatic hydrocarbons, aliphatic hydrocarbons, halogenated hydrocarbons, sulfoxides, water or a mixture of two or more of them and the like are used.

A reaction time is usually about 10 minutes to about 50 hours, preferably about 30 minutes to about 12 hours. A reaction temperature is about 0 to about 200° C., preferably about 20 to about 120° C.

Compound (Ic) can be obtained by condensing Compound (XVII) with Compound (XVIII) optionally in the presence of a base.

An amount of Compound (XVIII) to be used is about 0.8 to about 5 moles, preferably about 1 to about 3 moles relative to 1 mole of Compound (XVII).

An amount of a base to be used is about 0.1 to about 3 moles, preferably about 0.3 to about 1.2 moles relative to 1 mole of Compound (XVII).

As the "base", for example, there are basic salts such as sodium carbonate, potassium carbonate, cesium carbonate, sodium acetate and the like, inorganic base such as sodium hydroxide, potassium hydroxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like.

It is advantageous that this reaction is performed without a solvent or in the presence of an inert solvent for a reaction. The solvent is not particularly limited as long as a reaction proceeds but, for example, aliphatic hydrocarbons, aromatic hydrocarbons, ethers or a mixture of two or more of them and the like are used.

A reaction temperature is usually about −78 to about 100° C., preferably about −78 to about 70° C. A reaction time is usually about 5 minutes to about 24 hours, preferably about 0.5 to about 20 hours.

Although a product can be used as the reaction solution itself or as a crude product in the next reaction, it can be isolated from the reaction mixture by the conventional method, and can be easily purified by a separating means such as recrystallization, distillation, chromatography and the like. Thereafter, compounds wherein $R^4$ is other than hydrogen atom can be synthesized by performing alkylation or acylation if desired.

[Reaction formula 3]

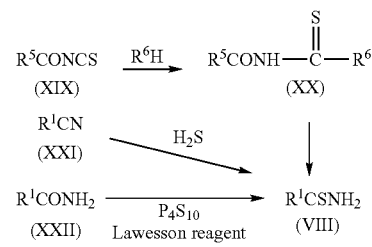

Compound (XX) is obtained by condensing Compound (XIX) and amines represented by the formula $R^6H$.

$R^6$ represents "amino optionally having substituents" represented by the above-mentioned $R^1$.

In Compound (XIX), $R^5$ represents an alkoxy group. As the "alkoxy group", for example, there are a $C_{1-6}$ alkoxy group such as methoxy, ethoxy, propoxy, isopropoxy, butoxy and the like.

An amount of the "amines" to be used is about 1 to about 30 moles, preferably about 1 to about 10 moles relative to 1 mole of Compound (XIX).

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, ethers, amides, alcohols, nitriles, ketones or a mixture of two or more of them and the like are used.

A reaction temperature is about −5 to about 200° C., preferably about 5 to about 120° C. A reaction time is usually about 5 minutes to about 72 hours, preferably about 0.5 to about 30 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (VIII) is obtained by hydrolysing Compound (XX) using an acid or a base.

An amount of an acid or a base to be used is about 0.1 to about 50 moles, preferably about 1 to about 20 moles relative to 1 mole of Compound (XX), respectively.

As the "acid", for example, mineral acids such as hydrochloric acid, hydrobromic acid, sulfuric acid and the like, Lewis acids such as boron trichloride, boron tribromide and the like, the use of Lewis acid together with thiols or sulfides, organic acids such as trifluoroacetic acid, p-toluenesulfonic acid and the like are used.

As the "base", for example, metal hydroxides such as sodium hydroxide, potassium hydroxide, barium hydroxide and the like, basic salts such as sodium carbonate, potassium carbonate, sodium acetate and the like, metal alkoxides such as sodium methoxide, sodium ethoxide, potassium tert-butoxide and the like, organic bases such as triethylamine, imidazole, formamidine and the like are used.

It is advantageous that this reaction is performed without a solvent or in the presence of an inert solvent for a reaction. The solvent is not particularly limited as long as a reaction proceeds but, for example, alcohols, ethers, aromatic hydrocarbons, aliphatic hydrocarbons, halogenated hydrocarbons, sulfoxides, water or a mixture of two or more of them and the like are used.

A reaction time is usually about 10 minutes to about 50 hours, preferably about 30 minutes to about 12 hours. A reaction temperature is about 0 to about 200° C., preferably about 20 to about 120° C.

Compound (VIII) can be obtained by treating Compound (XXI) with hydrogen sulfide in the presence of a base.

An amount of hydrogen sulfide is about 1 mole to about 30 moles relative to 1 mole of Compound (XXI).

An amount of a base to be used is about 1 to about 30 moles, preferably about 1 to about 10 moles relative to 1 mole of Compound (XXI).

As the "base", for example, there are aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, ammonia and the like.

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, ethers, aromatic amines or a mixture of two or more of them and the like are used.

This reaction is performed under atmospheric pressure or under pressurized condition. A reaction temperature is usually about −20 to about 80° C., preferably about −10 to about 30° C. A reaction time is usually about 5 minutes to about 72 hours, preferably about 0.5 to about 30 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (VIII) can also be obtained by treating Compound (XXII) with phosphorus pentasulfide or Lawesson's reagent.

An amount of phosphorus pentasulfide or Lawesson's reagent to be used is about 0.5 to about 10 moles, preferably about 0.5 to about 3 moles relative to 1 mole of Compound (XXII).

It is advantageous that this reaction is performed without a solvent or in the presence of an inert solvent for a reaction. The solvent is not particularly limited as long as a reaction proceeds but, for example, ethers, aromatic hydrocarbons, aliphatic hydrocarbons, halogenated hydrocarbons or a mixture of two or more of them and the like are used.

A reaction time is usually 10 minutes to about 50 hours, preferably about 30 minutes to about 12 hours. A reaction temperature is usually about 0 to about 150° C., preferably about 20 to about 120° C.

Although a product (VIII) can be used as the reaction solution itself or as a crude product in the next reaction, it can be isolated from the reaction mixture by the conventional method, and can be easily purified by a separating means such as recrystallization, distillation, chromatography and the like.

When Compound (I) (including Compound (Ia), (Ib) and (Ic)) is acylamino compound, an objective compound can be also obtained by subjecting the corresponding amine compound to an acylating reaction known per se.

For example, among Compound (I), a compound wherein $R^1$ is acylamino group optionally having substituents is obtained by reacting the corresponding 2-thiazolamine and an acylating agent optionally in the presence of a base or an acid.

An amount of an acylating agent to be used is about 1 to about 5 moles, preferably about 1 to about 2 moles relative to 1 mole of the corresponding 2-thiazolamine.

As the "acylating agent", for example, there are carboxylic acids corresponding to an objective acyl group or a reactive derivative thereof (for example, acid halide, acid anhydride, ester and the like) and the like.

An amount of a base or an acid to be used is about 0.8 to about 5 moles, preferable about 1 to about 2 moles relative to 1 mole of the corresponding 2-thiazolamine.

As the "base", for example, there are triethylamine, pyridine, 4-dimethylaminopyridine and the like.

As the "acid", for example, there are methanesulfonic acid, p-toluenesulfonic acid, camphorsulfonic acid and the like.

It is advantageous that this reaction is performed without a solvent or in the presence of an inert solvent for a reaction. The solvent is not particularly limited as long as a reaction proceeds but, for example, ethers, aromatic hydrocarbons, aliphatic hydrocarbons, amides, halogenated hydrocarbons, nitrites, sulfoxides, aromatic amines or a mixture of two or more of them and the like are used.

A reaction temperature is about −20 to about 150° C., preferably about 0 to about 100° C. A reaction time is usually 5 minutes to about 24 hours, preferably about 10 minutes to about 5 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (Id) is also obtained by a method shown by the reaction formula 4 or a method according that method.

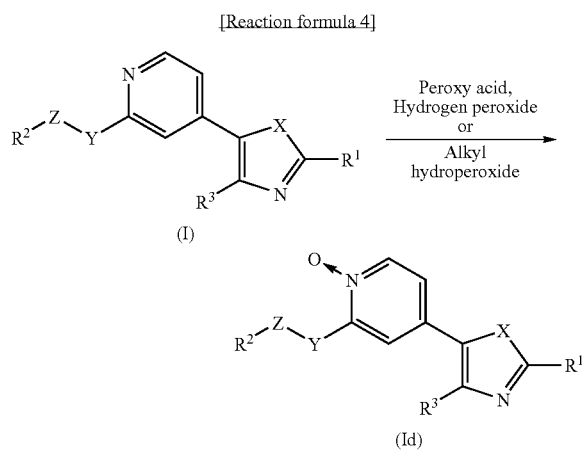

[Reaction formula 4]

Compound (Id) is obtained by treating Compound (I) with an organic peroxy acid.

An amount of an organic peroxy acid to be used is about 0.8 to about 10 moles, preferable about 1 to about 3 moles relative to 1 mole of Compound (I).

As the "organic peroxy acid", for example, there are peracetic acid, trifluoroperacetic acid, m-chloroperbenzoic acid and the like.

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, organic acids, ethers, amides, sulfoxides, alcohols, nitriles, ketones or a mixture of two or more of them and the like are used.

A reaction temperature is about −20 to about 130° C., preferably about 0 to about 100° C. A reaction time is usually 5 minutes to about 72 hours, preferably about 0.5 to about 12 hours.

Alternatively, Compound (Id) is also obtained by treating Compound (I) with hydrogen peroxide or alkyl hydroperoxide optionally in the presence of a base, an acid or a metal oxide.

An amount of hydrogen peroxide or alkyl hydroperoxide to be used is about 0.8 to about 10 moles, preferably about 1 to 3 moles to 1 mole of Compound (I).

As the "alkyl hydroperoxide", for example, there are tert-butyl hydroperoxide, cumene hydroperoxide and the like.

An amount of a base, an acid or a metal oxide to be used is about 0.1 to about 30 moles, preferably 0.8 to about 5 moles relative to 1 mole of Compound (I).

As the "base", for example, there are inorganic bases such as sodium hydroxide, potassium hydroxide and the like, basic salts such as sodium carbonate, potassium carbonate, sodium acetate and the like.

As the "acid", for example, there are mineral acids such as hydrochloric acid, sulfuric acid, perchloric acid and the like, Lewis acids such as boron trifluoride, aluminum chloride, titanium tetrachloride and the like, organic acids such as formic acid, acetic acid and the like.

As the "metal oxide", for example, there are vanadium oxide ($V_2O_5$), osmium tetroxide ($OSO_4$), tungsten oxide ($WO_3$), molybdenum oxide ($MoO_3$), selenium dioxide ($SeO_2$), chromium oxide ($CrO_3$) and the like.

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, organic acids, ethers, amides, sulfoxides, alcohols, nitriles, ketones or a mixture of two or more of them and the like are used.

A reaction temperature is about −20 to about 130° C., preferably about 0 to about 100° C. A reaction time is usually 5 minutes to about 72 hours, preferably about 0.5 to about 12 hours.

Although a product can be used as the reaction solution itself or as a crude product in the next reaction, it can be isolated from the reaction mixture by the conventional method, and can be easily purified by a separating means such as recrystallization, distillation, chromatography and the like.

Alternatively, Compound (Ic) is also obtained by a method shown by the following reaction formula 5:

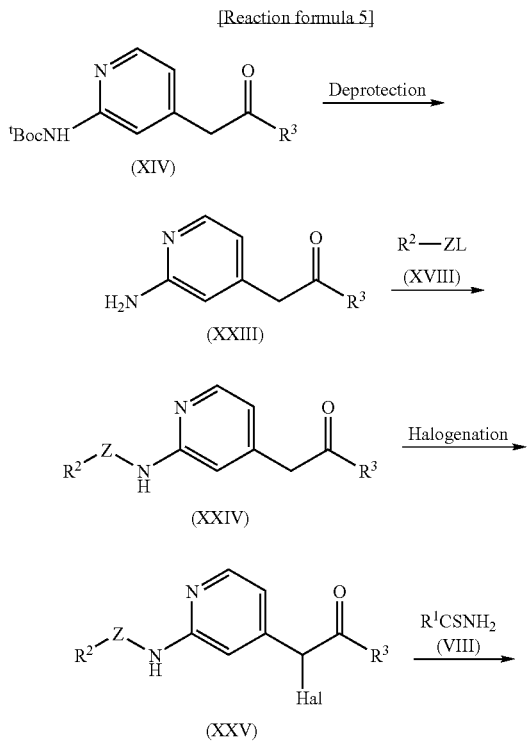

[Reaction formula 5]

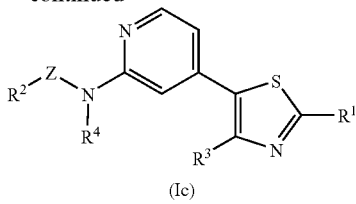

(Ic)

Compound (XXIII) is obtained by deprotecting Compound (XIV) using an acid or a base.

An amount of an acid or a base to be used is about 0.1 to about 50 moles, preferably about 1 to about 20 moles relative to one mole of Compound (XIV), respectively.

As the "acid", for example, mineral acids such as hydrochloric acid, hydrobromic acid, sulfuric acid and the like, Lewis acids such as boron trichloride, boron tribromide and the like, the use of Lewis acid together with thiols or sulfides, organic acids such as trifluoroacetic acid, p-toluenesulfonic acid and the like are used.

As the "base", for example, metal hydroxides such as sodium hydroxide, potassium hydroxide, barium hydroxide and the like, basic salts such as sodium carbonate, potassium carbonate and the like, metal alkoxides such as sodium methoxide, sodium ethoxide, potassium tert-butoxide and the like, organic bases such as triethylamine, imidazole, formamidine and the like are used.

It is advantageous that this reaction is performed without a solvent or in the presence of an inert solvent for a reaction. The solvent is not particularly limited as long as a reaction proceeds but, for example, alcohols, ethers, aromatic hydrocarbons, aliphatic hydrocarbons, halogenated hydrocarbons, sulfoxides, water or a mixture of two or more of them and the like are used.

A reaction time is usually about 10 minutes to about 50 hours, preferably about 30 minutes to about 12 hours. A reaction temperature is about 0 to about 200° C., preferably about 20 to about 120° C.

Although a product can be used as the reaction solution itself or as a crude product in the next reaction, it can be isolated from the reaction mixture by the conventional method, and can be easily purified by a separating means such as recrystallization, distillation, chromatography and the like.

Compound (XXIV) is obtained by condensing Compound (XXIII) and Compound (XVIII) optionally in the presence of a base.

An amount of Compound (XVIII) to be used is about 0.8 to about 5 moles, preferably about 1 to about 3 moles relative to one mole of Compound (XXIII).

An amount of a base to be used is about 0.1 to about 3 moles, preferably about 0.3 to about 1.2 moles relative to 1 mole of Compound (XXIII).

As the "base", for example, basic salts such as sodium carbonate, potassium carbonate, cesium carbonate, sodium acetate and the like, inorganic bases such as sodium hydroxide, potassium hydroxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like.

It is advantageous that this reaction is performed without a solvent or in the presence of an inert solvent for a reaction. The solvent is not particularly limited as long as a reaction proceeds but, for example, aliphatic hydrocarbons, aromatic hydrocarbons, ethers, water or a mixture of two or more of them and the like are used.

A reaction temperature is usually about −78 to about 100° C., preferably about −78 to about 70° C. A reaction time is usually about 5 minutes to about 24 hours, preferably about 0.5 to about 20 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (XXV) is obtained by treating Compound (XXIV) with a halogen or a metal halide. This reaction is performed optionally in the presence of a base or a basic salt.

The amount of halogen or a metal halide to be used is about 1 to about 5 moles, preferably about 1 to about 2 moles relative to one mole of Compound (XXIV).

As the "halogens", there are bromine, chlorine, iodine and the like.

As the "metal halide", there are copper halide such as copper (II) bromide, copper (II) chloride and the like.

An amount of a base to be used is about 1 to about 10 moles, preferably about 1 to about 3 moles relative to 1 mole of Compound (XXIV).

As the "base", for example, there are alkali metals such as sodium hydroxide, potassium hydroxide, lithium hydroxide and the like, basic salts such as sodium carbonate, potassium carbonate, cesium carbonate, sodium hydrogencarbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like.

It is advantageous that this reaction is performed without a solvent or in the presence of an inert solvent for a reaction. The solvent is not particularly limited as long as a reaction proceeds but, for example, ethers, esters, aromatic hydrocarbons, aliphatic hydrocarbons, amides, halogenated hydrocarbons, nitriles, sulfoxides, organic acids, aromatic amines or a mixture of two or more of them and the like are used.

A reaction temperature is usually about −20 to about 150° C., preferably about 0 to about 100° C. A reaction time is usually about 5 minutes to about 24 hours, preferably about 10 minutes to about 5 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (Ic) is obtained by condensing Compound (XXV) and Compound (VIII). This reaction is performed optionally in the presence of a base.

In Compound (XXV), Hal represents halogens.

An amount of Compound (VIII) to be used is about 0.5 to about 3.0 moles, preferably about 0.8 to about 2 moles relative to 1 mole of Compound (XXV).

An amount of a base to be used is about 1 to about 30 moles, preferably about 1 to about 10 moles relative to 1 mole of Compound (XXV).

As the "base", for example, there are basic salts such as sodium carbonate, potassium carbonate, cesium carbonate, sodium hydrogencarbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like.

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, ethers, amides, alcohols, nitrites or a mixture of two or more of them and the like are used.

A reaction temperature is usually about −5 to about 200° C., preferably about 5 to about 150° C. A reaction time is usually about 5 minutes to about 72 hours, preferably about 0.5 to about 30 hours.

Although a product can be used as the reaction solution itself or as a crude product in the next reaction, it can be isolated from the reaction mixture by the conventional method, and can be easily purified by a separating means such as recrystallization, distillation, chromatography and the like. Thereafter, if desired, compounds other than a compound wherein $R^4$ is hydrogen atom may be synthesized by performing alkylation or acylation.

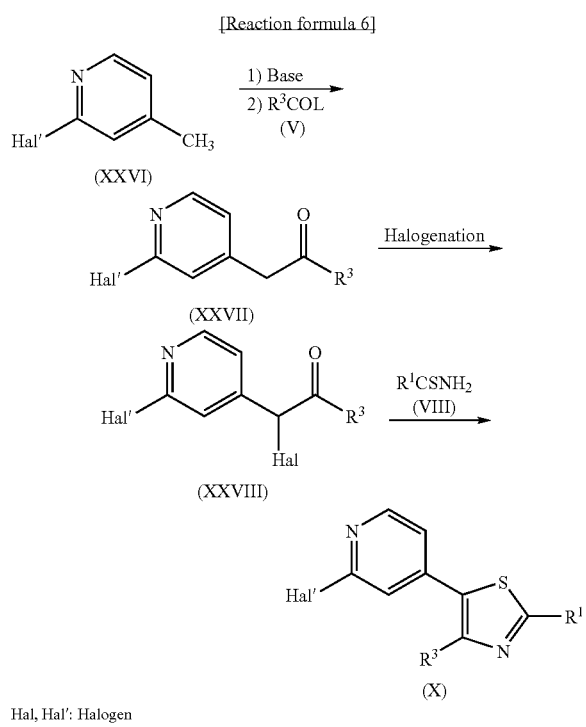

Hal, Hal': Halogen

Compound (XXVII) is obtained by treating Compound (XXVI) with a base and condensing the obtained compound with Compound (V).

In Compound (XXVI), Hal' represents a halogen atom such as fluorine, chlorine, bromine and iodine.

An amount of a base to be used is about 0.8 to about 5 moles, preferably about 1 to about 1.2 moles relative to 1 mole of Compound (XXVI).

As the "base", for example, alkyllithiums such as n-butyllithium and the like, metal amides such as sodium amide, lithium diisopropylamide, lithium hexamethyldisilazide and the like are used.

It is advantageous that this reaction is performed without a solvent or in the presence of an inert solvent for a reaction. The solvent is not particularly limited as long as a reaction proceeds but, for example, aliphatic hydrocarbons, aromatic hydrocarbons, ethers or a mixture of two or more of them and the like are used.

A reaction temperature is usually about −78 to about 60° C., preferably about −78 to about 20° C. A reaction time is usually about 5 minutes to about 24 hours, preferably about 0.5 to about 3 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (XXVIII) is obtained by treating Compound (XXVII) with halogens or a metal halide. This reaction is performed optionally in the presence of a base or a basic salt.

In Compound (XXVII), Hal' represents a halogen atom such as fluorine, chlorine, bromine and iodine.

An amount of halogens or a metal halide to be used is about 1 to about 5 moles, preferably about 1 to about 2 moles relative to one mole of Compound (XXVII).

As the "halogens", there are bromine, chlorine, iodine and the like.

As the "metal halide", there are copper halide such as copper (II) bromide, copper (II) chloride and the like.

An amount of a base to be used is about 1 to about 10 moles, preferably about 1 to about 3 moles relative to 1 mole of Compound (XXVII).

As the "base", for example, there are alkali metals such as sodium hydroxide, potassium hydroxide, lithium hydroxide and the like, basic salts such as sodium carbonate, potassium carbonate, cesium carbonate, sodium hydrogencarbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like.

It is advantageous that this reaction is performed without a solvent or in the presence of an inert solvent for a reaction. The solvent is not particularly limited as long as a reaction proceeds but, for example, ethers, esters, aromatic hydrocarbons, aliphatic hydrocarbons, amides, halogenated hydrocarbons, nitrites, sulfoxides, organic acids, aromatic amines or a mixture of two or more of them and the like are used.

A reaction temperature is usually about −20 to about 150° C., preferably about 0 to about 100° C. A reaction time is usually about 5 minutes to about 24 hours, preferably about 10 minutes to about 5 hours.

Although a product can be used as the reaction solution itself or as a crude product in the next reaction, it can be isolated from the reaction mixture by the conventional method, and can be easily purified by a separating means such as recrystallization, distillation, chromatography and the like.

Compound (X) is obtained by condensing Compound (XXVIII) and Compound (VIII). This reaction is performed optionally in the presence of a base.

In Compound (XXVIII), Hal and Hal' denote halogen atoms such as fluorine, chlorine, bromine and iodine.

An amount of Compound (VIII) to be used is about 0.5 to about 3 moles, preferably about 0.8 to about 2 moles relative to 1 mole of Compound (XXVIII).

An amount of a base to be used is about 1 to about 30 moles, preferably about 1 to about 10 moles relative to 1 mole of Compound (XXVIII).

As the "base", for example, there are basic salts such as sodium carbonate, potassium carbonate, cesium carbonate, sodium hydrogencarbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like.

It is advantageous that this reaction is performed without a solvent or in the presence of an inert solvent for a reaction. The solvent is not particularly limited as long as a reaction proceeds but, for example, halogenated hydrocarbons, aliphatic hydrocarbons, aromatic hydrocarbons, ethers, amides, alcohols, nitriles or a mixture of two or more of them and the like are used.

A reaction temperature is usually about −5 to about 200° C., preferably about 5 to about 150° C. A reaction time is usually about 5 minutes to about 72 hours, preferably about 0.5 to about 30 hours.

Although a product can be used as the reaction solution itself or as a crude product in the next reaction, it can be isolated from the reaction mixture by the conventional method, and can be easily purified by a separating means such as recrystallization, distillation, chromatography and the like.

In the above respective reactions, when starting compounds have amino, carboxy, hydroxy as substituents, a protecting groups which are generally used in the peptide chemistry or the like may be introduced into these groups and, after reaction, a desired compound can be obtained by removing protecting groups if needed.

As a protecting group for amino, for example, formyl or $C_{1-6}$ alkyl-carbonyl (for example, acetyl, propionyl and the like), phenylcarbonyl, $C_{1-6}$ alkoxy-carbonyl (for example, methoxycarbonyl, ethoxycarbonyl and the like), phenyloxycarbonyl, $C_{7-10}$ aralkyloxycarbonyl (for example, benzyloxycarbonyl and the like), trityl, phthaloyl and the like which may have substituents, respectively, are used. As these substituents, halogen atoms (for example, fluorine, chlorine, bromine, iodine and the like), $C_{1-6}$ alkylcarbonyl (for example, acetyl, propionyl, valeryl and the like), nitro and the like are used and the number of substituents is 1 to 3.

As a protecting group for carboxy, for example, $C_{1-6}$ alkyl (for example, methyl, ethyl, propyl, isopropyl, butyl, tert-butyl and the like), phenyl, trityl, silyl and the like which may have substituents, respectively, are used. As these substituents, halogen atoms (for example, fluorine, chlorine, bromine, iodine and the like), formyl, $C_{1-6}$ alkyl-carbonyl (for example, acetyl, propionyl, butylcarbonyl and the like), nitro, $C_{1-6}$ alkyl (for example, methyl, ethyl, tert-butyl and the like), $C_{6-10}$ aryl (for example, phenyl, naphthyl and the like) and the like are used and the number of substituents is 1 to 3.

As a protecting group for hydroxy, for example, $C_{1-6}$ alkyl (for example, methyl, ethyl, propyl, isopropyl, butyl, tert-butyl and the like), phenyl, $C_{7-11}$ aralkyl (for example, benzyl and the like), formyl, $C_{1-6}$ alkyl-carbonyl (for example, acetyl, propionyl and the like), phenyloxycarbonyl, $C_{7-11}$ aralkyloxy-carbonyl (for example, benzyloxycarbonyl and the like), tetrahydropyranyl, tetrahydrofuranyl, silyl and the like which may have substituents, respectively, are used. As these substituents, halogen atoms (for example, fluorine, chlorine, bromine, iodine and the like), $C_{1-6}$ alkyl (for example, methyl, ethyl, tert-butyl and the like), $C_{7-11}$ aralkyl (for example, benzyl and the like), $C_{6-10}$ aryl (for example, phenyl, naphthyl and the like), nitro and the like are used and the number of substituents is 1 to 4.

In addition, as a method of removing a protecting group, the method known per se or a method according to this method is used and, for example, method by treating with an acid, a base, the ultraviolet ray, hydrazine, phenylhydrazine, sodium N-methyldithiocarbamate, tetrabutylammonium fluoride, palladium acetate and the like or a method of reduction is used.

In any cases, Compound (I) can be synthesized by further, optionally, performing the known deprotection, acylation, alkylation, hydrogenation, oxidation, reduction, carbon chain extension and substituent exchange reaction alone or in a combination of two or more of them. As these reactions, the reactions described in Shinjikkenkagakukoza 14, vol. 15, 1977 (Maruzen Press) are adopted.

As the above "alcohols", for example, there are methanol, ethanol, propanol, isopropanol, tert-butanol and the like.

As the above "ethers", for example, there are diethyl ether, diisopropyl ether, diphenyl ether, tetrahydrofuran, dioxane, 1,2-dimethoxyethane and the like.

As the above "halogenated hydrocarbons", for example, there are dichloromethane, chloroform, 1,2-dichloroethane, carbon tetrachloride and the like.

As the above "aliphatic hydrocarbons", for example, there are hexane, pentane, cyclohexane and the like.

As the above "aromatic hydrocarbons", for example, there are benzene, toluene, xylene, chlorobenzene and the like.

As the above "aromatic amines", for example, there are pyridine, lutidine, quinoline and the like.

As the above "amides", for example, there are N,N-dimethylformamide, N,N-dimethylacetamide, hexamethylphosphoric triamide and the like.

As the above "ketones", for example, there are acetone, methyl ethyl ketone and the like.

As the above "sulfoxides", for example, there are dimethyl sulfoxide and the like.

As the above "nitriles", for example, acetonitrile, propionitrile and the like.

As the above "organic acids", for example, there are acetic acid, propionic acid, trifluoroacetic acid and the like.

When a desired product is obtained in a free form by the above reaction, it may be converted into a salt according to the conventional method or, when a desired product is obtained as a salt, it can be converted into a free form or another salt according to the conventional method. Compound (I) thus obtained can be isolated and purified from the reaction solution by the known means, for example, transsolvation, concentration, solvent extraction, fractional distillation, crystallization, recrystallization, chromatography and the like.

When Compound (I), (Ia), (Ib), (Ic) or (Id) is present as a configurational isomer, diastereomer, conformer or the like, each can be optionally isolated by the above separation and purification means. In addition, Compound (I), (Ia), (Ib), (Ic) or (Id) is in the form of its racemate, they can be separated into S- and R-forms by any conventional optical resolution.

When Compound (I), (Ia), (Ib), (Ic) or (Id) exists as a stereoisomer, both the isomers alone and mixtures of each isomers are included in the scope of the present invention.

In addition, Compound (I), (Ia), (Ib), (Ic) or (Id) may be hydrated or anhydrous.

Compound (I) may be labeled with an isotope (for example, $^3$H, $^{14}$C, $^{35}$S) or the like.

A prodrug of Compound (I) refers to a compound which is converted into Compound (I) by an enzyme, gastric acid or the like under the physiological conditions, that is, a compound which undergoes enzymatic oxidation, reduction, hydrolysis or the like to be converted into Compound (I), and a compound which undergoes hydrolysis or the like by gastric acid or the like to be converted into Compound (I). As a prodrug of Compound (I), there are a compound in which an amino group of Compound (I) is acylated, alkylated or phosphorylated (for example, a compound in which an amino group of Compound (I) is eicosanoylation, alanylation, pentylaminocarbonylation, (5-methyl-2-oxo-1,3-dioxolen-4-yl)methoxycarbonylation, tetrahydrofuranylation, pyrrolidinylmethylation, pivaloyloxymethylation, tert-butylation); a compound in which a hydroxy group of Compound (I) is acylated, alkylated, phosphorylated or boronylated (for example, a compound in which a hydroxy group of Compound (I) is acetylated, palmitoylated, propanoylated, pivaloylated, succinylated, fumarylated, alanylated, dimethylaminomethylcarbonylated); a compound in which a carboxy group of Compound (I) is esterified or amidated (a compound in which a carboxy group of Compound (I) is ethylesterified, phenylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonylethylesterified, methylamidated); and the like. These compounds can be prepared from Compound (I) by methods known per se.

Alternatively, a prodrug of Compound (I) may be a compound which is changed into Compound (I), (Ia), (Ib), (Ic) or (Id) under the physiological conditions described in "Iyakuhin no kaihatsu", published by Hirokawashoten in 1990, vol.7, Molecular Design, pages 163-198.

Compound (I) of the present invention shows the high affinity for adenosine receptor, in particular, $A_3$ receptor and has low toxicity and minimal side effect and, therefore, is useful as a safe drug.

A pharmaceutical composition of the present invention containing Compound (I) shows an excellent adenosine $A_3$ receptor antagonistic activity to a mammal (for example, mouse, rat, hamster, rabbit, cat, dog, cow, sheep, monkey, human being and the like) and is also excellent in (oral) absorption, (metabolism) stability and the like and, therefore, can be used as an agent for preventing or treating adenosine $A_3$ receptor-related diseases, for example, asthma, allergic disease, inflammation, Addison's disease, autoimmune hemolytic anemia, Crohn's disease, psoriasis, rheumatism, central nervous disease (for example, cerebrovascular disease such as cerebral hemorrhage, cerebral infarction, head trauma, spinal trauma, brain edema, multiple sclerosis and the like), neurodegenerative disease (for example, Alzheimer's disease, Parkinson's syndrome, amyotrophic lateral sclerosis (ALS)), diabetes and the like. Preferably, Compound (I) is an agent for preventing or treating central nervous disease, asthma, allergic disease and the like.

Compound (I) of the present invention also shows an excellent p38 MAP kinase inhibitory activity and TNF-α inhibitory activity (TNF-α production inhibitory activity, TNF-α action inhibitory activity) and is also useful as a safe drug based these activities.

For example, a pharmaceutical composition of the present invention containing Compound (I) can be used as an agent for preventing or treating p38 MAP kinase related diseases and TNF-α related disease, for example, arthritis (for example, rheumatoid arthritis, osteoarthritis, rheumatoid spondylitis, gouty arthritis, synovitis), toxemia (for example, sepsis, septic shock, endotoxin shock, Gram-negative sepsis, toxic shock syndrome), inflammatory bowel disease (for example, Crohn's disease, ulcerative colitis), inflammatory pulmonary disease (for example, chronic pneumonia, silicosis, pulmonary sarcoidosis, pulmonary tuberculosis), or cachexia (for example, cachexia derived from infection, carcinocachexia, cachexia derived from acquired immunodeficiency syndrome (AIDS)), arteriosclerosis, Creutzfeldt-Jakob disease, virus infection (for example, virus infection such as cytomegalovirus, influenzavirus, herpesvirus and the like), atopic dermatitis, systemic lupus erythematosus, AIDS encephalopathy, meningitis, angina, cardiac infarction, congestive heart failure, hepatitis, transplantation, dialysis hypotension, disseminated intravascular coagulation and the like to a mammal (for example, mouse, rat, hamster, rabbit, cat, dog, cow, sheep, monkey, human being and the like). Preferably, Compound (I) is used as an agent for preventing or treating rheumatism and the like.

A preparation of the present invention containing Compound (I) has low toxicity and can be safely administered orally or parenterally (for example, locally, rectally or intravenously or the like) as it is or by mixing Compound (I) with a pharmacologically acceptable carrier into, for example, pharmaceutical preparations such as tablet (including dragee, film coated-tablet and the like), powders, granules, capsules (including soft capsules), solutions, injections, suppositories, sustained releasing preparations and the like according to the method known per se normally used in preparation of pharmaceutical preparations. A content of Compound (I) in a preparation of the present invention is about 0.01 to 100% by weight relative to the whole preparation. A dose is different depending upon an administration subject, route of administration, diseases and the like and the preparation may be administered, as an adenosine $A_3$ receptor antagonistic agent, for example, as an oral agent to an asthma patient (weight about 60 kg), about 0.1 to about 30 mg active ingredient (Compound (I))/kg weight per day, preferably about 1 to 20 mg/kg weight per day, once or a few times per day.

As a pharmacologically acceptable carrier which may be used for preparing a preparation of the present invention, there are the conventional various organic or inorganic carriers as a pharmaceutical material, for example, excipient, lubricant, binder and disintegrating agent in solid preparations, or solvent, solubilizing agent, suspending agent, isotonicity, buffer and soothing agent in liquid preparations. Further, if needed, additives such as the conventional preservative, antioxidant, colorant, sweeting agent, adsorbing agent, wetting agent and the like can be appropriately used at an appropriate amount.

As an excipient, for example, there are lactose, sucrose, D-mannitol, starch, corn starch, crystalline cellulose, light silicic acid anhydride and the like.

As a lubricant, for example, there are magnesium stearate, calcium stearate, talc, colloidal silica and the like.

As a binder, for example, there are crystalline cellulose, sucrose, D-mannitol, dextrin, hydroxypropyl cellulose, hydroxypropyl methyl cellulose, polyvinylpyrrolidone, starch, sucrose, gelatin, methyl cellulose, sodium carboxymethyl cellulose and the like.

As a disintegrating agent, for example, there are starch, carboxymethyl cellulose, calcium carboxymethyl cellulose, sodium carboxymethyl starch, L-hydroxypropyl cellulose and the like.

As a solvent, for example, there are water for injection, alcohol, propylene glycol, macrogol, sesame oil, corn oil, olive oil and the like.

As a solubilizing agent, for example, there are polyethylene glycol, propylene glycol, D-mannitol, benzyl benzoate, ethanol, trisaminomethane, cholesterol, triethanolamine, sodium carbonate, sodium citrate and the like.

As a suspending agent, for example, there are surfactants such as stearyl triethenolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, sodium carboxymethyl cellulose, methyl cellulose, hydroxymethyl cellulose, hydroxyethyl cellulose, hydoxypropyl cellulose and the like.

As an isotonicity, for example, there are glucose, D-sorbitol, sodium chloride, glycerin, D-mannitol and the like.

As a buffer, for example, there are buffering solutions such as phosphate, acetate, carbonate, citrate and the like.

As a soothing agent, for example, there are benzyl alcohol and the like.

As a preservative, for example, there are p-hydroxybenzoates, chlorobutanol, benzyl alcohol, phenethyl alcohol, dehydroacetic acid, sorbic acid and the like.

As an antioxidant, for example, there are sulfites, ascorbic acid, α-tocopherol and the like.

The present invention will be explained in detail by way of the following Reference Examples, Examples, Preparation Examples and Test Examples but these are more examples and not limit the present invention and can be varied without departing the scope of the present invention.

"Room temperature" in the following Reference Examples and Examples indicates normally about 10° C. to about 35° C. "%" indicates percentage by weight unless otherwise indicated, provided that yield represents mol/mol %.

Abbreviations used elsewhere indicate the following meanings:
s: singlet
d: doublet
t: triplet
q: quartet
dd: double doublet
ddd: double double doublet
dt: double triplet
br: broad
J: coupling constant
Hz: Hertz
$CDCl_3$: deuterated chloroform
$^1$H-NMR: proton nuclear magnetic resonance spectrum
Me: methyl

EXAMPLES

Reference Example 1

2-phenylmethyloxy-4-methylpyridine

Sodium hydride (60% paraffin dispersion, 5.0 g, 120 mmol) was washed with hexane (5 mL) twice and suspended in tetrahydrofuran (200 mL). To this suspension was added dropwise a solution of benzyl alcohol (14 g, 120 mmol) in tetrahydrofuran (50 mL) at 0° C. and then, the mixture was allowed to warm up to room temperature with stirring for 15 minutes. To this solution was added a solution of 2-bromo-4-methylpyridine (19.5 mL, 110 mmol) in tetrahydrofuran (50 mL) and heated to reflux for 14 hours. To the reaction mixture was added water (200 mL) and extracted with ethyl acetate. The extract was dried and the solvent was distilled off. The crude product was distilled under reduced pressure to obtain 13 g of the title compound (67 mmol, yield 67%).

Boiling point 116-118° C. (400 Pa)

$^1$H-NMR ($CDCl_3$) δ: 2.30 (3H, s), 5.37 (2H, s), 6.63 (1H, s), 6.72 (1H, d, J=5.1 Hz), 7.29-7.50 (5H, m), 8.03 (1H, d, J=5.1 Hz)

Reference Example 2

N-(3,5-dimethylbenzoyl)propyleneimine 3,5-Dimethylbenzoic acid (25 g, 0.17 mol) and N,N-dimethylformamide (0.1 mL) were added to thionyl chloride (50 mL) at 0° C. The mixture was heated to reflux for 2 hours. The excess thionyl chloride was distilled off under reduced pressure and toluene (50 mL) was added to the residue. Toluene was distilled off under reduced pressure to obtain oily 3,5-dimethylbenzoyl chloride. A solution of propyleneimine (14 mL, 0.18 mol) in tetrahydrofuran (160 mL) was added to 1N aqueous sodium hydroxide (180 mL). To the solution was added dropwise 3,5-dimethylbenzoyl chloride at 0° C. After complete addition, the mixture was further stirred for 30 minutes. The reaction mixture was extracted with ethyl acetate. The extract was dried and the solvent was distilled off to obtain 31 g of the title compound (0.16 mol, yield 99%).

Oily Product $^1$H-NMR ($CDCl_3$) δ: 1.39 (3H, d, J=5.5 Hz), 2.13 (1H, d, J=3.7 Hz), 2.37(6H, s), 2.47-2.62 (2H, m), 7.19 (1H, s), 7.64 (2H, s)

Reference Example 3

1-(3,5-dimethylphenyl)-2-(2-phenylmethyloxy-4-pyridyl)ethanone

A solution of diisopropylamine (9.6 mL, 69 mmol) in anhydrous tetrahydrofuran (60 mL) was cooled to −50° C. and a solution of 1.6 M n-butyllithium in hexane (43 mL, 69 mmol) was added dropwise with stirring. After complete addition, the mixture was stirred for 10 minutes and subsequently a solution of 2-phenylmethyloxy-4-methylpyridine (12 g, 62 mmol) in anhydrous tetrahydrofuran (12 mL) at −30° C. After additional stirring for 1 h, a solution of N-(3,5-dimethylbenzoyl)propyleneimine (12 g, 62 mmol) in anhydrous tetrahydrofuran (12 mL) was added at −30° C. After complete addition, the resulting mixture was allowed to warm up to room temperature and the mixture was stirred for 2 hours. Water (60 mL) was added to the reaction mixture and extracted with ethyl acetate. The extract was washed with water, dried and the solvent was distilled off. The residue was purified by silica gel column chromatography (hexane-ethyl acetate, 5:1) to obtain 9.1 g of the title compound (27 mmol, yield 44%).

Oily Product $^1$H-NMR ($CDCl_3$) δ: 2.37 (6H,s), 4.20 (2H, s), 5.37 (2H, s), 6.72 (1H, s), 6.81 (1H, d, J=5.1 Hz), 7.22 (1H, s), 7.30-7.49 (5H, m), 7.59 (2H, s), 8.12 (1H, d, J=5.1 Hz)

Reference Example 4

2-bromo-1-(3,5-dimethylphenyl)-2-(2-phenylmethyloxy-4-pyridyl)ethanone hydrobromide 1-(3,5-Dimethylphenyl)-2-(2-phenylmethyloxy-4-pyridyl)ethanone (3.3 g, 10 mmol) was dissolved in acetic acid (10 mL) and bromine (0.51 mL, 10 mmol) was added to the solution and stirred at room temperature for 30 minutes. The precipitated crude crystals were collected by filtration and washed with diethyl ether to obtain 4.8 g of the title compound (9.8 mmol, yield 98%).

mp. 88-90° C.

Reference Example 5

N-(4-methoxybenzoyl)propyleneimine

A solution of propyleneimine (25 mL, 0.36 mol) in tetrahydrofuran (200 mL) was added to 2N aqueous sodium hydroxide (180 mL). To this mixture was added dropwise a solution of 4-methoxybenzoyl chloride (51 g, 0.30 mol) in tetrahydrofuran (100 mL) at 0° C. After complete addition, the mixture was stirred further for 30 minutes. The reaction mixture was extracted with ethyl acetate. The extract was dried and the solvent was distilled off to obtain 49 g of the title compound (0.26 mol, yield 86%).

Oily Product $^1$H-NMR (CDCl$_3$) δ: 1.39 (3H, d, J=5.6 Hz), 2.11 (1H, d, J=3.0 Hz), 2.51-2.57 (2H, m), 3.87 (3H, s), 6.94 (2H, d, J=8.8 Hz), 8.00 (2H, d, J=8.8 Hz)

Reference Example 6

1-(4-methoxyphenyl)-2-(2-tert-butoxycarbonylamino-4-pyridyl)ethanone

A solution of 2-tert-butoxycarbonylamino-4-methylpyridine (20 g, 97 mmol) in anhydrous tetrahydrofuran (300 mL) was cooled to −78° C. and a solution of 1.6 M n-butyllithium in hexane (140 mL, 0.22 mol) was added dropwise with stirring. After complete addition, the mixture was stirred at room temperature for 30 minutes. And then, the mixture was cooled to −78° C. A solution of N-(4-methoxybenzoyl)propyleneimine in anhydrous tetrahydrofuran (50 mL) was added dropwise to the mixture. After complete addition, the mixture was stirred at room temperature for 2 hours. Water (100 mL) and diisopropyl ether (300 mL) were added to the reaction mixture and the resulting crude crystals were collected by filtration. The crude crystals were recrystallized from tetrahydrofuran-hexane to obtain 23 g of the title compound (67 mmol, yield 69%).

mp. 187-190° C.

Reference Example 7

4-[2-amino-4-(4-methoxyphenyl)-1,3-thiazol-5-yl]-2-pyridylamine

Bromine (0.68 mL, 13 mmol) was added to a solution of 1-(4-methoxyphenyl)-2-(2-tert-butoxycarbonylamino-4-pyridyl)ethanone (4.5 g, 13 mmol) in acetic acid (100 mL) and the mixture was stirred at room temperature for 30 minutes. The reaction mixture was concentrated. The residue was dissolved in acetonitrile (40 mL) and to the solution was added thiourea (1.1 g, 14 mmol) and triethylamine (1.9 mL, 14 mmol) were added and the mixture was stirred at 80° C. for 2 hours. The reaction mixture was cooled to room temperature and concentrated. A saturated aqueous sodium hydrogencarbonate (200 mL) was added to the residue and the resulting solid was collected by filtration and washed with water. 2N hydrochloric acid (35 mL) was added to the solids and the mixture was stirred at 100° C. for 45 minutes. The reaction mixture was cooled to room temperature and, thereafter, 8N aqueous sodium hydroxide (10 mL) and a saturated aqueous solution of sodium hydrogencarbonate (100 mL) were added. The resulting crude crystals were collected by filtration, and were washed with water. The crude crystals were recrystallized from ethanol to obtain 2.7 g of the title compound (9.1 mmol, yield 69%).

mp. 251-254° C.

Reference Example 8

2-(2-amino-4-pyridyl)-1-(4-methoxyphenyl)ethanone 2N-hydrochloric acid (30 mL) was added to 1-(4-methoxyphenyl)-2-(2-tert-butoxycarbonylamino-4-pyridyl)ethanone (6.1 g, 18 mmol) and the mixture was stirred at 100° C. for 2 hours. The reaction mixture was cooled to room temperature and, thereafter, 8N-aqueous sodium hydroxide (10 mL) was added. The resulting crude crystals were filtered and washed with water. The crude crystals were recrystallized from tetrahydrofuran-hexane to obtain 4.0 g of the title compound (16 mmol, yield 92%).

mp. 170-174° C.

Reference Example 9

2-(2-benzoylamino-4-pyridyl)-1-(4-methoxyphenyl)ethanone

Benzoyl chloride (4.4 g, 31 mmol) and 4-dimethylaminopyridine (0.57 g, 4.7 mmol) were added to a solution of 2-(2-amino-4-pyridyl)-1-(4-methoxyphenyl)ethanone (3.8 g, 16 mmol) in N,N-dimethylacetamide (80 mL) and the mixture was stirred at 70° C. for 12 hours. After the reaction mixture was cooled to room temperature, water (50 mL) was added. The mixture was extracted with ethyl acetate and the organic layer was washed with a saturated aqueous solution of sodium chloride. The layer was dried over magnesium sulfate, filtered and concentrated. The residue was dissolved in tetrahydrofuran (80 mL) and methanol (20 mL) and 1N-aqueous solution of sodium hydroxide (50 mL) was added. The mixture was stirred at room temperature for 3 hours. The reaction mixture was concentrated and water (100 mL) was added. The mixture was extracted with ethyl acetate and the organic layer was washed with a saturated aqueous solution of sodium chloride. The layer was dried over magnesium sulfate, filtered and concentrated. The residue was recrystallized from ethyl acetate-hexane to obtain 3.1 g of the title compound (8.9 mmol, yield 57%).

mp. 136-139° C.

Reference Example 10

1-(3,5-dimethylphenyl)-2-(2-tert-butoxycarbonylamino-4-pyridyl)ethanone

A solution of 2-tert-butoxycarbonylamino-4-methylpyridine (17 g, 82 mmol) in anhydrous tetrahydrofuran (250 mL) was cooled to −78° C. and a 1.6N solution of n-butyllithium in hexane (120 mL, 0.19 mol) was added dropwise with stirring. After complete addition, the mixture was stirred at 0° C. for 30 minutes and cooled to −78° C. A solution of N-(3,5-dimethylbenzoyl)propyleneimine (21 g, 0.11 mol) in anhydrous tetrahydrofuran (50 mL) was added dropwise to the mixture. After complete addition, the mixture was stirred at room temperature for 2 hours. Water (100 mL) was added to the reaction mixture and extracted with ethyl acetate. The organic layer was washed with a saturated aqueous solution of sodium chloride, dried over magnesium sulfate, filtered and concentrated. The residue was recrystallized from tetrahydrofuran-hexane to obtain 13 g of the title compound (37 mmol, yield 46%).

mp. 133-136° C.

Reference Example 11

2-(2-amino-4-pyridyl)-1-(3,5-dimethylphenyl)ethanone 2N-hydrochloric acid (50 mL) was added to 1-(3,5-dimethylphenyl)-2-(2-tert-butoxycarbonylamino-4-pyridyl)ethanone (12 g, 36 mmol) and the mixture was stirred at 100° C. for 1 hour. After the reaction mixture was cooled to room temperature, an 8N aqueous solution of sodium hydroxide (15 mL) was added and extracted with ethyl acetate. The organic layer was washed with a saturated aqueous solution of sodium chloride, dried over magnesium sulfate, filtered and concentrated. The residue was recrystallized from ethyl acetate to obtain 6.8 g of the title compound (28 mmol, yield 77%).

mp. 123-126° C.

Reference Example 12

2-(2-benzoylamino-4-pyridyl)-1-(3,5-dimethylphenyl)ethanone

Benzoyl chloride (7.5 g, 53 mmol) and 4-dimethylaminopyridine (1.0 g, 8.3 mmol) were added to a solution of 2-(2-amino-4-pyridyl)-1-(3,5-dimethylphenyl)ethanone (6.4 g, 27 mmol) in N,N-dimethylacetamide (100 mL) and the mixture was stirred at 70° C. for 12 hours. After the reaction mixture was cooled to room temperature, water (50 mL) was added. The mixture was extracted with ethyl acetate. The organic layer was washed with a saturated aqueous solution of sodium chloride. The layer was dried over magnesium sulfate, filtered and concentrated. The residue was dissolved in a mixed solvent of tetrahydrofuran (150 mL) and methanol (40 mL) and 1N aqueous solution of sodium hydroxide (50 mL) was added. The mixture was stirred at room temperature for 3 hours. The reaction mixture was concentrated, water (100 mL) was added and neutralized with 2N-hydrochloric acid and a saturated aqueous solution of sodium hydrogencarbonate. The mixture was extracted with ethyl acetate and the organic layer was washed with a saturated aqueous solution of sodium chloride. The layer was dried over magnesium sulfate, filtered and concentrated. The residue was purified by silica gel column chromatography (hexane-ethyl acetate, 2:1) to obtain 6.4 g of the title compound (19 mmol, yield 70%).

Oily Product
$^1$H-NMR (CDCl$_3$) δ: 2.39 (6H, s), 4.33 (2H, s), 6.98-7.01 (1H, m), 7.23 (1H, s), 7.45-7.58 (3H, m), 7.63 (2H, s), 7.89-7.94 (2H, m), 8.21 (1H, d, J=5.2 Hz), 8.36 (1H, s), 8.71 (1H, br)

Reference Example 13

According to Reference Example 5 and using 3-methylbenzoyl chloride and 3-methoxybenzoyl chloride, respectively, instead of 4-methoxybenzoyl chloride, the following Reference Example compounds 13-1 and 13-2 were synthesized.

Reference Example Compound 13-1

N-(3-methylbenzoyl)propyleneimine

Oily Product
$^1$H-NMR (CDCl$_3$) δ: 1.39 (3H, d, J=5.5 Hz), 2.14 (1H, d, J=3.3 Hz), 2.41 (3H, s), 2.51-2.66 (2H, m), 7.32-7.39 (2H, m), 7.79-7.87 (2H, m).

Reference Example Compound 13-2

N-(3-methoxybenzoyl)propyleneimine

Oily Product
$^1$H-NMR (CDCl$_3$) δ: 1.40 (3H, d, J=5.9 Hz), 2.14 (1H, d, J=2.9 Hz), 2.52-2.65 (2H, m), 3.86 (3H, s), 7.10 (1H, ddd, J=8.4, 2.6, 1.1 Hz), 7.37 (1H, dd, J=8.4, 7.3 Hz), 7.55 (1H, dd, J=2.6, 1.5 Hz), 7.63 (1H, ddd, J=7.3, 1.5, 1.1 Hz)

Reference Example 14

According to Reference Example 6 and using N-(3-methylbenzoyl)propyleneimine instead of N-(4-methoxybenzoyl)propyleneimine, the following Reference Example compound 14 was synthesized.

Reference Example Compound 14

2-(2-tert-butoxycarbonylamino-4-pyridyl)-1-(3-methylphenyl)ethanone mp. 144-146° C.

Reference Example 15

4-(methylthio)thiobenzamide

4-Methylthiobenzonitrile (12 g) was dissolved in a 4N solution of hydrogen chloride in ethyl acetate (130 mL). To this solution was added O,O-diethyl dithiophosphate (15 mL) and the mixture was stirred at room temperature for 22 hours. Water (100 mL) was added to the reaction mixture and extracted with ethyl acetate. After the insoluble materials were filtered off, the filtrate was washed with a saturated aqueous solution of sodium chloride and dried and, thereafter, the solvent was distilled off. The residue was recrystallized from ethyl acetate to obtain 10 g of the title compound (yield 67%).

mp. 176-178° C.

Reference Example 16

According to Reference Example 15 and using 4-fluorobenzonitrile, 2-chlorobenzonitrile, butyronitrile and valeronitrile, respectively, instead of 4-methylthiobenzonitrile, the following Reference Example Compounds 16-1-16-4 were synthesized.

Reference Example Compound 16-1

4-fluorothiobenzamide mp. 156-157° C.

Reference Example Compound 16-2

2-chlorothiobenzamide mp. 58-59° C.

Reference Example Compound 16-3

Thiobutyramide

Oily Product
$^1$H-NMR (CDCl$_3$) δ: 0.99 (3H, t, J=7.6 Hz), 1.72-1.93 (2H, m), 2.64 (2H, t, J=7.6 Hz), 7.02 (1H, br s), 7.77 (1H, br s)

Reference Example Compound 16-4

Thiovaleramide

Oily Product
$^1$H-NMR (CDCl$_3$) δ: 0.94 (3H, t, J=7.3 Hz), 1.31-1.49 (2H, m), 1.68-1.83 (2H, m), 2.67 (2H, t, J=7.7 Hz), 6.92 (1H, br s), 7.73 (1H, br s)

Reference Example 17

4-[2-methyl-4-(3-methylphenyl)-1,3-thiazol-5-yl]-2-pyridylamine

Bromine (1.0 mL, 18 mmol) was added to a solution of 2-(2-tert-butoxycarbonylamino-4-pyridyl)-1-(3-methylphenyl)ethanone (6.0 g, 18 mmol) in acetic acid (50 mL) and the mixture was stirred at room temperature for 30 minutes. The reaction mixture was concentrated. The residue was dissolved in N,N-dimethylformamide (50 mL) and to the solution was added thioacetamide (1.4 g, 19 mmol) and the resulting mixture was stirred at room temperature for 20 hours. To the reaction mixture was added a saturated aqueous solution of sodium hydrogencarbonate (200 mL) and extracted with ethyl acetate. The extract was dried and the solvent was distilled off. 2N-hydrochloric acid (30 mL) was added to the resulting solid and the mixture was stirred at 100° C. for 1 hour. After the reaction mixture was cooled to room temperature, the mixture was basified with a 2N aqueous solution of sodium hydroxide (200 mL) and a saturated aqueous solution of sodiumhydrogen carbonate. The resulting mixture was extracted with ethyl acetate and the extract was washed with water. The extract was dried and concentrated. The residue was purified by silica gel column chromatography (ethyl acetate) to obtain 2.8 g of the title compound (yield 54%).

mp. 152-153° C.

Reference Example 18

According to Reference Example 17 and using thiopropionamide and 4-(methylthio)thiobenzamide, respectively, instead of thioacetamide, the following Reference Example compounds 18-1 and 18-2 were synthesized.

Reference Example Compound 18-1

4-[2-ethyl-4-(3-methylphenyl)-1,3-thiazol-5-yl]-2-pyridylamine mp. 144-146° C.

Reference Example Compound 18-2

4-[4-(3-methylphenyl)-2-(4-methylthiophenyl)-1,3-thiazol-5-yl]-2-pyridylamine mp. 181-183° C.

Reference Example 19

According to Reference Example 17 and using 1-(4-methoxyphenyl)-2-(2-tert-butoxycarbonylamino-4-pyridyl)ethanone instead of 2-(2-tert-butoxycarbonylamino-4-pyridyl)-1-(3-methylphenyl)ethanone, the following Reference Example Compound 19 was synthesized.

Reference Example Compound 19

4-[4-(4-methoxyphenyl)-2-methyl-1,3-thiazol-5-yl]-2-pyridylamine mp. 140-141° C.

Reference Example 20

According to Reference Example 8 and using 2-(2-tert-butoxycarbonylamino-4-pyridyl)-1-(3-methylphenyl)ethanone instead of 1-(4-methoxyphenyl)-2-(2-tert-butoxycarbonylamino-4-pyridyl)ethanone, the following Reference Example Compound 20 was synthesized.

Reference Example Compound 20

2-(2-amino-4-pyridyl)-1-(3-methylphenyl)ethanone mp. 119-120° C.

Reference Example 21

2-(2-amino-4-pyridyl)-2-bromo-1-(3-methylphenyl)ethanone hydrobromide

Bromine (3.2 mL, 62 mol) was added to a solution of 2-(2-tert-butoxycarbonylamino-4-pyridyl)-1-(3-methylphenyl)ethanone (20 g, 61 mmol) in acetic acid (60 mL) and the mixture was stirred at 80° C. for 2 hours. After the reaction mixture was cooled to room temperature, the precipitate was filtered to obtain 19 g (yield 81%) of the title compound.

mp. 182-185° C.

Reference Example 22

According to Reference Example 9 and using 2-(2-amino-4-pyridyl)-1-(3-methylphenyl)ethanone instead of 2-(2-amino-4-pyridyl)-1-(4-methoxyphenyl)ethanone, the following Reference Example Compound 22 was synthesized.

Reference Example Compound 22

N-[4-[2-(3-methylphenyl)-2-oxoethyl]-2-pyridyl]benzamide mp. 67-69° C.

Reference Example 23

4-[2-(4-fluorophenyl)-4-(3-methylphenyl)-1,3-thiazol-5-yl]-2-pyridylamine 2-(2-Amino-4-pyridyl)-2-bromo-1-(3-methylphenyl)ethanone hydrobromide (5.0 g, 13 mmol) was dissolved in N,N-dimethylformamide (40 mL), to the solution was added 4-fluorothiobenzamide (2.1 g, 13 mmol) and the mixture was stirred at room temperature for 16 hours. A saturated aqueous solution of sodium hydrogencarbonate (200 mL) was added to the reaction mixture and the mixture was extracted with ethyl acetate. The extract was dried and the solvent was distilled off. The residue was recrystallized from ethanol to obtain 3.9 g (11 mmol, yield 83%) of the title compound.

mp. 160-162° C.

Reference Example 24

According to Reference Example 23 and using 2-chlorothiobenzamide, thiobutyramide and thiovaleramide, respectively, instead of 4-fluorothiobenzamide, the following Reference Example Compounds 24-1-24-3 were synthesized.

Reference Example Compound 24-1

4-[2-(2-chlorophenyl)-4-(3-methylphenyl)-1,3-thiazol-5-yl]-2-pyridylamine mp. 175-177° C.

Reference Example Compound 24-2

4-[4-(3-methylphenyl)-2-propyl-1,3-thiazol-5-yl]-2-pyridylamine mp. 113-115° C.

Reference Example Compound 24-3

4-[2-butyl-4-(3-methylphenyl)-1,3-thiazol-5-yl]-2-pyridylamine

Oily Product
$^1$H-NMR (CDCl$_3$) δ: 0.98 (3H, t, J=7.3 Hz), 1.39-1.59 (2H, m), 1.74-1.92 (2H, m), 2.34 (3H, s), 3.04 (2H, t, J=7.4 Hz), 4.14 (2H, br s), 6.44 (1H, s), 6.56 (1H, dd, J=5.1, 1.5 Hz), 7.09-7.26 (3H, m), 7.41 (1H, s), 7.96 (1H, d, J=5.4 Hz)

Reference Example 25

2-fluoro-4-methylpyridine

The title compound was obtained in the same manner as described in Journal of Medicinal Chemistry, vol. 33, 1667-1675, 1990.

Boiling point 82-86° C. (10 kPa)

Reference Example 26

2-(2-fluoro-4-pyridyl)-1-(3-methylphenyl)ethanone

A solution of diisopropylamine (44 mL, 0.31 mol) in anhydrous tetrahydrofuran (300 mL) was cooled to −78° C. under argon atmosphere and a 1.6M solution of n-butyllithium in hexane (190 mL, 0.31 mol) was added dropwise to the solution. After complete addition, the mixture was stirred for 10 minutes and subsequently a solution of 2-fluoro-4-methylpyridine (34.5 g, 0.31 mol) in anhydrous tetrahydrofuran (30 mL) was added. The reaction mixture was stirred at −10° C. for 30 minutes. The reaction solution was cooled to −78° C. and a solution of N-(3-methylbenzoyl)propyleneimine (52 g, 0.30 mol) in anhydrous tetrahydrofuran (30 mL) was added dropwise. After complete addition, the mixture was stirred at room temperature for 2 hours. Water (100 mL) was added to the reaction mixture and the mixture was extracted with ethyl acetate. The extract was washed with water, dried and the solvent was distilled off. The residue was recrystallized from isopropyl ether to obtain 35 g (yield 52%) of the title compound.

mp. 66-67° C.

Reference Example 27

According to Reference Example 26 and using N-(3-methoxybenzoyl)propyleneimine instead of N-(3-methylbenzoyl)propyleneimine, the following Reference Example compound 27 was synthesized.

Reference Example Compound 27

2-(2-fluoro-4-pyridyl)-1-(3-methoxyphenyl)ethanone

Oily Product
$^1$H-NMR (CDCl$_3$) δ: 3.86 (3H, s), 4.31 (2H, s), 6.86 (1H, s), 7.03-7.19 (2H, m), 7.31-7.59 (3H, m), 8.18 (1H, d, J=5.6 Hz)

Reference Example 28

[5-(2-fluoro-4-pyridyl)-4-(3-methylphenyl)-1,3-thiazol-2-yl]amine

Bromine (1.9 mL, 37 mmol) was added to a solution of 2-(2-fluoro-4-pyridyl)-1-(3-methylphenyl)ethanone (8.5 g, 37 mmol) in acetic acid (50 mL) and the mixture was stirred at room temperature for 1 hour. The reaction mixture was concentrated. Triethylamine (5.2 mL, 37 mmol) was added to a mixture of this residue and thiourea (3.0 g, 40 mmol) in acetonitrile (50 mL) and the mixture was stirred at 80° C. for 2 hours. A saturated aqueous solution of sodium hydrogencarbonate (50 mL) was added to the reaction mixture and the precipitated solid was collected by filtration. After the resulting solid was washed with water, it was dried. The crude crystals were recrystallized from ethanol to obtain 3.7 g (yield 35%) of the title compound.

mp. 214-218° C.

Reference Example 29

According to Reference Example 28 and using 2-(2-fluoro-4-pyridyl)-1-(3-methoxyphenyl)ethanone instead of 2-(2-fluoro-4-pyridyl)-1-(3-methylphenyl)ethanone, the following Reference Example Compound 29 was synthesized.

Reference Example Compound 29

[5-(2-fluoro-4-pyridyl)-4-(3-methoxyphenyl)-1,3-thiazol-2-yl]amine mp. 190-191° C.

Reference Example 30

5-(2-fluoro-4-pyridyl)-4-(3-methylphenyl)-2-(4-methylthiophenyl)-1,3-thiazole

Bromine (2.7 mL, 52 mmol) was added to a solution of 2-(2-fluoro-4-pyridyl)-1-(3-methylphenyl)ethanone (12 g, 53 mmol) in acetic acid (90 mL) and the mixture was stirred at room temperature for 2 hours. The reaction mixture was concentrated. This residue was dissolved in N,N-dimethylformamide (60 mL), 4-(methylthio)thiobenzamide (9.6 g, 52 mmol) was added and the mixture was stirred at room temperature for 15 hours. A saturated aqueous solution of sodium hydrogencarbonate (100 mL) was poured into the reaction mixture and the mixture was extracted with ethyl acetate. The extract was washed with water, dried and the solvent was distilled off. The residue was purified by silica gel column chromatography (hexane:ethyl acetate, 4:1) to obtain 4.7 g (yield 23%) of the title compound.

mp. 97-100° C.

Reference Example 31

5-(2-fluoro-4-pyridyl)-4-(3-methylphenyl)-2-(4-methylsulfonylphenyl)-1,3-thiazole To a solution of 5-(2-fluoro-4-pyridyl)-4-(3-methylphenyl)-2-(4-methylthiophenyl)-1,3-thiazole (2.7 g, 6.9 mmol) in N,N-dimethylformamide (60 mL) was added m-chloroperbenzoic acid (3.3 g, 14 mmol) and the mixture was stirred at room temperature for 1 hour. An 8N aqueous solution of sodium hydroxide was added to the reaction mixture and the resulting solid was collected by filtration. This solid was recrystallized from ethanol to obtain 2.5 g (yield 85%) of the title compound.

mp. 196-199° C.

Example 1

[4-(3,5-dimethylphenyl)-5-(2-phenylmethyloxy-4-pyridyl)-1,3-thiazol-2-yl]amine

Triethylamine (1.4 mL, 10 mmol) was added dropwise to a solution of 2-bromo-1-(3,5-dimethylphenyl)-2-(2-phenylmethyloxy-4-pyridyl)ethanone hydrobromide (4.8 g, 9.8 mmol) and thiourea (0.77 g, 11 mmol) in acetonitrile (40 mL) and the mixture was stirred at room temperature for 3 hours. The solvent was removed under reduced pressure, a saturated aqueous solution of sodium hydrogencarbonate was added to the residue and extracted with ethyl acetate. The organic layer was washed with water, dried and the solvent was distilled off. The resulting crude crystals were recrystallized from ethyl acetate to obtain 2.0 g (5.2 mmol, yield 53%) of the title compound.

mp. 141-143° C.

Example 2

N-[4-[2-benzoylamino-4-(4-methoxyphenyl)-1,3-thiazol-5-yl]-2-pyridyl]benzamide

Benzoyl chloride (0.59 g, 4.2 mmol) and 4-dimethylaminopyridine (0.05 g, 0.4 mmol) were added to a solution of 4-[2-amino-4-(4-methoxyphenyl)-1,3-thiazol-5-yl]-2-pyridylamine (0.42 g, 1.4 mmol) in N,N-dimethylacetamide (10 mL) and the mixture was stirred at 70° C. for 19 hours. After the reaction mixture was cooled to room temperature, a saturated aqueous solution of sodium hydrogencarbonate (50 mL) was added. The resulting crude crystals were collected by filtration and washed with water. The crude crystals were recrystallized from ethanol to obtain 0.26 g (0.51 mmol, yield 37%) of the title compound.

mp. 230-233° C.

Example 3

N-[4-(4-methoxypheny)-5-[2-[(3-pyridylcarbonylamino)]-4-pyridyl]-1,3-thiazol-2-yl]nicotinamide Nicotinoyl chloride hydrochloride (0.72 g, 4.1 mmol) and 4-dimethylaminopyridine (0.05 g, 0.4 mmol) were added to a solution of 4-[2-amino-4-(4-methoxyphenyl)-1,3-thiazol-5-yl]-2-pyridylamine (0.41 g, 1.4 mmol) in N,N-dimethylacetamide (10 mL) and the mixture was stirred at 70° C. for 19 hours. After the reaction mixture was cooled to room temperature, a saturated aqueous solution of sodium hydrogencarbonate (50 mL) was added. The resulting crude crystals were collected by filtration and washed with water. The crude crystals were recrystallized from ethanol to obtain 0.23 g (0.44 mmol, yield 33%) of the title compound.

mp. 229-232° C.

Example 4

N-[4-[2-amino-4-(4-methoxyphenyl)-1,3-thiazol-5-yl]-2-pyridyl]benzamide

Bromine (0.11 mL, 2.1 mmol) was added to a solution of 2-(2-benzoylamino-4-pyridyl)-1-(4-methoxyphenyl)ethanone (0.72 g, 2.1 mmol) in acetic acid (20 mL) at 0° C. and the mixture was stirred at room temperature for 1 hour. The reaction mixture was concentrated. The residue was dissolved in acetonitrile. (20 mL), to the solution were added thiourea (0.17 g, 2.2 mmol) and triethylamine (0.35 mL, 2.5 mmol) and the mixture was stirred at 80° C. for 5 hours. After the reaction mixture was cooled to room temperature, a saturated aqueous solution of sodium hydrogencarbonate (200 mL) was added and the resulting solid was filtered and washed with water. The resulting crude crystals were collected by filtration and washed with water. The crude crystals were recrystallized from ethanol to obtain 0.17 g (0.43 mmol, yield 21%) of the title compound.

mp. 221-224° C.

Example 5

N-[4-[2-amino-4-(3,5-dimethylphenyl)-1,3-thiazol-5-yl]-2-pyridyl]benzamide

Bromine (1.0 mL, 19 mmol) was added to a solution of 2-(2-benzoylamino-4-pyridyl)-1-(3,5-dimethylphenyl)ethanone (6.4 g, 19 mmol) in acetic acid (80 mL) at 0° C. and the mixture was stirred at room temperature for 1 hour. The reaction mixture was concentrated. The residue was dissolved in acetonitrile (100 mL), to the solution were added thiourea (1.5 g, 19 mmol) and triethylamine (2.8 mL, 20 mmol) and the mixture was stirred at 80° C. for 3 hours. After the reaction mixture was cooled to room temperature, a saturated aqueous solution of sodium hydrogencarbonate (200 mL) was added and the resulting solid was collected by filtration and washed with water. The resulting crude crystals were collected by filtration and washed with water. The crude crystals were recrystallized from ethanol to obtain 5.0 g (13 mmol, yield 68%) of the title compound.

mp. 120-123° C.

Example 6

N-[4-[2-amino-4-(3,5-dimethylphenyl)-1,3-thiazol-5-yl]-2-pyridyl]benzylamine

Aluminum lithium hydride (0.16 g, 4.1 mmol) was added to a suspension of aluminum chloride (0.55 g, 4.1 mmol) in anhydrous tetrahydrofuran (30 mL) and the mixture was stirred at room temperature for 15 minutes. A solution of N-[4-[2-amino-4-(3,5-dimethylphenyl)-1,3-thiazol-5-yl]-2-pyridyl]benzamide (0.40 g, 1.0 mmol) in anhydrous tetrahydrofuran (10 mL) was added to the mixture and the resulting mixture was heated to reflux for 2 hours. After the reaction mixture was cooled to room temperature, water was added and extracted with ethyl acetate. The organic layer was washed with a saturated aqueous solution of sodium chloride, dried over magnesium sulfate, filtered and concentrated. The residue was recrystallized from ethyl acetate-hexane to obtain 0.20 g (0.51 mmol, yield 51%) of the title compound.

mp. 99-102° C.

Example 7

N-[4-[2-amino-4-(3,5-dimethylphenyl)-1,3-thiazol-5-yl]-2-pyridyl]benzamide hydrochloride A 10% solution of hydrogen chloride in methanol (10 mL) was added to a suspension of N-[4-[2-amino-4-(3,5-dimethylphenyl)-1,3-thiazol-5-yl]-2-pyridyl]benzamide (0.45 g, 1.1 mmol) in methanol (30 mL) and the mixture was stirred at room temperature for 30 minutes. The solvent was distilled off and the residue was recrystallized from methanol to obtain 0.36 g (0.83 mmol, yield 73%) of the title compound.

mp. 202-207° C.

Example 8

N-[4-[2-amino-4-(3,5-dimethylphenyl)-1,3-thiazol-5-yl]-2-pyridyl]benzylamine dihydrochloride A 10% solution of hydrogen chloride in methanol (10 mL) was added to a suspension of N-[4-[2-amino-4-(3,5-dimethylphenyl)-1,3-thiazol-5-yl]-2-pyridyl]benzylamine (0.80 g, 2.1 mmol) in methanol (50 mL) and the mixture was stirred at room temperature for 5 hours. The solvent was distilled off and the residue was recrystallized from methanol-ethyl acetate to obtain 0.73 g (1.6 mmol, yield 76%) to obtain the title compound.

mp. 161-163° C.

The structures of the compounds obtained in Examples 1 to 6 are shown below:

Example 1

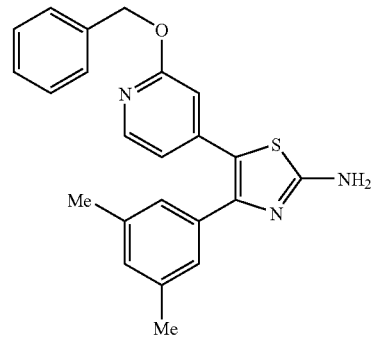

Example 2

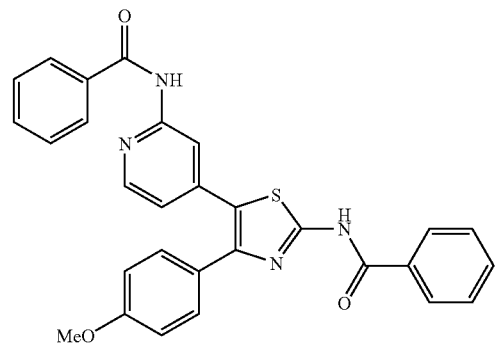

Example 3

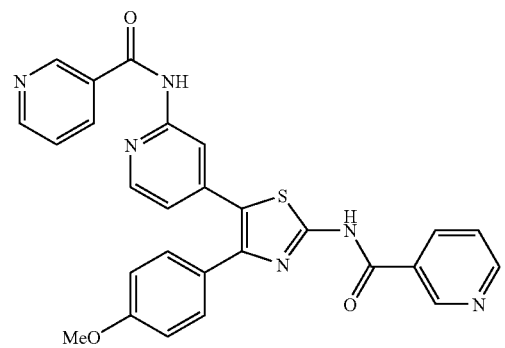

Example 4

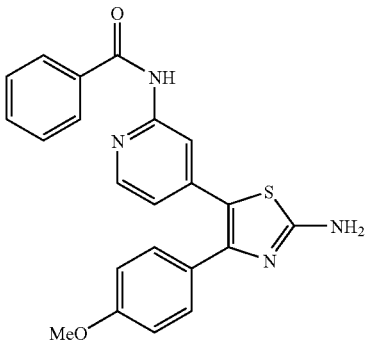

Example 5

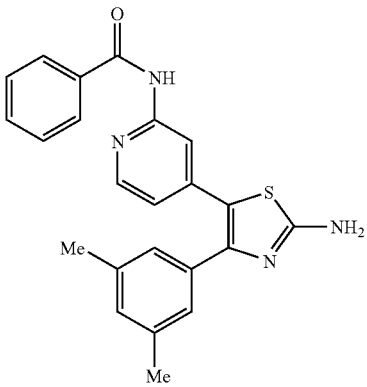

Example 6

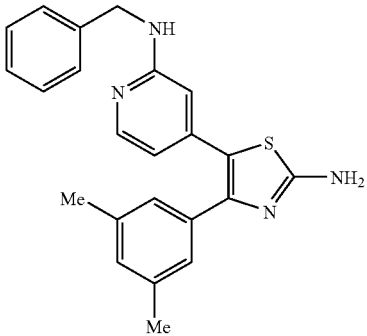

Example 9

N-[5-[2-benzoylamino-4-pyridyl)-4-(3,5-dimethylphenyl)-1,3-thiazol-2-yl]acetamide Acetyl chloride (0.26 mL, 3.7 mmol) and 4-dimethylaminopyridine (0.09 g, 0.76 mmol) were added to a solution of N-[4-[2-amino-4-(3,5-dimethylphenyl)-1,3-thiazol-5-yl]-2-pyridyl]benzamide (0.96 g, 2.4 mmol) in N,N-dimethylacetamide (20 mL) and the mixture was stirred at 70° C. for 16 hours. After the reaction mixture was cooled to room temperature, a saturated aqueous solution of sodium hydrogencarbonate (50 mL) was added. The resulting crude crystals were collected by filtration and washed with water. The crude crystals were recrystallized from ethyl acetate to obtain 0.32 g (yield 30%) of the title compound.
mp. 238-241° C.

Example 10

According to Example 9 and using N-[4-[2-amino-4-(3,5-dimethylphenyl)-1,3-thiazol-5-yl]-2-pyridyl]-N-benzylamine instead of N-[4-[2-amino-4-(3,5-dimethylphenyl)-1,3-thiazol-5-yl]-2-pyridyl]benzamide, the following Example Compound 10 was synthesized.

Example Compound 10

N-[5-(2-benzylamino-4-pyridyl)-4-(3,5-dimethylphenyl)-1,3-thiazol-2-yl]acetamide mp. 217-219° C.

Example 11

According to Example 4 and using N-methylthiourea instead of thiourea, the following Example Compound 11 was synthesized.

Example Compound 11

N-[4-[4-(4-methoxyphenyl)-2-methylamino-1,3-thiazol-5-yl]-2-pyridyl]benzamide mp. 237-241° C.

Example 12

According to Example 4 and using N-[4-[2-(3-methylphenyl)-2-oxoethyl]-2-pyridyl]benzamide instead of 2-(2-benzoylamino-4-pyridyl)-1-(4-methoxyphenyl)ethanone, the following Example compound 12 was synthesized.

Example Compound 12

N-[4-[2-amino-4-(3-methylphenyl)-1,3-thiazol-5-yl]-2-pyridyl]benzamide mp. 216-217° C.

Example 13

N-[4-[4-(4-methoxyphenyl)-2-methyl-1,3-thiazol-5-yl]-2-pyridyl]benzamide

Bromine (0.18 mL, 3.5 mmol) was added to a solution of 2-(2-benzoylamino-4-pyridyl)-1-(4-methoxyphenyl)ethanone (1.2 g, 3.4 mmol) in acetic acid (10 mL) and the mixture was stirred at room temperature for 30 minutes. The reaction mixture was concentrated. The residue was dissolved in N,N-dimethylformamide (20 mL), thioacetamide (0.30 g, 19 mmol) was added to the solution and the mixture was stirred at room temperature for 20 hours. An aqueous saturated solution of sodium hydrogencarbonate (20 mL) was added to the reaction mixture, the resulting mixture was extracted with ethyl acetate and the extract was washed with water. The extract was dried and concentrated. The residue was purified by silica gel column chromatography (hexane:ethyl acetate, 1:1) to obtain 0.68 g (yield 50%) of the title compound.

mp. 134-135° C.

Example 14

N-[4-[2-[(4-fluorophenyl)-4-(3-methylphenyl)-1,3-thiazol-5-yl]-2-pyridyl]phenylacetamide Phenylacetyl chloride (0.33 mL, 2.5 mmol) and triethylamine (0.31 mL, 2.2 mmol) were added to a solution of 4-[2-(4-fluorophenyl)-4-(3-methylphenyl)-1,3-thiazol-5-yl]-2-pyridylamine (0.81 g, 2.2 mmol) in tetrahydrofuran (20 mL) and the mixture was stirred at room temperature for 13 hours. An aqueous saturated solution of sodium hydrogencarbonate (20 mL) was added to the reaction mixture, the resulting mixture was extracted with ethyl acetate and the extract was washed with water. This extract was dried and concentrated. The residue was purified by silica gel column chromatography (hexane:ethyl acetate, 2:1) to obtain 0.86 g (yield 80%) of the title compound.

mp. 187-190° C.

Example 15

According to Example 14 and using 4-[4-(4-methoxyphenyl)-2-methyl-1,3-thiazol-5-yl]-2-pyridylamine, 4-[2-ethyl-4-(3-methylphenyl)-1,3-thiazol-5-yl]-2-pyridylamine, 4-[4-(3-methylphenyl)-2-propyl-1,3-thiazol-5-yl]-2-pyridylamine, 4-[2-butyl-4-(3-methylphenyl)-1,3-thiazol-5-yl]-2-pyridylamine, 4-[2-(2-chlorophenyl)-4-(3-methylphenyl)-1,3-thiazol-5-yl]-2-pyridylamine and 4-[4-(3-methylphenyl)-2-(4-methylthiophenyl)-1,3-thiazol-5-yl]-2-pyridylamine, respectively, instead of 4-[2-(4-fluorophenyl)-4-(3-methylphenyl)-1,3-thiazol-5-yl]-2-pyridylamine, the following Example Compounds 15-1-15-6 were synthesized.

Example Compound 15-1

N-[4-[4-(4-methoxyphenyl)-2-methyl-1,3-thiazol-5-yl]-2-pyridyl]phenylacetamide mp. 118-120° C.

Example Compound 15-2

N-[4-[2-ethyl-4-(3-methylphenyl)-1,3-thiazol-5-yl]-2-pyridyl]phenylacetamide mp. 107-108° C.

Example Compound 15-3

N-[4-[4-(3-methylphenyl)-2-propyl-1,3-thiazol-5-yl]-2-pyridyl]phenylacetamide mp. 109-111° C.

Example Compound 15-4

N-[4-[2-butyl-4-(3-methylphenyl)-1,3-thiazol-5-yl]-2-pyridyl]phenylacetamide mp. 92-93° C.

Example Compound 15-5

N-(4-[2-(2-chlorophenyl)-4-(3-methylphenyl)-1,3-thiazol-5-yl]-2-pyridyl]phenylacetamide mp. 141-142° C.

Example Compound 15-6

N-[4-[4-(3-methylphenyl)-2-(4-methylthiophenyl)-1,3-thiazol-5-yl]-2-pyridyl]phenylacetamide mp. 205-206° C.

Example 16

According to Examples 14 and 15 and using benzoyl chloride, 3-phenylpropionyl chloride, 3-(4-methoxyphenyl)propionyl chloride, 3-(4-fluorophenyl)propionyl chloride, 4-phenylbutyryl chloride, 5-phenylvaleryl chloride, 2-thiophenecarbonyl chloride and 2-naphthoyl chloride, respectively, instead of phenylacetyl chloride, the following Example Compounds 16-1-16-18 were synthesized.

Example Compound 16-1

N-[4-[2-ethyl-4-(3-methylphenyl)-1,3-thiazol-5-yl]-2-pyridyl]benzamide mp. 113-114° C.

Example Compound 16-2

N-[4-[2-ethyl-4-(3-methylphenyl)-1,3-thiazol-5-yl]-2-pyridyl]-3-phenylpropionamide mp. 126-127° C.

Example Compound 16-3

N-[4-[2-ethyl-4-(3-methylphenyl)-1,3-thiazol-5-yl]-2-pyridyl]-3-(4-methoxyphenyl)propionamide mp. 137-138° C.

Example Compound 16-4

N-[4-[2-ethyl-4-(3-methylphenyl)-1,3-thiazol-5-yl]-2-pyridyl]-3-(4-fluorophenyl)propionamide mp. 116-117° C.

Example Compound 16-5

N-[4-[2-ethyl-4-(3-methylphenyl)-1,3-thiazol-5-yl]-2-pyridyl]-4-phenylbutyramide mp. 92-93° C.

Example Compound 16-6

N-[4-[2-ethyl-4-(3-methylphenyl)-1,3-thiazol-5-yl]-2-pyridyl]-5-phenylvaleramide mp. 86-87° C.

Example Compound 16-7

N-[4-[4-(3-methylphenyl)-2-propyl-1,3-thiazol-5-yl]-2-pyridyl]benzamide

Amorphous Powder
$^1$H-NMR (CDCl$_3$) δ: 1.08 (3H, t, J=7.1 Hz), 1.80-1.99 (2H, m), 2.34 (3H, s), 3.04 (2H, t, J=7.7 Hz), 6.88 (1H, dd, J=5.2, 1.7 Hz), 7.15-7.63 (7H, m), 7.90-7.95 (2H, m), 8.11 (1H, d, J=5.2 Hz), 8.51 (1H, s), 8.61 (1H, br s)

Example Compound 16-8

N-[4-[4-(3-methylphenyl)-2-propyl-1,3-thiazol-5-yl]-2-pyridyl]-3-phenylpropionamide mp. 103-104° C.

Example Compound 16-9

N-[4-[2-butyl-4-(3-methylphenyl)-1,3-thiazol-5-yl]-2-pyridyl]benzamide

Amorphous Powder
$^1$H-NMR (CDCl$_3$) δ: 0.99 (3H, t, J=7.2 Hz), 1.40-1.60 (2H, m), 1.76-1.93 (2H, m), 2.34 (3H, s), 3.06 (2H, t, J=7.7 Hz), 6.88 (1H, dd, J=5.0, 1.7 Hz), 7.10-7.26 (3H, m), 7.41 (1H, s), 7.46-7.61 (3H, m), 7.94 (2H, dd, J=8.1, 1.5 Hz), 8.10 (1H, d, J=5.0 Hz), 8.52 (1H, s), 8.71 (1H, br s)

Example Compound 16-10

N-[4-[2-butyl-4-(3-methylphenyl)-1,3-thiazol-5-yl]-2-pyridyl]-3-phenylpropionamide mp. 77-78° C.

Example Compound 16-11

N-[4-[2-(4-fluorophenyl)-4-(3-methylphenyl)-1,3-thiazol-5-yl]-2-pyridyl]benzamide mp. 126-128° C.

Example Compound 16-12

N-[4-[2-(4-fluorophenyl)-4-(3-methylphenyl)-1,3-thiazol-5-yl]-2-pyridyl]-3-phenylpropionamide mp. 169-171° C.

Example Compound 16-13

N-(4-[2-(2-chlorophenyl)-4-(3-methylphenyl)-1,3-thiazol-5-yl]-2-pyridyl]benzamide mp. 138-140° C.

Example Compound 16-14

N-[4-[2-(2-chlorophenyl)-4-(3-methylphenyl)-1,3-thiazol-5-yl]-2-pyridyl]-3-phenylpropionamide mp. 156-158° C.

Example Compound 16-15

N-[4-[4-(3-methylphenyl)-2-(4-methylthiophenyl)-1,3-thiazol-5-yl]-2-pyridyl]benzamide mp. 180-182° C.

Example Compound 16-16

N-[4-[4-(3-methylphenyl)-2-(4-methylthiophenyl)-1,3-thiazol-5-yl]-2-pyridyl]-3-phenylpropionamide mp. 174-175° C.

Example Compound 16-17

N-[4-[4-(3-methylphenyl)-2-(4-methylthiophenyl)-1,3-thiazol-5-yl]-2-pyridyl]-2-thiophenecarboxamide mp. 145-147° C.

Example Compound 16-18

N-[4-[4-(3-methylphenyl)-2-(4-methylthiophenyl)-1,3-thiazol-5-yl]-2-pyridyl]-2-naphthamide mp. 184-186° C.

Example 17

N-[4-[2-ethyl-4-(3-methylphenyl)-1,3-thiazol-5-yl]-2-pyridyl]-N-methylphenylacetamide Sodium hydride (60% paraffin dispersion, 58 mg, 1.5 mmol) was added to a solution of N-[4-[2-ethyl-4-(3-methylphenyl)-1,3-thiazol-5-yl]-2-pyridyl]phenylacetamide (0.50 g, 1.2 mmol) in dimethyl sulfoxide (5 mL) and the mixture was stirred at room temperature for 1 hour. Methyl iodide (0.09 mL, 1.5 mmol) was added to this reaction solution and the mixture was stirred at room temperature for 1 hour. A 10% aqueous solution of ammonium chloride was added to the reaction mixture and the mixture was extracted with ethyl acetate. The extract was washed with a saturated aqueous solution of sodium chloride, dried and concentrated. The residue was purified by silica gel column chromatography (hexane:ethyl acetate, 7:1→4:1) and washed with hexane to obtain 0.18 g (yield 35%) of the title compound.

mp. 75-76° C.

Example 18

According to Example 17 and using N-[4-[2-ethyl-4-(3-methylphenyl)-1,3-thiazol-5-yl]-2-pyridyl]-3-phenylpropionamide instead of N-[4-[2-ethyl-4-(3-methylphenyl)-1,3-thiazol-5-yl]-2-pyridyl]phenylacetamide, the following Example Compound 18 was synthesized.

Example Compound 18

N-[4-[2-ethyl-4-(3-methylphenyl)-1,3-thiazol-5-yl]-2-pyridyl]-N-methyl-3-phenylpropionamide Oily Product
$^1$H-NMR (CDCl$_3$) δ: 1.46 (3H, t, J=7.5 Hz), 2.32 (3H, s), 2.51 (2H, t, J=7.9 Hz), 2.93 (2H, t, J=7.9 Hz), 3.10 (2H, q, J=7.5 Hz), 3.22 (3H, s), 6.98 (1H, s), 7.03-7.29 (9H, m), 7.37(1H, s), 8.37 (1H, d, J=3.6 Hz)

Example 19

According to Example 6 and using N-[4-[4-(4-methoxyphenyl)-2-methyl-1,3-thiazol-5-yl]-2-pyridyl]benzamide, N-[4-[2-ethyl-4-(3-methylphenyl)-1,3-thiazol-5-yl]-2-pyridyl]benzamide, N-[4-[2-ethyl-4-(3-methylphenyl)-1,3-thiazol-5-yl]-2-pyridyl]phenylacetamide, N-[4-[2-ethyl-4-(3-methylphenyl)-1,3-thiazol-5-yl]-2-pyridyl]-3-phenylpropionamide, N-[4-[4-(3-methylphenyl)-2-propyl-1,3-thiazol-5-yl]-2-pyridyl]benzamide, N-[4-[4-(3-methylphenyl)-2-propyl-1,3-thiazol-5-yl]-2-pyridyl]phenylacetamide, N-[4-[4-(3-methylphenyl)-2-propyl-1,3-thiazol-5-yl]-2-pyridyl]-3-phenylpropionamide, N-[4-[2-butyl-4-(3-methylphenyl)-1,3-thiazol-5-yl]-2-pyridyl]benzamide, N-[4-[2-butyl-4-(3-methylphenyl)-1,3-thiazol-5-yl]-2-pyridyl]phenylacetamide, N-[4-[2-butyl-4-(3-methylphenyl)-1,3-thiazol-5-yl]-2-pyridyl]-3-phenylpropionamide, N-[4-[2-(4-fluorophenyl)-4-(3-methylphenyl)-1,3-thiazol-5-yl]-2-pyridyl]benzamide, N-[4-[2-(4-fluorophenyl)-4-(3-methylphenyl)-1,3-thiazol-5-yl]-2-pyridyl]phenylacetamide, N-[4-[2-(4-fluorophenyl)-4-(3-methylphenyl)-1,3-thiazol-5-yl]-2-pyridyl]-3-phenylpropionamide, N-[4-[2-(2-chlorophenyl)-4-(3-methylphenyl)-1,3-thiazol-5-yl]-2-pyridyl]benzamide, N-[4-[2-(2-chlorophenyl)-4-(3-methylphenyl)-1,3-thiazol-5-yl]-2-pyridyl]phenylacetamide, N-[4-[2-(2-chlorophenyl)-4-(3-methylphenyl)-1,3-thiazol-5-yl]-2-pyridyl]-3-phenylpropionamide, N-[4-[4-(3-methylphenyl)-2-(4-methylthiophenyl)-1,3-thiazol-5-yl]-2-pyridyl]benzamide, N-[4-[4-(3-methylphenyl)-2-(4-methylthiophenyl)-1,3-thiazol-5-yl]-2-pyridyl]phenylacetamide, N-[4-[4-(3-methylphenyl)-2-(4-methylthiophenyl)-1,3-thiazol-5-yl]-2-pyridyl]-3-phenylpropionamide and N-[4-[4-(3-methylphenyl)-2-(4-methylthiophenyl)-1,3-thiazol-5-yl]-2-pyridyl]-2-naphthamide, respectively, instead of N-[4-[2-amino-4-(3,5-dimethylphenyl)-1,3-thiazol-5-yl]-2-pyridyl]benzamide, the following Example Compounds 19-1-19-20 were synthesized.

Example Compound 19-1

N-benzyl-N-[4-[4-(4-methoxyphenyl)-2-methyl-1,3-thiazol-5-yl]-2-pyridyl]amine mp. 132-133° C.

Example Compound 19-2

N-benzyl-N-[4-[2-ethyl-4-(3-methylphenyl)-1,3-thiazol-5-yl]-2-pyridyl]amine mp. 106-107° C.

Example Compound 19-3

N-[4-[2-ethyl-4-(3-methylphenyl)-1,3-thiazol-5-yl]-2-pyridyl]-N-(2-phenylethyl) amine mp. 97-98° C.

Example Compound 19-4

N-[4-[2-ethyl-4-(3-methylphenyl)-1,3-thiazol-5-yl]-2-pyridyl]-N-(3-phenylpropyl)amine mp. 52-53° C.

Example Compound 19-5

N-benzyl-N-[4-[4-(3-methylphenyl)-2-propyl-1,3-thiazol-5-yl]-2-pyridyl]amine

Oily Product
$^1$H-NMR (CDCl$_3$) δ: 1.06(3H, t, J=7.4 Hz), 1.77-1.96 (2H, m), 2.33 (3H, s), 3.00 (2H, t, J=7.7 Hz), 4.38 (2H, d, J=5.4 Hz), 4.83 (1H, br t), 6.32 (1H, s), 6.53 (1H, dd, J=5.4, 1.6 Hz), 7.10-7.40 (9H, m), 8.01 (1H, d, J=5.4 Hz)

Example Compound 19-6

N-[4-[4-(3-methylphenyl)-2-propyl-1,3-thiazol-5-yl]-2-pyridyl]-N-(2-phenylethyl)amine Oily Product
$^1$H-NMR (CDCl$_3$) δ: 1.08 (3H, t, J=7.5 Hz), 1.78-1.93 (2H, m), 2.32 (3H, s), 2.81 (2H, t, J=7.0 Hz), 3.01 (2H, t, J=7.7 Hz), 3.42 (2H, dt, J=6.2, 7.0 Hz), 4.52 (1H, br t), 6.30 (1H, s), 6.51 (1H, dd, J=5.2, 1.5 Hz), 7.11-7.34 (8H, m), 7.43 (1H, s), 8.00 (1H, d, J=5.2 Hz)

Example Compound 19-7

N-[4-[4-(3-methylphenyl)-2-propyl-1,3-thiazol-5-yl]-2-pyridyl]-N-(3-phenylpropyl)amine Oily Product
$^1$H-NMR (CDCl$_3$) δ: 1.08 (3H, t, J=7.4 Hz), 1.78-1.93 (4H, m), 2.32 (3H, s), 2.66 (2H, t, J=7.2 Hz), 3.01 (2H, t, J=7.7 Hz), 3.16 (2H, dt, J=6.2, 7.2 Hz), 4.52 (1H, br s), 6.26 (1H, s), 6.49 (1H, dd, J=5.2, 1.5 Hz), 7.07-7.32 (8H, m), 7.42 (1H, s), 7.98 (1H, d, J=5.2 Hz)

Example Compound 19-8

N-benzyl-N-[4-[2-butyl-4-(3-methylphenyl)-1,3-thiazol-5-yl]-2-pyridyl]amine

Oily Product
$^1$H-NMR (CDCl$_3$) δ: 0.97 (3H, t, J=7.3 Hz), 1.38-1.59 (2H, m), 1.73-1.90 (2H, m), 2.33 (3H, s), 3.02 (2H, t, J=7.7 Hz), 4.37 (2H, d, J=5.7 Hz), 4.83 (1H, t, J=7.3 Hz), 6.31 (1H, s), 6.52 (1H, d, J=5.5 Hz), 7.09-7.43 (9H, m), 8.00 (1H, d, J=5.5 Hz)

Example Compound 19-9

N-[4-[2-butyl-4-(3-methylphenyl)-1,3-thiazol-5-yl]-2-pyridyl]-N-(2-phenylethyl)amine Oily Product
$^1$H-NMR (CDCl$_3$) δ: 0.98 (3H, t, J=7.3 Hz), 1.39-1.59 (2H, m), 1.74-1.92 (2H, m), 2.32 (3H, s), 2.81 (2H, t, J=7.0 Hz), 3.04 (2H, t, J=7.7 Hz), 3.41 (2H, dt, J=6.1, 7.0 Hz), 4.55 (1H, t, J=6.1 Hz), 6.30 (1H, s), 6.51 (1H, d, J=5.1 Hz), 7.06-7.19 (3H, m), 7.20-7.38 (5H, m), 7.43 (1H, s), 7.99 (1H, d, J=5.1 Hz)

Example Compound 19-10

N-[4-[2-butyl-4-(3-methylphenyl)-1,3-thiazol-5-yl]-2-pyridyl]-N-(3-phenylpropyl)amine Oily Product
$^1$H-NMR (CDCl$_3$) δ: 0.98 (3H, t, J=7.1 Hz), 1.39-1.57 (2H, m), 1.75-1.98 (4H, m), 2.32 (3H, s), 2.67 (2H, t, J=7.8 Hz), 3.04 (2H, t, J=7.7 Hz), 3.16 (2H, dt, J=5.9, 6.2 Hz), 4.52 (1H, t, J=5.9 Hz), 6.26 (1H, s), 6.49 (1H, d, J=5.1 Hz), 7.06-7.38 (8H, m), 7.42 (1H, s), 7.97 (1H, d, J=5.1 Hz)

Example Compound 19-11

N-benzyl-N-[4-[2-(4-fluorophenyl)-4-(3-methylphenyl)-1,3-thiazol-5-yl]-2-pyridyl]amine mp. 143-146° C.

Example Compound 19-12

N-[4-[2-(4-fluorophenyl)-4-(3-methylphenyl)-1,3-thiazol-5-yl]-2-pyridyl]-N-(2-phenylethyl)amine mp. 97-98° C.

Example Compound 19-13

N-[4-[2-(4-fluorophenyl)-4-(3-methylphenyl)-1,3-thiazol-5-yl]-2-pyridyl]-N-(3-phenylpropyl)amine mp. 110-112° C.

Example Compound 19-14

N-benzyl-N-[4-[2-(2-chlorophenyl)-4-(3-methylphenyl)-1,3-thiazol-5-yl]-2-pyridyl]amine mp. 84-86° C.

Example Compound 19-15

N-[4-[2-(2-chlorophenyl)-4-(3-methylphenyl)-1,3-thiazol-5-yl]-2-pyridyl]-N-(2-phenylethyl)amine mp. 113-114° C.

Example Compound 19-16

N-[4-[2-(2-chlorophenyl)-4-(3-methylphenyl)-1,3-thiazol-5-yl]-2-pyridyl]-N-(3-phenylpropyl)amine mp. 101-102° C.

Example Compound 19-17

N-benzyl-N-[4-[4-(3-methylphenyl)-2-(4-methylthiophenyl)-1,3-thiazol-5-yl]-2-pyridyl]amine mp. 134-136° C.

Example Compound 19-18

N-[4-[4-(3-methylphenyl)-2-(4-methylthiophenyl)-1,3-thiazol-5-yl]-2-pyridyl]-N-(2-phenylethyl)amine mp. 137-139° C.

Example Compound 19-19

N-[4-[4-(3-methylphenyl)-2-(4-methylthiophenyl)-1,3-thiazol-5-yl]-2-pyridyl]-N-(3-phenylpropyl)amine mp. 106-107° C.

Example Compound 19-20

N-[4-[4-(3-methylphenyl)-2-(4-methylthiophenyl)-1,3-thiazol-5-yl]-2-pyridyl]-N-(2-naphthylmethyl)amine mp. 144-145° C.

Example 20

N-[4-[4-(3-methylphenyl)-2-(4-methylsulfonylphenyl)-1,3-thiazol-5-yl]-2-pyridyl]benzamide To a solution of N-[4-[4-(3-methylphenyl)-2-(4-methylthiophenyl)-1,3-thiazol-5-yl]-2-pyridyl]benzamide (0.50 g, 1.0 mmol) in N,N-dimethylformamide (5 mL) was added m-chloroperbenzoic acid (0.55 g, 2.2 mmol) and the mixture was stirred at room temperature for 1 hour. An 8N aqueous solution of sodium hydroxide was added to the reaction mixture and the resulting solid was collected by filtration. This solid was recrystallized from ethanol to obtain 0.29 g (yield 54%) of the title compound.
mp. 212-214° C.

Example 21

According to Example 20 and using N-[4-[4-(3-methylphenyl)-2-(4-methylthiophenyl)-1,3-thiazol-5-yl]-2-pyridyl]phenylacetamide, N-[4-[4-(3-methylphenyl)-2-(4-methylthiophenyl)-1,3-thiazol-5-yl]-2-pyridyl]-3-phenylpropionamide, N-[4-[4-(3-methylphenyl)-2-(4-methylthiophenyl)-1,3-thiazol-5-yl]-2-pyridyl]-2-thiophenecarboxamide, N-[4-[4-(3-methylphenyl)-2-(4-methylthiophenyl)-1,3-thiazol-5-yl]-2-pyridyl]-2-naphthamide, N-benzyl-N-[4-[4-(3-methylphenyl)-2-(4-methylthiophenyl)-1,3-thiazol-5-yl]-2-pyridyl]amine, N-[4-[4-(3-methylphenyl)-2-(4-methylthiophenyl)-1,3-thiazol-5-yl]-2-pyridyl]-N-(3-phenylpropyl)amine and N-[4-[4-(3-methylphenyl)-2-(4-methylthiophenyl)-1,3-thiazol-5-yl]-2-pyridyl]-N-(2-naphthylmethyl)amine, respectively, instead of N-[4-[4-(3-methylphenyl)-2-(4-methylthiophenyl)-1,3-thiazol-5-yl]-2-pyridyl]benzamide, the following Example Compounds 21-1-21-7 were synthesized.

Example Compound 21-1

N-[4-[4-(3-methylphenyl)-2-(4-methylsulfonylphenyl)-1,3-thiazol-5-yl]-2-pyridyl]phenylacetamide mp. 244-245° C.

Example Compound 21-2

N-[4-[4-(3-methylphenyl)-2-(4-methylsulfonylphenyl)-1,3-thiazol-5-yl]-2-pyridyl]-3-phenylpropionamide mp. 236-237° C.

Example Compound 21-3

N-[4-[4-(3-methylphenyl)-2-(4-methylsulfonylphenyl)-1,3-thiazol-5-yl]-2-pyridyl]-2-thiophenecarboxamide mp. 199-201° C.

Example Compound 21-4

N-[4-[4-(3-methylphenyl)-2-(4-methylsulfonylphenyl)-1,3-thiazol-5-yl]-2-pyridyl]-2-naphthamide mp. 231-233° C.

Example Compound 21-5

N-benzyl-N-[4-[4-(3-methylphenyl)-2-(4-methylsulfonylphenyl)-1,3-thiazol-5-yl]-2-pyridyl]amine mp. 148-150° C.

Example Compound 21-6

N-[4-[4-(3-methylphenyl)-2-(4-methylsulfonylphenyl)-1,3-thiazol-5-yl]-2-pyridyl]-N-(3-phenylpropyl)amine mp. 167-168° C.

Example Compound 21-7

N-[4-[4-(3-methylphenyl)-2-(4-methylsulfonylphenyl)-1,3-thiazol-5-yl]-2-pyridyl]-N-(2-naphthylmethyl)amine mp. 167-168° C.

Example 22

N-[4-[2-amino-4-(3-methylphenyl)-1,3-thiazol-5-yl]-2-pyridyl]-N-benzylamine

A mixture of [5-(2-fluoro-4-pyridyl)-4-(3-methylphenyl)-1,3-thiazol-2-yl]amine (0.29 g, 1.0 mmol) and benzylamine (1.2 mL, 11 mmol) was stirred at 150° C. for 3 hours. After the reaction mixture was cooled to room temperature, a saturated aqueous solution of sodium hydrogencarbonate (20 mL) was added, the resulting mixture was extracted with ethyl acetate and extract was washed with water. This extract was dried and concentrated. The residue was purified by silica gel column chromatography (hexane:ethyl acetate, 1:1) to obtain 0.16 g (yield 41%) of the title compound.
mp. 178-179° C.

Example 23

According to Example 22 and using 4-methoxybenzylamine, 3-methoxybenzylamine, 2-methoxybenzylamine, 4-chlorobenzylamine, 3-chlorobenzylamine, (R)-1-phenylethylamine, (S)-1-phenylethylamine and N-benzyl-N-methylamine instead of benzylamine, the following Example Compounds 23-1-23-8 were synthesized.

Example Compound 23-1

N-[4-[2-amino-4-(3-methylphenyl)-1,3-thiazol-5-yl]-2-pyridyl]-N-(4-methoxybenzyl)amine mp. 183-184° C.

Example Compound 23-2

N-[4-[2-amino-4-(3-methylphenyl)-1,3-thiazol-5-yl]-2-pyridyl]-N-(3-methoxybenzyl)amine mp. 152-154° C.

Example Compound 23-3

N-[4-[2-amino-4-(3-methylphenyl)-1,3-thiazol-5-yl]-2-pyridyl]-N-(2-methoxybenzyl)amine mp. 158-159° C.

Example Compound 23-4

N-[4-[2-amino-4-(3-methylphenyl)-1,3-thiazol-5-yl]-2-pyridyl]-N-(4-chlorobenzyl)amine mp. 182-183° C.

Example Compound 23-5

N-[4-[2-amino-4-(3-methylphenyl)-1,3-thiazol-5-yl]-2-pyridyl]-N-(3-chlorobenzyl)amine mp. 180-181° C.

Example Compound 23-6

(R)-N-[4-[2-amino-4-(3-methylphenyl)-1,3-thiazol-5-yl]-2-pyridyl]-N-(1-phenylethyl)amine mp. 94-98° C.

Example Compound 23-7

(S)-N-[4-[2-amino-4-(3-methylphenyl)-1,3-thiazol-5-yl]-2-pyridyl]-N-(1-phenylethyl)amine mp. 93-96° C.

Example Compound 23-8

N-[4-[2-amino-4-(3-methylphenyl)-1,3-thiazol-5-yl]-2-pyridyl]-N-benzyl-N-methylamine mp. 138-140° C.

Example 24

According to Example 22 and using [5-(2-fluoro-4-pyridyl)-4-(3-methoxyphenyl)-1,3-thiazol-2-yl]amine instead of [5-(2-fluoro-4-pyridyl)-4-(3-methylphenyl)-1,3-thiazol-2-yl]amine, the following Example Compound 24 was synthesized.

Example Compound 24

N-[4-[2-amino-4-(3-methoxyphenyl)-1,3-thiazol-5-yl]-2-pyridyl]-N-benzylamine mp. 217-218° C.

Example 25

According to Example 22 and using 5-(2-fluoro-4-pyridyl)-4-(3-methylphenyl)-2-(4-methylsulfonylphenyl)-1,3-thiazole instead of [5-(2-fluoro-4-pyridyl)-4-(3-methylphenyl)-1,3-thiazol-2-yl]amine, and using 2-phenylethylamine, 4-fluorobenzylamine, N-benzyl-N-methylamine, N-methyl-2-phenylethylamine and 2-thienylmethylamine, respectively, instead of benzylamine, the following Example Compounds 25-1-25-5 were synthesized.

Example Compound 25-1

N-[4-[4-(3-methylphenyl)-2-(4-methylsulfonylphenyl)-1,3-thiazol-5-yl]-2-pyridyl]-N-(2-phenylethyl)amine mp. 174-176° C.

Example Compound 25-2

N-(4-fluorobenzyl)-N-[4-[4-(3-methylphenyl)-2-(4-methylsulfonylphenyl)-1,3-thiazol-5-yl]-2-pyridyl]amine mp. 155-158° C.

Example Compound 25-3

N-benzyl-N-methyl-N-[4-[4-(3-methylphenyl)-2-(4-methylsulfonylphenyl)-1,3-thiazol-5-yl]-2-pyridyl]amine mp. 165-166° C.

Example Compound 25-4

N-methyl-N-[4-[4-(3-methylphenyl)-2-(4-methylsulfonylphenyl)-1,3-thiazol-5-yl]-2-pyridyl]-N-(2-phenylethyl)amine mp. 116-117° C.

Example Compound 25-5

N-[4-[4-(3-methylphenyl)-2-(4-methylsulfonylphenyl)-1,3-thiazol-5-yl]-2-pyridyl]-N-(2-thienylmethyl)amine mp. 107-109° C.

Example 26

4-(3-methylphenyl)-2-(4-methylsulfonylphenyl)-5-(2-phenylthio-4-pyridyl)-1,3-thiazole A mixture of 5-(2-fluoro-4-pyridyl)-4-(3-methylphenyl)-2-(4-methylsulfonylphenyl)-1,3-thiazole (0.40 g, 0.94 mmol) and thiophenol (1.0 mL, 9.7 mmol) was stirred at 150° C. for 10 hours. After the reaction mixture was cooled to room temperature, a saturated aqueous solution of sodium hydrogencarbonate was added, the resulting mixture was extracted with ethyl acetate and washed with water. This extract was dried and concentrated. The residue was purified by silica gel column chromatography (hexane:ethyl acetate, 1:1) and recrystallized from ethanol to obtain 0.34 g (yield 70%) of the title compound.

mp. 116-118° C.

Example 27

5-(2-benzylthio-4-pyridyl)-4-(3-methylphenyl)-2-(4-methylsulfonylphenyl)-1,3-thiazole After sodium hydride (60% paraffin dispersion, 0.13 g, 3.2 mmol) was washed with hexane twice, it was suspended in N,N-dimethylformamide (15 mL). Phenylmethanethiol (0.35 mL, 3.0 mmol) was added to this suspension and stirred for 10 minutes. A solution of 5-(2-fluoro-4-pyridyl)-4-(3-methylphenyl)-2-(4-methylsulfonylphenyl)-1,3-thiazole (0.49 g, 1.2 mmol) in N,N-dimethylformamide (5 mL) was added to this mixture and stirred for 1 hour. An 8N aqueous solution of sodium hydroxide was added to the reaction mixture, the resulting mixture was extracted with ethyl acetate, and the extract was washed with water. This extract was dried and concentrated. The residue was purified by silica gel column chromatography (hexane:ethyl acetate, 2:1) to obtain 0.48 g (yield 79%).

mp. 182-185° C.

Example 28

4-(3-methylphenyl)-2-(4-methylsulfonylphenyl)-5-(2-phenylsulfonyl-4-pyridyl)-1,3-thiazole To a solution of 4-(3-methylphenyl)-2-(4-methylsulfonylphenyl)-5-(2-phenylthio-4-pyridyl)-1,3-thiazole (0.48 g, 0.93 mmol) in N,N-dimethylformamide (10 mL) was added m-chloroperbenzoic acid (0.51 g, 2.4 mmol) and the mixture was stirred at room temperature for 1 hour. An 8N aqueous solution of sodium hydroxide was added to the reaction mixture and the resulting solid was collected by filtration. The solid was recrystallized from ethanol to obtain 0.42 g (yield 82%) of the title compound.

mp. 126-128° C.

Compounds prepared in the above Examples 9-28 are shown in table 1 to Table 6.

TABLE 1
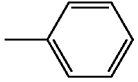
| Example Compound No. | R² | Z | Y | R¹ | R³ | mp/° C. |
|---|---|---|---|---|---|---|
| 9 | 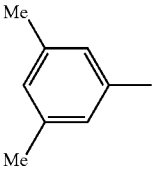 | —CO— | —NH— | —NHCOMe | 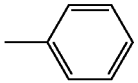 | 238-241 |
| 10 | 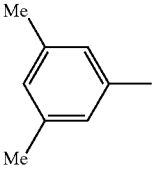 | —CH₂— | —NH— | —NHCOMe | 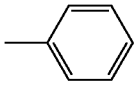 | 217-219 |
| 11 | 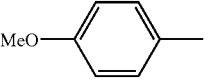 | —CO— | —NH— | —NHMe | 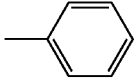 | 237-241 |
| 12 | 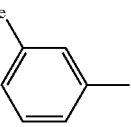 | —CO— | —NH— | —NH₂ | 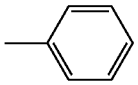 | 216-217 |
| 13 | 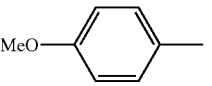 | —CO— | —NH— | —Me | 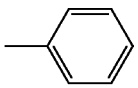 | 134-135 |
| 14 | 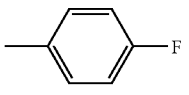 | —CH₂CO— | —NH— | 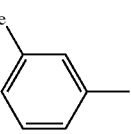 | 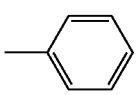 | 187-190 |
| 15-1 | 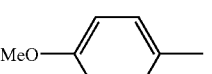 | —CH₂CO— | —NH— | —Me | 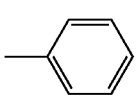 | 118-120 |
| 15-2 | 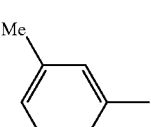 | —CH₂CO— | —NH— | —CH₂Me | 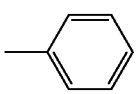 | 107-108 |
| 15-3 | 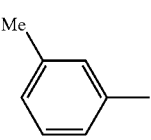 | —CH₂CO— | —NH— | —(CH₂)₂Me | | 109-111 |

TABLE 1-continued
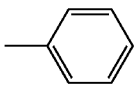
| Example Compound No. | R² | Z | Y | R¹ | R³ | mp/° C. |
|---|---|---|---|---|---|---|
| 15-4 | 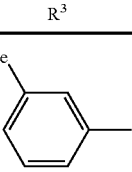 | —CH₂CO— | —NH— | —(CH₂)₃Me | 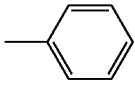 | 92-93 |
| 15-5 | 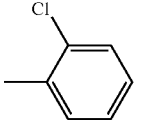 | —CH₂CO— | —NH— | 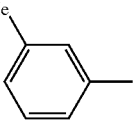 | 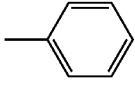 | 141-142 |
| 15-6 | 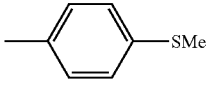 | —CH₂CO— | —NH— | 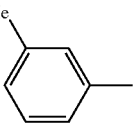 | 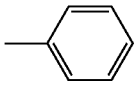 | 205-206 |
| 16-1 | 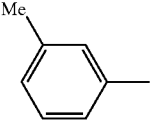 | —CO— | —NH— | —CH₂Me | 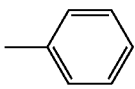 | 113-114 |
| 16-2 | 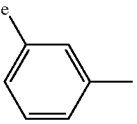 | —(CH₂)₂CO— | —NH— | —CH₂Me | 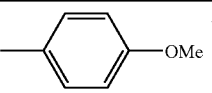 | 126-127 |
TABLE 2
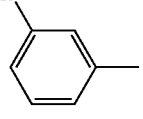
| Example Compound No. | R² | Z | Y | R¹ | R³ | mp/° C. |
|---|---|---|---|---|---|---|
| 16-3 |  | —(CH₂)₂CO— | —NH— | —CH₂Me |  | 137-138 |

TABLE 2-continued

| Example Compound No. | R² | Z | Y | R¹ | R³ | mp/° C. |
|---|---|---|---|---|---|---|
| 16-4 | 4-F-C₆H₄- | —(CH₂)₂CO— | —NH— | —CH₂Me | 3-Me-C₆H₄- | 116-117 |
| 16-5 | C₆H₅- | —(CH₂)₂CO— | —NH— | —CH₂Me | 3-Me-C₆H₄- | 92-93 |
| 16-6 | C₆H₅- | —(CH₂)₂CO— | —NH— | —CH₂Me | 3-Me-C₆H₄- | 86-87 |
| 16-7 | C₆H₅- | —CO— | —NH— | —(CH₂)₂Me | 3-Me-C₆H₄- | amorphous |
| 16-8 | C₆H₅- | —(CH₂)₂CO— | —NH— | —(CH₂)₂Me | 3-Me-C₆H₄- | 103-104 |
| 16-9 | C₆H₅- | —CO— | —NH— | —(CH₂)₂Me | 3-Me-C₆H₄- | amorphous |
| 16-10 | C₆H₅- | —(CH₂)₂CO— | —NH— | —(CH₂)₂Me | 3-Me-C₆H₄- | 77-78 |
| 16-11 | C₆H₅- | —CO— | —NH— | 4-F-C₆H₄- | 3-Me-C₆H₄- | 126-128 |
| 16-12 | C₆H₅- | —(CH₂)₂CO— | —NH— | 4-F-C₆H₄- | 3-Me-C₆H₄- | 169-171 |

TABLE 2-continued
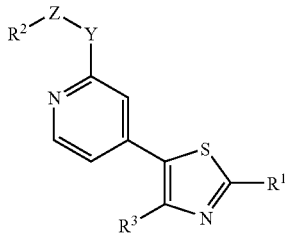
| Example Compound No. | R² | Z | Y | R¹ | R³ | mp/° C. |
|---|---|---|---|---|---|---|
| 16-13 | 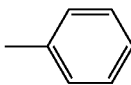 | —CO— | —NH— | 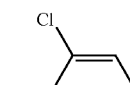 | 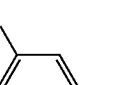 | 138-140 |
| 16-14 | 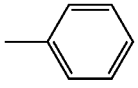 | —(CH₂)₂CO— | —NH— | 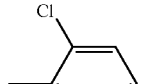 | 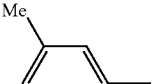 | 156-158 |
| 16-15 | 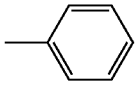 | —CO— | —NH— | 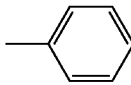 | 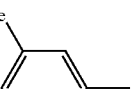 | 180-182 |
| 16-16 | 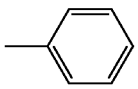 | —(CH₂)₂CO— | —NH— | 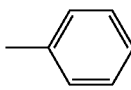 | 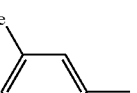 | 174-175 |
TABLE 3
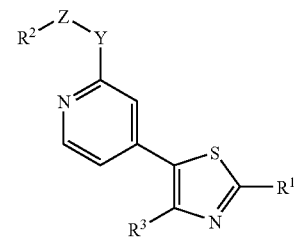
| Example Compound No. | R² | Z | Y | R¹ | R³ | mp/° C. |
|---|---|---|---|---|---|---|
| 16-17 | 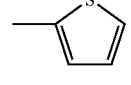 | —CO— | —NH— | 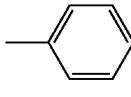 | 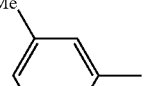 | 145-147 |
| 16-18 | 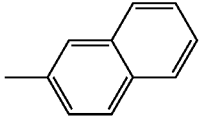 | —CO— | —NH— | 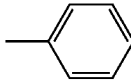 | 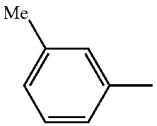 | 184-186 |

TABLE 3-continued
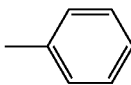
| Example Compound No. | R² | Z | Y | R¹ | R³ | mp/° C. |
|---|---|---|---|---|---|---|
| 17 | Ph | —CH₂CO— | —NMe— | —CH₂Me | 3-Me-C₆H₄ | 75-76 |
| 18 | Ph | —(CH₂)₂CO— | —NMe— | —CH₂Me | 3-Me-C₆H₄ | oil |
| 19-1 | Ph | —CH₂— | —NH— | —Me | 4-MeO-C₆H₄ | 132-133 |
| 19-2 | Ph | —CH₂— | —NH— | —CH₂Me | 3-Me-C₆H₄ | 106-107 |
| 19-3 | Ph | —(CH₂)₂— | —NH— | —CH₂Me | 3-Me-C₆H₄ | 97-98 |
| 19-4 | Ph | —(CH₂)₃— | —NH— | —CH₂Me | 3-Me-C₆H₄ | 52-53 |
| 19-5 | Ph | —CH₂— | —NH— | —(CH₂)₂Me | 3-Me-C₆H₄ | oil |
| 19-6 | Ph | —(CH₂)₂— | —NH— | —(CH₂)₂Me | 3-Me-C₆H₄ | oil |
| 19-7 | Ph | —(CH₂)₃— | —NH— | —(CH₂)₂Me | 3-Me-C₆H₄ | oil |

TABLE 3-continued
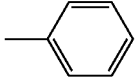
| Example Compound No. | R² | Z | Y | R¹ | R³ | mp/° C. |
|---|---|---|---|---|---|---|
| 19-8 | 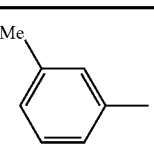 | —CH₂— | —NH— | —(CH₂)₃Me | 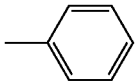 | oil |
| 19-9 | 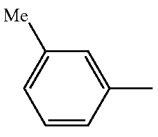 | —(CH₂)₂— | —NH— | —(CH₂)₃Me | 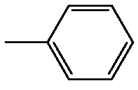 | oil |
TABLE 4
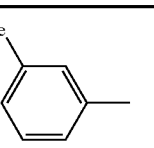
| Example Compound No. | R² | Z | Y | R¹ | R³ | mp/° C. |
|---|---|---|---|---|---|---|
| 19-10 | 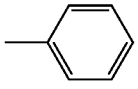 | —(CH₂)₃— | —NH— | —(CH₂)₃Me | 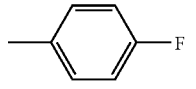 | oil |
| 19-11 | 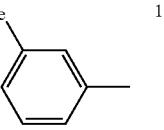 | —CH₂— | —NH— | 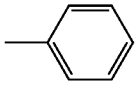 |  | 143-146 |
| 19-12 | 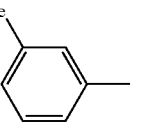 | —(CH₂)₂— | —NH— | 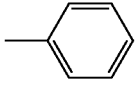 | 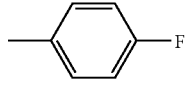 | 97-98 |
| 19-13 | 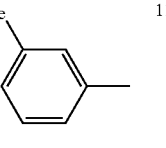 | —(CH₂)₃— | —NH— | | | 110-112 |

TABLE 4-continued

| Example Compound No. | R² | Z | Y | R¹ | R³ | mp/° C. |
|---|---|---|---|---|---|---|
| 19-14 | phenyl | —CH₂— | —NH— | 2-Cl-phenyl | 3-Me-phenyl | 84-86 |
| 19-15 | phenyl | —(CH₂)₂— | —NH— | 2-Cl-phenyl | 3-Me-phenyl | 113-114 |
| 19-16 | phenyl | —(CH₂)₃— | —NH— | 2-Cl-phenyl | 3-Me-phenyl | 101-102 |
| 19-17 | phenyl | —CH₂— | —NH— | 4-SMe-phenyl | 3-Me-phenyl | 134-136 |
| 19-18 | phenyl | —(CH₂)₂— | —NH— | 4-SMe-phenyl | 3-Me-phenyl | 137-139 |
| 19-19 | phenyl | —(CH₂)₃— | —NH— | 4-SMe-phenyl | 3-Me-phenyl | 106-107 |
| 19-20 | naphthyl | —CH₂— | —NH— | 4-SMe-phenyl | 3-Me-phenyl | 144-145 |
| 20 | phenyl | —CO— | —NH— | 4-SO₂Me-phenyl | 3-Me-phenyl | 212-214 |

TABLE 5

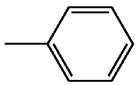

| Example Compound No. | R² | Z | Y | R¹ | R³ | mp/° C. |
|---|---|---|---|---|---|---|
| 21-1 | phenyl | —CH₂CO— | —NH— | 4-(SO₂Me)phenyl | 3,5-dimethylphenyl | 244-245 |
| 21-2 | phenyl | —(CH₂)₂CO— | —NH— | 4-(SO₂Me)phenyl | 3,5-dimethylphenyl | 236-237 |
| 21-3 | 2-thienyl | —CO— | —NH— | 4-(SO₂Me)phenyl | 3,5-dimethylphenyl | 199-201 |
| 21-4 | 2-naphthyl | —CO— | —NH— | 4-(SO₂Me)phenyl | 3,5-dimethylphenyl | 231-233 |
| 21-5 | phenyl | —CH₂— | —NH— | 4-(SO₂Me)phenyl | 3,5-dimethylphenyl | 148-150 |
| 21-6 | phenyl | —(CH₂)₃— | —NH— | 4-(SO₂Me)phenyl | 3,5-dimethylphenyl | 167-168 |
| 21-7 | 2-naphthyl | —CH₂— | —NH— | 4-(SO₂Me)phenyl | 3,5-dimethylphenyl | 167-168 |
| 22 | phenyl | —CH₂— | —NH— | —NH₂ | 3,5-dimethylphenyl | 178-179 |
| 23-1 | 4-MeO-phenyl | —CH₂— | —NH— | —NH₂ | 3,5-dimethylphenyl | 183-184 |

TABLE 5-continued
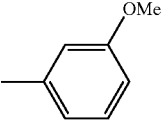
| Example Compound No. | R² | Z | Y | R¹ | R³ | mp/° C. |
|---|---|---|---|---|---|---|
| 23-2 | 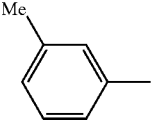 | —CH₂— | —NH— | —NH₂ | 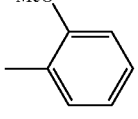 | 152-154 |
| 23-3 | 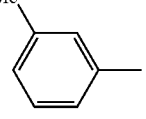 | —CH₂— | —NH— | —NH₂ |  | 158-159 |
| 23-4 | 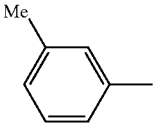 | —CH₂— | —NH— | —NH₂ | 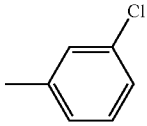 | 182-183 |
| 23-5 | 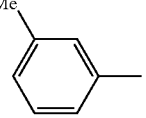 | —CH₂— | —NH— | —NH₂ | 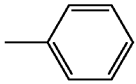 | 180-181 |
| 23-6 | 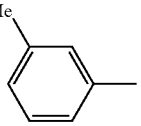 | —CHMe—(R) | —NH— | —NH₂ | 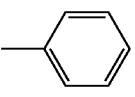 | 94-98 |
TABLE 6
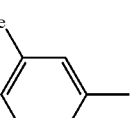
| Example Compound No. | R² | Z | Y | R¹ | R³ | mp/° C. |
|---|---|---|---|---|---|---|
| 23-7 | 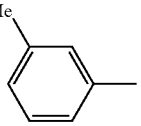 | —CHMe—(S) | —NH— | —NH₂ | 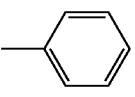 | 93-96 |

TABLE 6-continued
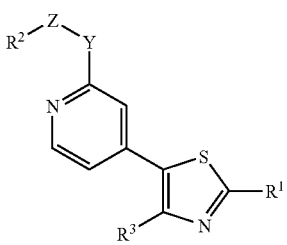
| Example Compound No. | R² | Z | Y | R¹ | R³ | mp/° C. |
|---|---|---|---|---|---|---|
| 23-8 | 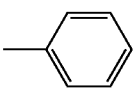 | —CH₂— | —NMe— | —NH₂ | 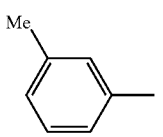 | 138-140 |
| 24 | 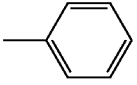 | —CH₂— | —NH— | —NH₂ | 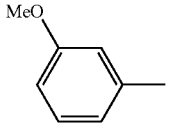 | 217-218 |
| 25-1 | 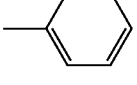 | —(CH₂)₂— | —NH— | 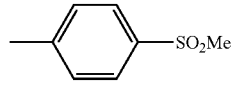 | 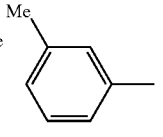 | 174-176 |
| 25-2 | 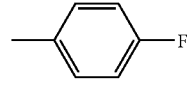 | —CH₂— | —NH— | 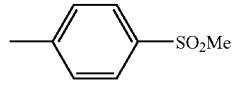 | 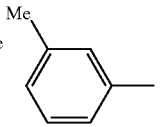 | 155-158 |
| 25-3 | 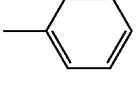 | —CH₂— | —NMe— | 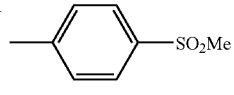 | 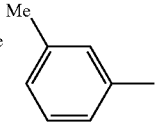 | 165-166 |
| 25-4 | 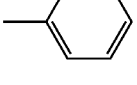 | —(CH₂)₂— | —NMe— | 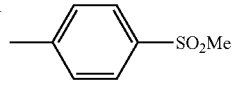 | 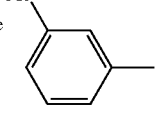 | 116-117 |
| 25-5 | 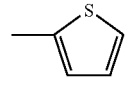 | —CH₂— | —NH— | 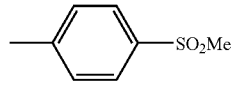 | 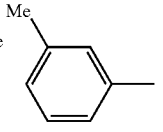 | 107-109 |
| 26 | 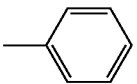 | — | —S— | 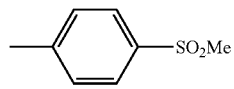 | 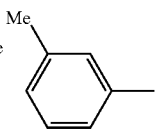 | 116-118 |

TABLE 6-continued

| Example Compound No. | R² | Z | Y | R¹ | R³ | mp/° C. |
|---|---|---|---|---|---|---|
| 27 | phenyl (4-methyl) | —CH₂— | —S— | phenyl-SO₂Me | 3-methylphenyl (Me) | 182-185 |
| 28 | phenyl | — | —SO₂— | phenyl-SO₂Me | 3-methylphenyl (Me) | 126-128 |

Preparation Example 1

| | |
|---|---|
| (1) Compound of Example 1 | 50 mg |
| (2) Lactose | 34 mg |
| (3) Corn starch | 10.6 mg |
| (4) Corn starch (pasty) | 5 mg |
| (5) Magnesium stearate | 0.4 mg |
| (6) Calcium carboxymethylcellulose | 20 mg |
| Total | 120 mg |

According to the conventional method, the above (1) to (6) were mixed, compressed with a compressing machine to obtain tablets.

Preparation Example 2

| | |
|---|---|
| (1) Example compound 16-1 | 10.0 mg |
| (2) Lactose | 60.0 mg |
| (3) Corn starch | 35.0 mg |
| (4) Gelatin | 3.0 mg |
| (5) Magnesium stearate | 2.0 mg |

10.0 mg of Example Compound 16-1 and a mixture of 60.0 mg of lactose and 35.0 mg of corn starch were granulated by passing through a 1 mm mesh sieve using 0.03 ml of a 10% aqueous gelatin solution (3.0 mg as gelatin) and, thereafter, dried at 40° C. and re-passed through a sieve. The granules thus obtained were mixed with 2.0 mg of magnesium stearate and compressed. The resulting core tablet is coated with a sugar coating of a suspension of sucrose, titanium dioxide, talc and arabic gum in water. The tablet coated with a coating is polished with beeswax to obtain a coated tablet.

Preparation Example 3

| | |
|---|---|
| (1) Example compound 16-1 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

After 10.0 mg of Example Compound 16-1 and 3.0 mg of magnesium stearate are granulated with 0.07 ml of an aqueous solution of soluble starch (7.0 mg as soluble starch), the granules are dried and mixed with 70.0 mg of lactose and 50.0 mg of corn starch. The mixture is compressed to obtain tablets.

Preparation Example 4

| | |
|---|---|
| (1) Example compound 18 | 5.0 mg |
| (2) Sodium chloride | 20.0 mg |
| (3) Distilled water | to total 2 ml |

5.0 mg of Example Compound 18 and 20.0 mg of sodium chloride are dissolved in distilled water and water is added to total 2.0 ml. The solution is filtered and filled into a 2 ml of ampule under sterile conditions. After the ampule is sterilized, it is sealed to obtain a solution for injection.

Experimental Example 1

Genetic procedures were according to a method described in Molecular Cloning, published by Cold Spring Harbor, Laboratory, 1989 or a method described in the attached protocol of the reagent.

1) Cloning of Human Adenosine $A_3$ Receptor

Cloning of an adenosine $A_3$ receptor gene was performed from human brain cDNA by a PCR method. A PCR reaction was performed with a DNA thermal cycler 480 (Perkin Elmer) by using 1 ng of brain cDNA (Toyobo, QUICK-Clone cDNA) as a template, adding each 50 pmol of a primer set 5'-CGCCTCTAGACAAGATGCCCAACAA-CAGCACTGC-3' (SEQ ID NO: 1) and 5'-CGGGGTCGA-CACTACTCAGAATTCTTCTCAATGC-3' (SEQ ID NO: 2) made by reference to adenosine $A_3$ receptor gene base sequence reported by Salvatore et al. (Proc. Natl. Acad. Sci. U.S.A., 90:10365-10369, 1993) and employing Takara LA PCR Kit Ver. 2 (Takara Shuzo) (reaction conditions: 35 cycles of 1 minute at 95° C., 1 minute at 66° C., 2 minutes at 75° C.). The resulting PCR product was subjected to agarose gel electrophoresis and 1.0 kb of DNA fragment was recovered and, thereafter, an adenosine $A_3$ receptor gene was cloned using Original TA Cloning Kit (Funakoshi).

Next, the resulting plasmid was digested with a restriction enzyme XbaI (Takara Shuzo), treated with T4 DNA polymerase (Takara Shuzo) into end-blunted fragments and further digested with SalI (Takara Shuzo) to obtain adenosine $A_3$ receptor gene fragments.

2) Preparation of a Plasmid for Expressing of Human Adenosine $A_3$ Receptor

A SRα promoter derived from pTB1411 described in JP-A 5-076385 was digested with BglII (Takara Shuzo), blunted, and ligated to EcoRI (Takara Shuzo)-digested pCI vector (Promega) with a DNA Ligation kit (Takara Shuzo) to make pCI-SRα. Next, this pCI-SRα was digested with ClaI (Takara Shuzo) and treated with T4 DNA polymerase (Takara Shuzo) to blunt-ended. On the other hand, after pGFP-C1 (Toyobo) was digested with Bsu36I (Daiichi Pure Chemicals), treated with T4 DNA polymerase (Takara Shuzo) to blunt-ended. On the other hand, after pGFP-C1 (Toyobo) was digested with Bsu36I (Daiichi Pure Chemicals), treated with T4 DNA polymerase (Takara Shuzo) to blunted end to obtain 1.63 kb of DNA fragment, and both were ligated with a DNA Ligation kit (Takara Shuzo) and competent cells of Escherichia coli JM109 were transformed to obtain the plasmid pMSRαneo.

Next, after pMSRαneo was digested with EcoRI (Takara Shuzo), treated with a T4 DNA polymerase (Takara Shuzo) to blunted end, and further digesting with SalI (Takara Shuzo) to obtain a 5.4 kb DNA fragment. The obtained DNA fragment and the fragments of adenosine $A_3$ receptor gene obtained in the above 1) were mixed, ligated with a DNA Ligation kit (Takara Shuzo) and competent cells of Escherichia coli JM109 (Takara Shuzo) were transformed to obtain the plasmid $pA_3SR\alpha$.

3) Introduction of a Plasmid for Expressing Human Adenosine $A_3$ Receptor into CHO (dhfr-) Cells and Expression CHO (dhfr-) cells obtained by culturing on Ham F12 medium (Nihonseiyaku) containing 10% bovine fetal serum (Lifetec Oriental) in a 750 ml tissue culture flask (Vecton Dickinson) were peeled with 0.5 g/L trypsin-0.2 g/L EDTA (Lifetec Oriental) and, thereafter, the cells were washed with PBS (Lifetec Oriental) and centrifuged (1000 rpm, 5 minutes), which was suspended in PBS.

Next, a DNA was introduced into cells using a gene pulser (BioRad) according to the following conditions. That is, $8\times10^6$ cells and 10 µg of the plasmid $pA_3SR\alpha$ for expressing human adenosine $A_3$ receptor were added to 0.4 cm gapped cuvette and electroporation was performed with 0.8 ml volume, and under voltage 0.25 kV and capacitance 960 µF. Thereafter, the cells were transferred to Ham F12 medium containing 10% bovine fetal serum, cultured for 24 hours, the cells were peeled again and centrifuged, then, suspended in Ham F12 medium containing 10% bovine fetal serum to which Geneticin (Lifetec Oriental) had been added to 500 µg/ml, which was diluted to $10^4$ cells/ml to seed on a 96-well plate (Becton Dickinson) to obtain Geneticin-resistant strain.

Next, the resulting Geneticin-resistant strain was cultured on a 24 well-plate (Becton Dickinson) and, thereafter, an adenosine $A_3$ receptor expressing cell was selected among the resistant strains. That is, a reaction was conducted in an assay buffer I (HBSS (Wako Pure Chemicals) containing 0.1% BSA, 0.25 mM PMSF, 1 µg/ml pepstatin and 20 µg/ml leupeptin) for 1 hour, washed with an assay buffer I, the radioactivity was measured with a γ-counter to select a cell to which a ligand is specifically bound, $A_3AR/CHO$ strain.

4) Preparation of a Cell Membrane Fraction of a Cell for Expressing Adenosine $A_3$ Receptor After the $A_3AR/CHO$ strain obtained in the above 3) was cultured in Ham F12 medium containing 10% bovine fetal serum for 2 days, the cells were peeled with 0.02% EDTA-containing PBS, the cells were recovered by centrifugation, suspended in an assay buffer II (50 mM Tris-hydrochloric acid (pH 7.5), 1 mM EDTA, 10 mM magnesium chloride, 0.25 mM PMSF, 1 µg/mL pepstatin, 20 µg/ml leupeptin), and the cells were lysed by treating three times with a polytron homogenizer (Model PT-3000, KINEMATICA AG) at 20,000 rpm for 20 seconds. After the cells were ground, they were centrifuged at 20,000 rpm for 10 minutes to obtain the supernatant containing the membrane fraction. This supernatant was centrifuged with a supercentrifuge (Model L8-70M, rotor 70Ti, Beckmann) at 30,000 rpm for 1 hour to obtain the precipitates containing the membrane fraction.

Next, the precipitates were suspended in an assay buffer II containing 2 unit/ml adenosine deaminase (Boehringer Mannheim), treated at 30° C. for 30 minutes and, thereafter, centrifuged again as described above to obtain the precipitates containing the membrane fraction.

5) Adenosine $A_3$ Receptor Binding Test

On a 96 well-microplate, [$^3$H]-NECA (Amersham) as a ligand was added to an assay buffer II containing the 100 µg/ml membrane fraction obtained in the above 4) and various concentrations of test compounds so that the concentration of the ligand was 10 nM, followed by reaction at room temperature for 1 hour. Then, the membrane fraction was transferred to unifilter GF/C (Packard) by filtering the reaction solution using Cell Harvester (Packard) and washed three times with 50 mM cooled Tris buffer (pH 7.5). After the filter was dried, Microscint 0 (Packard) was added to the filter, the radioactivity was measured with a TopCount (Packard) and the concentration ($IC_{50}$) of a test compound necessary for decreasing an amount of binding of [$^3$H]-NECA to the membrane fraction by 50% was calculated with PRISM 2.01 (Graphpad Software).

As the result, the $IC_{50}$ value of the compound of Example 1 was 11.6 nM. It can be seen that Compound (I) is the excellent affinity for adenosine $A_3$ receptor.

Experimental Example 2

The genetic manipulations described below were according to a method described in the book (Maniatis et al., Molecular Cloning, Cold Spring Harbor Laboratory, 1989) or a method described in the protocol attached to the reagent.

(1) Cloning of Human p38 MAP Kinase Gene and Preparation of Recombinant Baculovirus Cloning of human p38 MAP kinase gene was performed by a PCR method using a primer set P38-U:5'-ACCACTC-GAGATGGACTACAAGGACGACGATGA-CAAGTCTCAGGAGAGGCCCACGTTCTACC-3' [SEQ ID NO: 3] and PAG-L:5'-ACCCGGTACCACCAGGTGCT-CAGGACTCCATCTCT-3'[SEQ ID NO: 4] made by reference to the base sequence of p38 MAP kinase gene reported by Han et al. (Science 265 (5173), 808-811 (1994)) and employing kidney cDNA (Toyobo, QUICK-Clone cDNA) as a template.

A PCR reaction was performed by a Hot Start method using AmpliWax PCR Gem 100 (Takara Shuzo). As the lower mixed solution, 2 μL 10×LA PCR Buffer, 3 μL 2.5 mM dNTP solution, each 2.5 μL of 12.5 μM primer solution, and 10 μL sterile distilled water were mixed. As the upper mixed solution, 1 μL human cardiac cDNA (1 ng/mL) as a template, 3 μL 10×LA PCR Buffer, 1 μL 2.5 mM dNTP solution, 0.5 μL TaKaRa LA Taq DNA polymerase (Takara Shuzo), and 24.5 μL sterile distilled water were mixed. One AmpliWax PCR Gem 100 (Takara Shuzo) was added to the prepared lower mixed solution to treat at 70° C. for 5 minutes and for 5 minutes in an ice and, thereafter, the upper mixed solution was added to prepare a reaction solution for PCR. A tube containing the reaction solution was set at a thermal cycler (Perkin Elmer), which was treated at 95° C. for 2 minutes. Further, after repeating 35 times a cycle of 15 seconds at 95° C. and 2 minutes at 68° C., treatment was performed at 72° C. for 8 minutes. The resulting PCR product was subjected to agarose gel (1%) electrophoresis, 1.1 kb DNA fragment containing p38 MAP kinase gene was recovered from the gel and, thereafter, which was inserted into pT7Blue-T vector (Takara Shuzo) to make the plasmid pHP38.

The 4.8 kb XhoI-KpnI fragment of the plasmid pFAST-BAC1 (CIBCOBRL) and the 1.1 kb XhoI-Kpn fragment of the above plasmid pHP38 were ligated to make the plasmid pFBHP38.

The plasmid pFBHP38 and BAC-TO-BAC Baculovirus Expression System (GIBCOBRL) were used to prepare the recombinant Baculovirus virusstock BAC-HP38.

(2) Cloning of Human MKK3 Gene and Preparation of Recombinant Baculovirus

Cloning of human MKK3 gene was performed by a PCR method using a primer set MKK-U:5'-ACAAGAATTCAT-AACATATGGCTCATCATCATCATCAT-CATTCCAAGCCACCCGCACCCAA-3' [SEQ ID NO: 5] and MKK-L: 5'-TCCCGTCTAGACTATGAGTCTTCTC-CCAGGAT-3' [SEQ ID NO: 6] made by reference to the base sequence of MKK3 gene reported by Derijard, B. et al., Science 267 (5198), 682-685 (1995) and using kidney cDNA (Toyobo, QUICK-Clone cDNA).

A PCR reaction was performed by a Hot Start method using AmpliWax PCR Gem 100 (Takara Shuzo). As the lower mixed solution, 2 μL 10×LA PCR Buffer, 3 μL 2.5 mM dNTP solution, each 2.5 μL of 12.5 μM primer solution, and 10 μL sterile distilled water were mixed. As the upper mixed solution, 1 μL human kidney cDNA (1 ng/mL), 3 μL 10×LA PCR Buffer, 1 μL 2.5 mM dNTP solution, 0.5 μL TaKaRa LA taq DNA polymerase (Takara Shuzo) and 24.5 μL sterile distilled water were mixed. One AmpliWax PCR Gem 100 (Takara Shuzo) was added to the prepared lower mixed solution to treat at 70° C. for 5 minutes and for 5 minutes in an ice and, thereafter, the upper mixed solution was added to prepare a reaction solution for PCR. A tube containing the reaction solution was set at a thermal cycler (Perkin Elmer), which was treated at 95° C. for 2 minutes. Further, after repeating 35 times a cycle of 15 seconds at 95° C. and 2 minutes at 68° C., treatment was performed at 72° C. for 8 minutes. The resulting PCR product was subjected to agarose gel (1%) electrophoresis, 1.0 kb DNA fragment containing MKK3 gene was recovered from the gel and, thereafter, which was inserted into pT7Blue-T vector (Takara Shuzo) to make the plasmid pHMKK3.

In order to mutate MKK3 into a constitutive active form (from Ser to Glu at 189 position, from Thr to Glu at position 193), a primer set SER-U:5'-GGCTACTTGGTGGACGAG-GTGGCCAAGGAGATGGATGCCGGCTGC-3' [SEQ ID NO: 7] and SER-L:5'-GCAGCCGGCATCCATCTCCTTG-GCCACCTCGTCCACCAAGTAGCC-3' [SEQ ID NO: 8] was used to introduce a mutation by QuickChange Site-Directed Mutagenesis Kit (Stratagene), to obtain pcaMKK3.

4.8 kb EcoRI-XbaI fragment of the plasmid pFASTBAC1 (CIBCOBRL) and the 1.0 kb EcoRI-XbaI fragment of the above plasmid pcaMKK 3 were ligated to make the plasmid pFBcaMKK3.

The plasmid pFBcaMKK3 and BAC-TO-BAC Baculovirus Expression System (GIBCOBRL) were used to prepare the recombinant Baculovirus virusstock BAC-caMKK3.

(3) Preparation of Active form p38 MAP Kinase

The Sf-21 cells were seeded on 100 ml Sf-900II SFM medium (GIBCOBRL) to 1×10$^6$ cells/mL and cultured at 27° C. for 24 hours. After each 0.2 mL of the virusstock BAC-HP38 of recombinant Baculovirus and BAC-caMKK3 were added, the culturing was further performed for 48 hours. After the cells were separated from the culturing solution by centrifugation (3000 rpm, 10 min), the cells were washed twice with PBS. After the cells were suspended in 10 ml Lysis buffer (25 mM HEPES (pH 7.5), 1% Triton X, 130 mM NaCl, 1 mM EDTA, 1 mM DTT, 25 mM β-glycero-phosphate, 20 mM leupeptin, 1 mM APMSF, 1 mM Sodium orthovanadate), the cells were lysed by treating twice with a homogenizer (POLYTRON) at 20000 rpm for 2 minutes. By using Anti-FLAG M2 Affinity Gel (Eastman Chemical) from the supernatant obtained by centrifugation (40000 rpm, 45 minutes), active form p38 MAP kinase was purified.

(4) Measurement of the p38 MAP Kinase Inhibitory Activity 2.5 μL of a test compound dissolved in DMSO was added to 37.5 μL reaction solution (25 mM HEPES (pH 7.5), 10 mM Magnesium Acetate) containing 260 ng active form p38 MAP kinase and 1 μg Myelin Basic Protein, which was maintained at 30° C. for 5 minutes. The reaction was initiated by adding 10 μL ATP solution (2.5 μm ATP, 0.1 μCi [g-$^{32}$P]ATP). After the reaction was performed at 30° C. for 60 minutes, the reaction was stopped by adding 50 μL 20% TCA solution. After the reaction solution was allowed to stand at 0° C. for 20 minutes, an acid insoluble fraction was transferred to GF/C filter (Packard Japan) using Cell Harvester (Packard Japan) and washed with 250 mM H$_3$PO$_4$. After drying at 45° C. for 60 minutes, 40 μM Microscint 0 (Packard Japan) was added and the radioactivity was measured with a TopCount (Packard Japan). The concentration (IC$_{50}$ value) necessary for inhibiting uptake of $^{32}$P into an acid insoluble fraction by 50% was calculated with PRISM 2.01 (Graphpad Software).

The results are shown in Table 7.

TABLE 7

| Example No. | IC$_{50}$ (μM) |
|---|---|
| 1 | 0.43 |
| 2 | 0.063 |
| 3 | 0.023 |
| 4 | 0.020 |
| 5 | 0.029 |
| 6 | 0.023 |

From this, it can be seen that Compound (I) has the p38 MAP kinase inhibitory activity.

Experimental Example 3

Measurement of Inhibiting Activity of TNF-α Production

After THP-1 cells which had been cultured on PRMI 1640 medium (manufactured by Life Technologies, Inc.) containing 1% non-activated bovine fetal serum (manufactured by Life Technologies, Inc., U.S.A.) and 10 mM HEPES (pH 7.5) seeded on a 96-well plate to $1 \times 10^5$ cells/well, 1 μL test compound dissolved in DMSO was added to there. After incubation at 37° C. for 1 hour in a $CO_2$ incubator, LPS (Wako Pure Chemicals) was added to the final concentration 5 μg/mL. After cultured at 37° C. for 4 hours in a $CO_2$ incubator, the supernatant was obtained by centrifugation. The concentration of TNF-α in the supernatant was measured with ELISA (R&D System, Quantikine Kit). The concentration ($IC_{50}$ value) necessary for inhibiting TNF-α production by 50% was calculated by PRIMS 2.01 (Graphpad Software).

The results are shown in Table 8.

TABLE 8

| Example No. | $IC_{50}$ (μM) |
|---|---|
| 3 | 0.026 |
| 4 | 0.014 |
| 5 | 0.020 |
| 6 | 0.140 |

From this, it can be seen that Compound (I) has the excellent inhibitory activity of TNF-α production.

INDUSTRIAL APPLICABILITY

Compound (I) or a salt thereof has the excellent adenosine $A_3$ receptor antagonism and can be used as an agent for preventing or treating adenosine $A_3$ receptor related diseases. Further, Compound (I) or a salt thereof shows the excellent p38 MAP kinase inhibiting activity and TNF-α inhibiting activity, and can be also used as an agent for preventing or treating p38 MAP kinase related diseases and TNF-α related diseases.

What is claimed is:

1. An optionally N-oxidized compound represented by the formula:

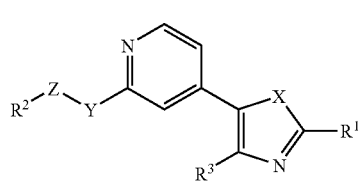

(I)

wherein R₁ represents (i) a hydrogen atom, (ii) a $C_{1-6}$ alkyl group, a $C_{2-6}$ alkenyl group, a $C_{2-6}$ alkynyl group, a $C_{3-6}$ cycloalkyl group, a $C_{6-14}$ aryl group or a $C_{7-16}$ aralkyl group [wherein these groups may have substituents selected from the group (substituent group A) consisting of oxo, halogen atom, $C_{1-3}$ alkylenedioxy, nitro, cyano, optionally halogenated $C_{1-6}$ alkyl, optionally halogenated $C_{2-6}$ alkenyl, carboxy $C_{2-6}$ alkenyl, optionally halogenated $C_{2-6}$ alkynyl, optionally halogenated $C_{3-6}$ cycloalkyl, $C_{6-14}$ aryl, optionally halogenated $C_{1-8}$ alkoxy, $C_{1-6}$ alkoxy-carbonyl-$C_{1-6}$- alkoxy, hydroxy, C$_{6-14}$ aryloxy, C$_{7-16}$ aralkyloxy, mercapto, optionally halogenated C$_{1-6}$ alkylthio, C$_{6-14}$ arylthio, C$_{7-16}$ aralkylthio, amino, mono-C$_{1-6}$ alkylamino, mono-C$_{6-14}$ arylamino, di-C$_{1-6}$ alkylamino, di-C$_{6-14}$ arylamino, formyl, carboxy, C$_{1-6}$ alkyl-carbonyl, C$_{3-6}$ cycloalkyl-carbonyl, C$_{1-6}$ alkoxy-carbonyl, C$_{6-14}$ aryl-carbonyl, C$_{7-16}$ aralkyl-carbonyl, C$_{6-14}$ aryloxy-carbonyl, C$_{7-16}$ aralkyloxy-carbonyl, carbamoyl, thiocarbamoyl, mono-C$_{1-6}$ alkyl-carbamoyl, di-C$_{1-6}$ alkyl-carbamoyl, C$_{6-14}$ aryl-carbamoyl, C$_{1-6}$ alkylsulfonyl, C$_{6-14}$ arylsulfonyl, C$_{1-6}$ alkylsulfinyl, C$_{6-14}$ arylsulfinyl, formylamino, C$_{1-6}$ alkyl-carbonylamino, C$_{6-14}$ aryl-carbonylamino, C$_{1-6}$ alkoxy-carbonylamino, C$_{1-6}$ alkylsulfonylamino, C$_{6-14}$ arylsulfonylamino, C$_{1-6}$ alkyl-carbonyloxy, C$_{6-14}$ aryl-carbonyloxy, C$_{1-6}$ alkoxy-carbonyloxy, mono-C$_{1-6}$ alkyl-carbamoyloxy, di-C$_{1-6}$ alkyl-carbamoyloxy, C$_{6-14}$ aryl-carbamoyloxy, sulfo, sulfamoyl, sulfinamoyl and sulfenamoyl], (iii) an acyl group represented by the formula:

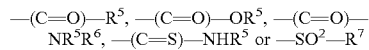
—(C═O)—R$^5$, —(C═O)—OR$^5$, —(C═O)—NR$^5$R$^6$, —(C═S)—NHR$^5$ or —SO$^2$—R$^7$ wherein R$^5$ represents ① a hydrogen atom or ② a C$_{1-6}$ alkyl group, a C$_{2-6}$ alkenyl group, a C$_{2-6}$ alkynyl group, a C$_{3-6}$ cycloalkyl group, a C$_{6-14}$ aryl group or a C$_{7-16}$ aralkyl group optionally having substituents selected from the substituent group A, R$^6$ represents a hydrogen atom or a C$_{1-6}$ alkyl group, R$^7$ represents a C$_{1-6}$ alkyl group, a C$_{2-6}$ alkenyl group, a C$_{2-6}$ alkynyl group, a C$_{3-6}$ cycloalkyl group, a C$_{6-14}$ aryl group or a C$_{7-16}$ aralkyl group optionally having substituents selected from the substituent group A, or (iv) an amino group optionally having substituents selected from the group consisting of ① a C$_{1-6}$ alkyl group, a C$_{2-6}$ alkenyl group, a C$_{2-6}$ alkynyl group, a C$_{3-6}$ cycloalkyl group, a C$_{6-14}$ aryl group or a C$_{7-16}$ aralkyl group optionally having substituents selected from the substituent group A, ② an acyl group as defined in the (iii), and ③ a C$_{1-6}$ alkylidene group optionally having substituents selected from the substituent group A, R$^2$ represents a C$_{6-14}$ monocyclic or fused polycyclic aromatic hydrocarbon group optionally having substituents selected from the substituent group A;

R$^3$ represents ① a hydrogen atom or ② a C$_{6-14}$ aryl group optionally having substituents selected from the substituent group A;

X represents an optionally oxidized sulfur atom,

Y represents a bond, an oxygen atom, an optionally oxidized sulfur atom or a group represented by the formula: NR$^4$, wherein R$^4$ represents ① a hydrogen atom, ② a C$_{1-6}$ alkyl group, a C$_{2-6}$ alkenyl group, a C$_{2-6}$ alkynyl group, a C$_{3-6}$ cycloalkyl group, a C$_{6-14}$ aryl group or a C$_{7-16}$ aralkyl group optionally having substituents selected from the substituent group A or ③ an acyl group as defined in the (iii), and Z represents a bond, a C$_{1-15}$ alkylene group, a C$_{2-16}$ alkenylene group or a C$_{2-16}$ alkynylene group optionally having substituents selected from the substituent group A, or a salt thereof.

2. The compound according to claim 1, wherein Z is a C$_{1-15}$ alkylene group, a C$_{2-16}$ alkenylene group or a C$_{2-16}$ alkynylene group optionally having substituents selected from the substituent group A.

3. The compound according to claim 1, which is a compound represented by the formula:

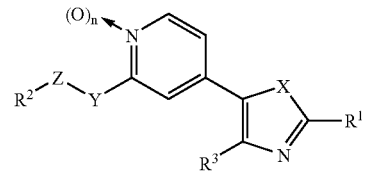

wherein n represents 0 or 1, and other symbols are as defined in claim 1, or a salt thereof.

4. The compound according to claim 1, wherein R$^1$ represents (i) a hydrogen atom, (ii) a C$_{1-6}$ alkyl group, a C$_{2-6}$ alkenyl group, a C$_{2-6}$ alkynyl group, a C$_{3-6}$ cycloalkyl group, a C$_{6-14}$ aryl group or a C$_{7-16}$ aralkyl group [wherein these groups may have substituents selected from the substituent group A], (iii) an acyl group represented by the formula:

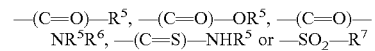
—(C═O)—R$^5$, —(C═O)—OR$^5$, —(C═O)—NR$^5$R$^6$, —(C═S)—NHR$^5$ or —SO$_2$—R$^7$ wherein R$^5$ represents ① a hydrogen atom or ② a C$_{1-6}$ alkyl group, a C$_{2-6}$ alkenyl group, a C$_{2-6}$ alkynyl group, a C$_{3-6}$ cycloalkyl group, a C$_{6-14}$ aryl group or a C$_{7-16}$ aralkyl group optionally having substituents selected from the substituent group A, R$^6$ represents a hydrogen atom or a C$_{1-6}$ alkyl group, R$^7$ represents a C$_{1-6}$ alkyl group, a C$_{2-6}$ alkenyl group, a C$_{2-6}$ alkynyl group, a C$_{3-6}$ cycloalkyl group, a C$_{6-14}$ aryl group or a C$_{7-16}$ aralkyl group optionally having substituents selected from the substituent group A, or (iv) an amino group, wherein the amino group may have substituents selected from the group consisting of ① a C$_{1-6}$ alkyl group, a C$_{2-6}$ alkenyl group, a C$_{2-6}$ alkynyl group, a C$_{3-6}$ cycloalkyl group, a C$_{6-14}$ aryl group or a C$_{7-16}$ aralkyl group optionally having substituents selected from the substituent group A, ② an acyl group as defined in the (iii), and ③ a C$_{1-6}$ alkylidene group optionally having substituents selected from the substituent group A, R$^2$ represents a C$_{6-14}$ monocyclic or fused polycyclic aromatic hydrocarbon group optionally having substituents selected from the substituent group A;

R$^3$ represents ① a hydrogen atom or ② a C$_{6-14}$ monocyclic or fused polycyclic aromatic hydrocarbon group optionally having substituents selected from the substituent group A;

X represents S, SO or SO$_2$; and

Y represents a bond, O, S, SO, SO$_2$ or a group represented by the formula: NR$^4$, wherein R$^4$ represents ① a hydrogen atom, ② a C$_{1-6}$ alkyl group, a C$_{2-6}$ alkenyl group, a alkynyl group, a C$_{3-6}$ cycloalkyl group, a C$_{6-14}$ aryl or a C$_{7-16}$ aralkyl group optionally having substituents selected from the substituent group A or ③ an acyl group as defined in the (iii).

5. The compound according to claim 1, wherein R$^1$ is an amino group, as defined in (iv) of claim 1.

6. The compound according to claim 1, wherein R$^1$ is (i) a C$_{1-6}$ alkyl group, (ii) a C$_{6-14}$ aryl group optionally substituted with substituents selected from the group consisting of C$_{1-6}$ alkylthio, C$_{1-6}$ alkylsulfonyl and halogen atom, or (iii) an amino group optionally having 1 or 2 acyl represented by the formula: —(C═O)—R$^{5'}$, wherein R$^{5'}$ represents ① a C$_{1-6}$ alkyl group or ② a C$_{6-14}$ aryl group.

7. The compound according to claim 1, wherein $R^1$ is an amino group optionally having 1 or 2 acyl group represented by —(C=O)—$R^{5'''}$, wherein $R^{5'''}$ represents a $C_{6-14}$ aryl group.

8. The compound according to claim 1, wherein $R^2$ is a $C_{6-14}$ aryl group optionally having substituents selected from the substituent group A.

9. The compound according to claim 1, wherein $R^2$ is a $C_{6-14}$ aryl group optionally substituted with halogen atom or $C_{1-6}$ alkoxy.

10. The compound according to claim 1, wherein $R^2$ is a $C_{6-14}$ aryl group.

11. The compound according to claim 1, wherein $R^3$ is a $C_{6-14}$ aryl group optionally having substituents selected from the substituent group A.

12. The compound according to claim 1, wherein $R^3$ is a $C_{6-14}$ aryl group optionally substituted with one or two $C_{1-6}$ alkyl or $C_{1-6}$ alkoxy.

13. The compound according to claim 1, wherein X is a sulfur atom.

14. The compound according to claim 1, wherein Y is an oxygen atom or a group represented by the formula: $NR^4$, wherein $R^4$ is as defined in claim 1.

15. The compound according to claim 1, wherein Y is an oxygen atom, an optionally oxidized sulfur atom or a group represented by the formula: $NR^{4'}$, wherein $R^{4'}$ represents a $C_{1-6}$ alkyl group.

16. The compound according to claim 1, wherein Y is O, NH or S.

17. The compound according to claim 1, wherein Z is a lower alkylene group optionally having substituents selected from the substituent group A.

18. The compound according to claim 1, wherein Z is a bond or a $C_{1-6}$ alkylene group optionally having oxo.

19. The compound according to claim 1, wherein $R^1$ is (i) a $C_{1-6}$ alkyl group, (ii) a $C_{6-14}$ aryl group optionally substituted with $C_{1-6}$ alkylthio, $C_{1-6}$ alkylsulfonyl or halogen atom, or (iii) an amino group optionally having 1 or 2 acyl group represented by the formula: —(C=O)—$R^{5'}$, wherein $R^{5'}$ represents ① a $C_{1-6}$ alkyl group or ② a $C_{6-14}$ aryl group;
 $R^2$ is a $C_{6-14}$ aryl group optionally substituted with halogen atom or $C_{1-6}$ alkoxy;
 $R^3$ is a $C_{6-14}$ aryl group optionally substituted with 1 or 2 $C_{1-6}$ alkyl or $C_{1-6}$ alkoxy;
 X is a sulfur atom;
 Y is an oxygen atom, an optionally oxidized sulfur atom or a group represented by the formula: $NR^{4'}$, wherein $R^{4'}$ represents a $C_{1-6}$ alkyl group; and
 Z is a $C_{1-6}$ alkylene group optionally having oxo or $C_{1-6}$ alkyl or a bond.

20. The compound according to claim 1, wherein $R^1$ is an amino group optionally having 1 or 2 acyl represented by —(C=O)—$R^{5'''}$, wherein $R^{5'''}$ represents a $C_{6-14}$ aryl group;
 $R^2$ is a $C_{6-14}$ aryl group;
 $R^3$ is a $C_{6-14}$ aryl group optionally substituted with 1 or 2 $C_{1-6}$ alkyl or $C_{1-6}$ alkoxy;
 X is a sulfur atom; Y is O, NH or S; and Z is a bond or a $C_{1-6}$ alkylene group optionally having oxo.

21. N-[5-(2-Benzoylamino-4-pyridyl)-4-(3,5-dimethylphenyl)-1,3-thiazol-2-yl]acetamide,
 N-[5-(2-benzylamino-4-pyridyl)-4-(3,5-dimethylphenyl)-1,3-thiazol-2-yl]acetamide,
 N-[4-[4-(4-methoxyphenyl)-2-methyl-1,3-thiazol-5-yl]-2-pyridyl]benzamide,
 N-[4-[2-(4-fluorophenyl)-4-(3-methylphenyl)-1,3-thiazol-5-yl]-2-pyridyl]phenylacetamide,
 N-[4-[2-ethyl-4-(3-methylphenyl)-1,3-thiazol-5-yl]-2-pyridyl]phenylacetamide,
 N-[4-[4-(3-methylphenyl)-2-propyl-1,3-thiazol-5-yl]-2-pyridyl]phenylacetamide,
 N-[4-[2-butyl-4-(3-methylphenyl)-1,3-thiazol-5-yl]-2-pyridyl]phenylacetamide,
 N-[4-[4-(3-methylphenyl)-2-(4-methylthiophenyl)-1,3-thiazol-5-yl]-2-pyridyl]phenylacetamide,
 N-[4-[2-ethyl-4-(3-methylphenyl)-1,3-thiazol-5-yl]-2-pyridyl]benzamide,
 N-[4-[2-ethyl-4-(3-methylphenyl)-1,3-thiazol-5-yl]-2-pyridyl]-3-phenylpropionamide,
 N-[4-[2-ethyl-4-(3-methylphenyl)-1,3-thiazol-5-yl]-2-pyridyl]-3-(4-methoxyphenyl)propionamide,
 N-[4-[2-ethyl-4-(3-methylphenyl)-1,3-thiazol-5-yl]-2-pyridyl]-4-phenylbutyramide,
 N-[4-[4-(3-methylphenyl)-2-propyl-1,3-thiazol-5-yl]-2-pyridyl]benzamide,
 N-[4-[4-(3-methylphenyl)-2-propyl-1,3-thiazol-5-yl]-2-pyridyl]-3-phenylpropionamide,
 N-[4-[2-butyl-4-(3-methylphenyl)-1,3-thiazol-5-yl]-2-pyridyl]benzamide,
 N-[4-[2-butyl-4-(3-methylphenyl)-1,3-thiazol-5-yl]-2-pyridyl]-3-phenylpropionamide,
 N-[4-[2-(4-fluorophenyl)-4-(3-methylphenyl)-1,3-thiazol-5-yl]-2-pyridyl]benzamide,
 N-[4-[2-(4-fluorophenyl)-4-(3-methylphenyl)-1,3-thiazol-5-yl]-2-pyridyl]-3-phenylpropionamide,
 N-[4-[4-(3-methylphenyl)-2-(4-methylthiophenyl)-1,3-thiazol-5-yl]-2-pyridyl]benzamide,
 N-[4-[4-(3-methylphenyl)-2-(4-methylthiophenyl)-1,3-thiazol-5-yl]-2-pyridyl]-3-phenylpropionamide,
 N-benzyl-N-[4-[2-ethyl-4-(3-methylphenyl)-1,3-thiazol-5-yl]-2-pyridyl]amine,
 N-[4-[2-ethyl-4-(3-methylphenyl)-1,3-thiazol-5-yl]-2-pyridyl]-N-(2-phenylethyl)amine,
 N-[4-[2-ethyl-4-(3-methylphenyl)-1,3-thiazol-5-yl]-2-pyridyl]-N-(3-phenylpropyl)amine,
 N-benzyl-N-[4-[4-(3-methylphenyl)-2-propyl-1,3-thiazol-5-yl]-2-pyridyl]amine,
 N-[4-[4-(3-methylphenyl)-2-propyl-1,3-thiazol-5-yl]-2-pyridyl]-N-(2-phenylethyl)amine,
 N-[4-[4-(3-methylphenyl)-2-propyl-1,3-thiazol-5-yl]-2-pyridyl]-N-(3-phenylpropyl)amine,
 N-benzyl-N-[4-[2-butyl-4-(3-methylphenyl)-1,3-thiazol-5-yl]-2-pyridyl]amine,
 N-[4-[2-butyl-4-(3-methylphenyl)-1,3-thiazol-5-yl]-2-pyridyl]-N-(2-phenylethyl)amine,
 N-[4-[2-butyl-4-(3-methylphenyl)-1,3-thiazol-5-yl]-2-pyridyl]-N-(3-phenylpropyl)amine,
 N-benzyl-N-[4-[4-(3-methylphenyl)-2-(4-methylthiophenyl)-1,3-thiazol-5-yl]-2-pyridyl]amine,
 N-[4-[4-(3-methylphenyl)-2-(4-methylthiophenyl)-1,3-thiazol-5-yl]-2-pyridyl]-N-(2-phenylethyl)amine,
 N-[4-[4-(3-methylphenyl)-2-(4-methylthiophenyl)-1,3-thiazol-5-yl]-2-pyridyl]-N-(3-phenylpropyl)amine,
 N-[4-[4-(3-methylphenyl)-2-(4-methylsulfonylphenyl)-1,3-thiazol-5-yl]-2-pyridyl]benzamide,
 N-[4-[4-(3-methylphenyl)-2-(4-methylsulfonylphenyl)-1,3-thiazol-5-yl]-2-pyridyl]phenylacetamide,
 N-[4-[4-(3-methylphenyl)-2-(4-methylsulfonylphenyl)-1,3-thiazol-5-yl]-2-pyridyl]-3-phenylpropionamide,
 N-benzyl-N-[4-[4-(3-methylphenyl)-2-(4-methylsulfonylphenyl)-1,3-thiazol-5-yl]-2-pyridyl]amine,
 N-[4-[4-(3-methylphenyl)-2-(4-methylsulfonylphenyl)-1,3-thiazol-5-yl]-2-pyridyl]-N-(3-phenylpropyl)amine, N-[4-[4-(3-methylphenyl)-2-(4-methylsulfonylphenyl)-1,3-thiazol-5-yl]-2-pyridyl]-N-(2-phenylethyl)amine, or N-(4-fluorobenzyl)-N-[4-[4-(3-methylphenyl)-2-(4-methylsulfonylphenyl)-1,3-thiazol-5-yl]-2-pyridyl]amine, or a salt thereof.

22. A pharmaceutical composition which comprises the compound according to claim 1 together with a pharmacologically acceptable carrier.

* * * * *